United States Patent
Srinivasan et al.

(10) Patent No.: US 11,708,405 B2
(45) Date of Patent: Jul. 25, 2023

(54) IP-10 ANTIBODIES AND THEIR USES

(71) Applicant: BRISTOL-MYERS SQUIBB COMPANY, Princeton, NJ (US)

(72) Inventors: Mohan Srinivasan, Cupertino, CA (US); Shrikant Deshpande, Fremont, CA (US); Qihong Zhao, Princeton, NJ (US); Huadong Sun, Pennington, NJ (US); Ginger Rakestraw, Somerville, MA (US); Guodong Chen, East Brunswick, NJ (US); Richard Y. Huang, Bridgewater, NJ (US); Steven Sheriff, Princeton, NJ (US); Cristian Rodriguez, Princeton, NJ (US); John P. Throup, New Hope, PA (US); Rose A. Dibella, West Roxbury, MA (US)

(73) Assignee: BRISTOL-MYERS QUIBB COMPANY, Princeton, NJ (US)

( * ) Notice: Subject to any disclaimer, the term of this patent is extended or adjusted under 35 U.S.C. 154(b) by 648 days.

(21) Appl. No.: 16/728,757

(22) Filed: Dec. 27, 2019

(65) Prior Publication Data
US 2020/0190180 A1 Jun. 18, 2020

Related U.S. Application Data

(62) Division of application No. 15/364,612, filed on Nov. 30, 2016, now Pat. No. 10,556,948.

(60) Provisional application No. 62/374,622, filed on Aug. 12, 2016, provisional application No. 62/261,210, filed on Nov. 30, 2015.

(51) Int. Cl.
| | |
|---|---|
| *A61K 39/395* | (2006.01) |
| *C07K 16/24* | (2006.01) |
| *A61K 47/68* | (2017.01) |
| *A61K 9/00* | (2006.01) |
| *C07K 16/00* | (2006.01) |
| *A61K 39/00* | (2006.01) |

(52) U.S. Cl.
CPC .......... *C07K 16/24* (2013.01); *A61K 9/0019* (2013.01); *A61K 47/6845* (2017.08); *A61K 2039/505* (2013.01); *A61K 2039/507* (2013.01); *A61K 2039/545* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/565* (2013.01); *C07K 2317/622* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 6,652,854 B2 | 11/2003 | Mohler et al. |
| 7,084,260 B1 | 8/2006 | Lonberg et al. |
| 7,786,268 B2 | 8/2010 | Fischer et al. |
| 7,935,793 B2 | 5/2011 | Balasa et al. |
| 7,964,194 B2 | 6/2011 | Lillard, Jr. et al. |
| 8,258,266 B2 | 9/2012 | Deshpande et al. |
| 8,945,546 B2 | 2/2015 | Deshpande et al. |
| 9,994,633 B2 | 6/2018 | Deshpande et al. |
| 10,556,948 B2 | 2/2020 | Srinivasan et al. |
| 2003/0166589 A1 | 9/2003 | Karin |
| 2004/0096446 A1 | 5/2004 | Lane |
| 2005/0191293 A1 | 9/2005 | Deshpande et al. |
| 2010/0077497 A1 | 3/2010 | Deshpande et al. |
| 2012/0230998 A1 | 9/2012 | Deshpande et al. |
| 2013/0216549 A1 | 8/2013 | Fischer et al. |
| 2014/0127229 A1 | 5/2014 | Luo et al. |
| 2015/0104866 A1 | 4/2015 | Deshpande et al. |
| 2017/0158757 A1 | 6/2017 | Srinivasan et al. |

FOREIGN PATENT DOCUMENTS

| | | |
|---|---|---|
| WO | 0109187 A2 | 2/2001 |
| WO | 0215932 A1 | 2/2002 |
| WO | 2004101511 A2 | 11/2004 |
| WO | 2005/058815 A2 | 6/2005 |
| WO | 2012149320 A1 | 11/2012 |

OTHER PUBLICATIONS

D'Angelo et al. Frontiers in Immunology vol. 9, Article 395 Mar. 2018, pp. 1-13. (Year: 2018).*
Antonelli, A. et al., "Chemokine (C-X-C motif) ligand (CXCL)10 in autoimmune diseases," Autoimmunity Review, vol. 13:272-280. (2014).
Bonvin P. et al. "De novo isolation of antibodies with pH-dependent binding properties", MABS, vol. 7(2):1942-0862 (2015).
Bradbury, A. et al., "Beyond natural antibodies: the power of in vitro display technologies," Nature Biotechnology, vol. 29:245-254 (2011).
Brown, M. et al., "Tolerance to Single, but Not Multiple, Amino Acid Replacements in Antibody VH CDR2," The Journal of Immunology, vol. 156:3285-3291 (1996).

(Continued)

*Primary Examiner* — Chun W Dahle

(57) ABSTRACT

The present invention provides isolated monoclonal antibodies, particularly human antibodies, that bind to IP-10 with high affinity, inhibit the binding of IP-10 to its receptor, inhibit IP-10-induced calcium flux and inhibit IP-10-induced cell migration. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. The invention also provides methods for inhibiting IP-10 activity using the antibodies of the invention, including methods for treating various inflammatory and autoimmune diseases.

21 Claims, 41 Drawing Sheets

Specification includes a Sequence Listing.

(56) References Cited

OTHER PUBLICATIONS

Byrne, F. et al., "An antibody to IP-10 is a potent antagonist of cell migration in vitro and in vivo and does not affect disease in several animal models of inflammation,"Autoimmunity, vol. 42;3:171-182. (2009).
Carr, D. et al., "Effect of Anti-CXCL10 Monoclonal Antibody on Herpes Simplex Virus Type 1 Keratitis and Retinal Infection," Journal of Virology, vol. 77(18):10037-10046 (2003).
Carr, D.J. et al., "Neutralizing Antibody to the Chemokine CXCL10 Reduces Ocular Inflammation and Delays Viral Spread Following Cornea HSV-1 Infection," Invest. Ophthalmol., Abstract No. 4183 (2003).
Dasset, F. et al., "A peptide mimetic of an anti-CD4 monoclonal antibody by rational design,"BBRC, vol. 307, 198-205 (2003).
Fishwild, D. et al., "High-avidity human IgGk monoclonal antibodies from a novel strain of minilocus transgenic mice," Nature Biotechnology, vol. 14:845-851 (1996).
Foung, S.K., et al., "Generation of human monoclonal antibodies by fusion of EBV-activated B cells to a human-mouse hybridoma," Methods Enzymol., vol. 121:168-174 (1986).
Gencore, Sequence alignment, "US-12-172-877-121," pp. 1-4 (2011).
Hu, D et al., "Effective Optimization of Antibody Affinity by Phage Display Integrated with High-Throughput DNA Synthesis and Sequencing Technologies," PLoS ONE 10(6): e0129125. doi:10.1371/journal.pone.0129125 (2015).
International Search Report and Writen Opinion, PCT/US04/41506, 7 pages, dated Dec. 15, 2005.
International Search Report and Written Opinion, PCT/US04/29373, 5 pages, dated Apr. 7, 2005.
International Search Report and Written Opinion, PCT/US2016/064140, dated Apr. 26, 2017, 25 pages.
Invitation to Pay Additional Fees, and, where applicable, Protest Fee, PCT/US2016/064140, dated Mar. 13, 2017, 12 pages.
Janeway, C. et al., "The Immune System in Health and Disease," Immunology Third Edition, Garland Publishing Inc. 1997, Chapters, Structure of the Antibody Molecule and Immunoglobulin Genes, pp. 3:1-3:11.
Klein, R. et al., "IFN-Inducible Protein 10/CXC Chemokine Ligand 10-Independent Induction of Experimental Autoimmune Encephalomyelitis," The Journal of Immunology, vol. 172:550-559 (2004).
Kolb, S. et al., "Identification of a T cell chemotactic factor in the cerebrospinal fluid of HIV-1-infected individuals as interferon-g inducible protein 10," Journal of Neuroimmunology, vol. 93:172-188 (1999).
Kraan, M.C., et al., "The development of clinical signs of rheumatoid synovial inflammation is associated with increased synthesis of the chemokine CXCL8 (interieukin-8)," Arthritis Res., vol. 3(1):65-71 (2001).
Kuhne, M. et al., "MDX-1100, a fully human anti-CSCL10 (IP-10) antibody, is a high affinity, neutralizing antibody that has entered Phase I clinical trials for the treatment of Ulcerative Colitis (UC)," The Journal of Immunology, vol. 178:131.20 (2007).
Kunik, V. et al., "Structural Consensus among Antibodies Defines the Antigen Binding Site," PLoS Comput Biol., vol. 8(2): e1002388 doi:10.1371/journal.pcbi.1002388 (2012).
Liu, Michael T. et al., "Neutralization of the Chemokine CXCL10 Reduces Inflammatory Cell Invasion and Demyelination and Improves Neurological Function in a Viral Model of Multiple Sclerosis," The Journal of Immunology, vol. 167:4091-4097 (2001).
Marks, James D. et al., "By-passing Immunization: Building High Affinity Human Antibodies by Chain Shuffling," Nature Biotechnology, vol. 10:779-783 (1992).
Mayer, L. et al., "Anti-IP-10 antibody (BMS-936557) for ulcerative colitis: a phase II randomised study," Gut, pp. 1-9, doi:10.1136/gutjnl-2012-303424 (2013).
Medarex Inc., "Medarex Announces Primary Endpoint Achieved in MDX-1100 Anti-IP-10 Antibody Phase 2 Trial for Rheumatoid Arthritis," retrieved online at: http://www.medicalnewstoday.com/releases/150119.php, 3 pages (2009).
Pandya, Deepal, "Generation of a high affinity humanized anti-IP-10 monoclonal antibody by protein engineering," The Midwinter Conference of Immunologists, Poster Abstract (2005).
Patel, D.D., et al., "CXCR3 and CCR5 ligands in rheumatoid arthritis synovium," Clin. Immunol., vol. 98(1):39-45 (2001).
Portolano, S. et al., "Lack of promiscuity in autoantigen-specific H and L chain combinations as revealed by human H and L chain 'roulette'," Journal of Immunology, vol. 150:880-887 (1993).
Rader, Christoph et al., "A phage display approach for rapid antibody humanization: Designed combinatorial V gene libraries," Proc. Natl. Acad. Sci. USA, vol. 95:8910-8915 (1998).
Reff, et al., "A review of modifications to recombinant antibodies: attempt to increase efficacy in oncology applications," Critical Reviews in Oncology/Hematology, vol. 40:25-35 (2001).
Rudikoff, S. et al., "Single amino acid substitution altering antigen-binding specificity," Proc. Natl. Acad. Sci. USA, vol. 79:1979-1983 (1982).
Ruschpler, P., et al., "High CXCR3 expression in synovial mast cells associated with CXCL9 and CXCL10 expression in inflammatory synovial tissues of patients with rheumatoid arthritis," Arthritis Res. Ther., vol. 5(5):R241-R252 (2003).
Salomon, I., et al., "Targeting the Function of IFN-g-Inducible Protein 10 Suppresses Ongoing Adjuvant Arthritis," The Journal of Immunology, vol. 169:2685-2693 (2002).
Soderlind, E. et al., "Complementarity-determining region (CDR) implantation: a theme of recombination," Immunotechnology, vol. 4:279-285 (1999).
Srinivasan declaration. Nov. 30, 2011, pp. 1-4.
Supplementary European Search Report for Application No. 04813771.5, 4 pages, dated Jan. 13, 2009.
Swaminathan, J. et al., "Crystal Structures of Oligomeric Forms of the IP-10/CXCL10 Chemokine," Structure, vol. 11:521-532 (2003).
Vajdos, F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Wang, W. et al., "Monoclonal antibody against CXCL-10/IP-10 ameliorates influenza A (H1N1) virus induced acute lung injury," Cell Research, vol. 23:577-580 (2013).
Yellin, M. et al., "A phase II, randomized, double-blind, placebo-controlled study evaluating the efficacy and safety of MDX-1100, a fully human anti-CXCL10 monoclonal antibody, in combination with methotrexate in patients with rheumatoid arthritis," Arthritis Rheum., vol. 64(6):1730-1739 (2012).
U.S. Appl. No. 15/364,612, filed Nov. 30, 2016, Mohan Srinivasan.
U.S. Appl. No. 11/009,731, filed Dec. 10, 2004, Shrikant Deshpande.
U.S. Appl. No. 12/472,877, filed May 27, 2009, Shrikant Deshpande.
U.S. Appl. No. 13/478,786, filed May 23, 2012, Shrikant Deshpande.
U.S. Appl. No. 14/579,156, filed Dec. 22, 2014, Shrikant Deshpande.
U.S. Appl. No. 15/364,612, filed Sep. 25, 2019.
U.S. Appl. No. 15/364,612, filed Apr. 11, 2019.
U.S. Appl. No. 15/364,612, filed Nov. 8, 2018.
U.S. Appl. No. 11/009,731, filed Aug. 31, 2011.
U.S. Appl. No. 11/009,731, filed May 12, 2011.
U.S. Appl. No. 11/009,731, filed May 24, 2010.
U.S. Appl. No. 11/009,731, filed Dec. 8, 2009.
U.S. Appl. No. 11/009,731, filed May 4, 2009.
U.S. Appl. No. 11/009,731, filed Feb. 6, 2008.
U.S. Appl. No. 11/009,731, filed Jul. 10, 2007.
U.S. Appl. No. 11/009,731, filed Dec. 19, 2006.
U.S. Appl. No. 11/009,731, filed Aug. 1, 2006.
U.S. Appl. No. 11/009,731, filed Feb. 13, 2006.
U.S. Appl. No. 11/009,731, filed Nov. 30, 2005.
U.S. Appl. No. 12/472,877, filed Apr. 26, 2012.
U.S. Appl. No. 12/472,877, filed Jan. 20, 2012.
U.S. Appl. No. 12/472,877, filed Aug. 30, 2011.
U.S. Appl. No. 12/472,877, filed Jun. 20, 2011.
U.S. Appl. No. 13/478,786, filed Sep. 17, 2014.
U.S. Appl. No. 13/478,786, filed Apr. 16, 2014.
U.S. Appl. No. 13/478,786, filed Nov. 22, 2013.

(56) References Cited

OTHER PUBLICATIONS

U.S. Appl. No. 14/579,156, filed Jan. 26, 2018.
U.S. Appl. No. 14/579,156, filed Oct. 17, 2017.
U.S. Appl. No. 14/579,156, filed Mar. 20, 2017.

* cited by examiner

Anti-IP10 IP10.1 (6A5) VH

V segment: 3-33
    D segment: 3-10
    J segment: JH6b

```
      Q   M   Q   L   V   E   S   G   G   G   V   V   Q   P   G   R   S   L
  1  CAA ATG CAG CTG GTG GAG TCT GGG GGA GGC GTG GTC CAG CCT GGG AGG TCC CTG

CDR1
                                         -----------------------
      R   L   S   C   T   A   S   G   F   T   F   S   N   N   G   M   H   W
 55  AGA CTC TCC TGT ACA GCG TCT GGA TTC ACC TTC AGT AAC AAT GGC ATG CAC TGG

CDR2
                                                 -----------------------
      V   R   Q   A   P   G   K   G   L   E   W   V   A   V   I   W   F   D
109  GTC CGC CAG GCT CCA GGC AAG GGG CTG GAG TGG GTG GCA GTT ATA TGG TTT GAT

CDR2
     -------------------------------------------------
      G   M   N   K   F   Y   V   D   S   V   K   G   R   F   T   I   S   R
163  GGA ATG AAT AAA TTC TAT GTA GAC TCC GTG AAG GGC CGA TTC ACC ATC TCC AGA

D   N   S   K   N   T   L   Y   L   E   M   N   S   L   R   A   E   D
217  GAC AAT TCC AAG AAC ACG CTG TAT CTG GAA ATG AAC AGC CTG AGA GCC GAG GAC

CDR3
                              ---------------------------------
      T   A   I   Y   Y   C   A   R   E   G   D   G   S   G   I   Y   Y   Y
271  ACG GCT ATA TAT TAC TGT GCG AGA GAA GGG GAT GGT TCG GGG ATT TAT TAC TAC

CDR3
     ----------------------
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 1A

Anti-IP10 IP10.1 (6A5) VK

V segment: A27
J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG AAA AGA

CDR1
                      ------------------------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                                ------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
    -------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                       ----
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
    -----------------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 1B

Anti-IP10 IP44.1 VH

```
      Q   V   Q   L   V   E   S   G   G   G   V   V   Q   P   G   R   S   L
  1  CAA GTG CAG CTG GTG GAG TCT GGG GGA GGC GTG GTC CAG CCT GGG AGG TCC CTG

CDR1
                                        ~~~~~~~~~~~~~~~~~~~~~~
      R   L   S   C   A   A   S   G   F   T   F   S   E   Y   G   M   H   W
 55  AGA CTC TCC TGT GCA GCG TCT GGA TTC ACC TTC AGT GAG TAT GGC ATG CAC TGG

CDR2
                                              ~~~~~~~~~~~~~~~~~~~~~~
      V   R   Q   A   P   G   K   G   L   E   W   V   A   V   I   G   F   A
109  GTC CGC CAG GCT CCA GGC AAG GGG CTG GAG TGG GTG GCA GTT ATA GGG TTT GCT

CDR2
   ~~~~~~~~~~~~~~~~~~~~~~~~~~~~~~~~~~~~~~~~~~~~~~~~~
      G   L   I   K   G   Y   A   D   S   V   K   G   R   F   T   I   S   R
163  GGA CTG ATT AAA GGG TAT GCA GAC TCC GTG AAG GGC CGT TTC ACC ATC TCC AGA

D   N   S   K   N   T   L   Y   L   Q   M   N   S   L   R   A   E   D
217  GAC AAT TCC AAG AAC ACG CTG TAT CTG CAA ATG AAC AGC CTG AGA GCC GAG GAC

CDR3
                                              ~~~~~~~~~~~~~~~~~~~~~~~~~~
      T   A   V   Y   Y   C   A   R   E   G   A   G   S   N   I   Y   Y   Y
271  ACG GCT GTA TAT TAC TGT GCG AGA GAA GGC GCT GGT TCC AAT ATT TAC TAC TAC

CDR3
   ~~~~~~~~~~~~~~~~~~~~~~
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 2A

Anti-IP10 IP10.1 (6A5) VK

V segment: A27
    J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                         ----------------------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                          ------------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
     -----------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                        ----
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
     ---------------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 2B

Anti-IP10 IP10.45 VH

```
      Q   V   Q   L   V   E   S   G   G   G   V   V   Q   P   G   R   S   L
  1 CAA GTG CAG CTG GTG GAG TCT GGG GGA GGC GTG GTC CAG CCT GGG AGG TCC CTG
```

CDR1
                                        ------------------------------------

```
      R   L   S   C   T   A   S   G   F   T   F   S   K   H   G   M   H   W
 55 AGA CTC TCC TGT ACA GCG TCT GGA TTC ACC TTC AGT AAG CAT GGC ATG CAC TGG
```

CDR2
                                                ----------------------------

```
      V   R   Q   A   P   G   K   G   L   E   W   V   A   V   I   G   F   A
109 GTC CGC CAG GCT CCA GGC AAG GGG CTG GAG TGG GTG GCA GTT ATA GGG TTC GCT
```

CDR2
------------------------------

```
      G   V   I   K   S   Y   A   D   S   V   K   G   R   F   T   I   S   R
163 GGA GTC ATT AAA TCG TAT GCA GAC TCC GTG AAG GGC CGA TTC ACC ATC TCC AGA

D   N   S   K   N   T   L   Y   L   Q   M   N   S   L   R   A   E   D
217 GAC AAT TCC AAG AAC ACG CTG TAT CTG CAA ATG AAC AGC CTG AGA GCC GAG GAC
```

CDR3
                                ---------------------------------------------

```
      T   A   V   Y   Y   C   A   R   E   G   E   G   S   N   I   Y   F   Y
271 ACG GCT GTA TAT TAC TGT GCG AGA GAA GGG GAA GGC TCG AAT ATT TAT TTC TAC
```

CDR3
------------------------------

```
      Y   G   M   D   V   W   G   Q   G   T   T   V   T   V   S   S
325 TAT GGT ATG GAC GTC TGG GGC CAA GGG ACC ACG GTC ACC GTC TCC TCA
```

FIG. 3A

Anti-IP10 IP10.45 VK

V segment: A27
    J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG AAA AGA
```

CDR1
                        ------------------------------------------------
```
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG
```

CDR2
                                                ------------------------
```
      Y   Q   Q   K   P   G   Q   A   P   R   L   L   I   Y   G   A   S
109  TAC CAG CAG AAA CCT GGC CAG GCT CCC AGG CTC CTC ATC TAT GGT GCA TCC AGC
```

CDR2
    ------------
```
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC
```

CDR3
                                                                  ------
```
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG
```

CDR3
    ------------------------------------
```
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 3B

Anti-IP10 IP10.46 VH

```
      Q   V   Q   L   V   E   S   G   G   G   V   V   Q   P   G   R   S   L
  1  CAA GTG CAG CTG GTG GAG TCT GGG GGA GGC GTG GTC CAG CCT GGG AGG TCC CTG
```

CDR1
                                                          ~~~~~~~~~~~~~~~~
```
      R   L   S   C   T   A   S   G   F   T   F   S   Q   Y   G   M   H   W
 55  AGA CTC TCC TGT ACA GCG TCT GGA TTC ACC TTC AGT CAG TAT GGC ATG CAC TGG
```

CDR2
                                                ~~~~~~~~~~~~~~~~~~~~
```
      V   R   Q   A   P   G   K   G   L   E   W   V   A   V   I   S   Y   G
109  GTC CGC CAG GCT CCA GGC AAG GGG CTG GAG TGG GTG GCA GTT ATA TCG TAT GGT
```

CDR2
     ~~~~~~~~~~~~~~~~~~~~~~~~~~~~~~~~~~
```
      G   D   I   K   Y   Y   A   D   S   V   K   G   R   F   T   I   S   R
163  GGA GAC ATC AAA TAC TAT GCA GAC TCC GTA AAG GGC CGA TTC ACC ATC TCC AGA

D   N   S   K   N   T   L   Y   L   Q   M   N   S   L   R   A   E   D
217  GAC AAT TCC AAA AAC ACG CTG TAT CTG CAA ATG AAC AGC CTG AGA GCC GAG GAC
```

CDR3
                                        ~~~~~~~~~~~~~~~~~~~~~~~~~~~~~~~~~~
```
      T   A   V   Y   Y   C   A   R   E   G   E   G   S   N   I   Y   Y   Y
271  ACG GCT GTA TAT TAC TGT GCG AGA GAA GGG GAG GGT TCT AAT ATA TAT TAC TAC
```

CDR3
     ~~~~~~~~~~~~~~~~~~~
```
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 4A

Anti-IP10 IP10.46 VK

V segment: A27
   J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                                         -------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                            -----------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
     -----------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                        ----
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
     ---------------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 4B

Anti-IP10 IP10.52 VH

```
      Q   V   Q   L   V   E   S   G   G   G   V   V   Q   P   G   R   S   L
  1 CAA GTG CAG CTG GTG GAG TCT GGG GGA GGC GTG GTC CAG CCT GGG AGG TCC CTG
                                                      CDR1
                                              ---------------------------
      R   L   S   C   T   A   S   G   F   T   F   S   D   Y   G   M   H   W
 55 AGA CTC TCC TGT ACA GCG TCT GGA TTC ACC TTC AGT GAC TAC GGC ATG CAC TGG
                                                                  CDR2
                                                          -----------------
      V   R   Q   A   P   G   K   G   L   E   W   V   A   V   I   G   Y   G
109 GTC CGC CAG GCT CCA GGC AAG GGG CTG GAG TGG GTG GCA GTT ATA GGG TAC GGC
                    CDR2
    ----------------------------------------
      G   L   I   K   G   Y   A   D   S   V   K   G   R   F   T   I   S   R
163 GGA CTG ATT AAA GGA TAT GCA GAC TCC GTG AAG GGC CGA TTC ACC ATC TCC AGA

D   N   S   K   N   T   L   Y   L   Q   M   N   S   L   R   A   E   D
217 GAC AAT TCC AAG AAC ACG CTG TAT CTG CAA ATG AAC AGC CTG AGA GCC GAG GAC
                                                      CDR3
                                              -----------------------------
      T   A   V   Y   Y   C   A   R   E   G   A   G   S   S   V   Y   Y   Y
271 ACG GCT GTA TAT TAC TGT GCG AGA GAA GGG GCA GGT TCG AGT GTG TAT TAC TAC
        CDR3
    ----------------------
      Y   G   M   D   V   W   G   Q   G   T   T   V   T   V   S   S
325 TAC GGT ATG GAC GTC TGG GGC CAA GGG ACC ACG GTC ACC GTC TCC TCA
```

FIG. 5A

Anti-IP10 IP10.52 VK

V segment: A27
    J segment: JK3

```
        E   I   V   L   T   Q   S   P   G   T   L   S   L   S   P   G   E   R
  1   GAA ATT GTG TTG ACG CAG TCT CCA GGC ACC CTG TCT TTG TCT CCA GGG AAA AGA

CDR1
                        ------------------------------------------------------
        A   T   L   S   C   R   A   S   Q   S   V   S   S   S   Y   L   A   W
 55   GCC ACC CTC TCC TGC AGG GCC AGT CAG AGT GTT AGC AGC AGC TAT TTA GCC TGG

CDR2
                                                        ----------------------
        Y   Q   Q   K   P   G   Q   A   P   R   L   L   I   Y   G   A   S   S
109   TAC CAG CAG AAA CCT GGC CAG GCT CCC AGG CTC CTC ATC TAT GGT GCA TCC AGC

CDR2
      -----------
        R   A   T   G   I   P   D   R   F   S   G   S   G   S   G   T   D   F
163   AGG GCC ACT GGC ATC CCA GAC AGG TTC AGT GGC AGT GGG TCT GGG ACA GAC TTC

CDR3
                                                                          ----
        T   L   T   I   S   R   L   E   P   E   D   F   A   V   Y   Y   C   Q
217   ACT CTC ACC ATC AGC AGA CTG GAG CCT GAA GAT TTT GCA GTG TAT TAC TGT CAG

CDR3
      ---------------------------------------
        Q   Y   G   S   S   P   I   F   T   F   G   P   G   T   K   V   D   I
271   CAG TAT GGT AGC TCA CCT ATA TTC ACT TTC GGC CCT GGG ACC AAA GTG GAT ATC

K
325   AAA
```

FIG. 5B

Anti-IP10 IP10.53 VH

```
      Q   V   Q   L   V   E   S   G   G   G   V   V   Q   P   G   R   S   L
  1  CAA GTG CAG CTG GTG GAG TCT GGG GGA GGC GTG GTC CAG CCT GGG AGG TCC CTG

CDR1
                                         ----------------------------
      R   L   S   C   A   A   S   G   F   T   F   S   D   Y   G   M   H   W
 55  AGA CTC TCC TGT GCA GCG TCT GGA TTC ACC TTC AGT GAC TAT GGC ATG CAC TGG

CDR2
                                                         ----------------
      V   R   Q   A   P   G   K   G   L   E   W   V   A   V   I   S   H   N
109  GTC CGC CAG GCT CCA GGC AAG GGG CTG GAG TGG GTG GCA GTT ATA AGC CAT AAT

CDR2
     ------------------------------------------
      G   A   I   K   G   Y   A   D   S   V   K   G   R   F   T   I   S   R
163  GGA GCC ATT AAA GGT TAT GCT GAC TCC GTG AAG GGC CGA TTC ACC ATC TCC AGA

D   N   S   K   N   T   L   Y   L   Q   M   N   S   L   R   A   E   D
217  GAC AAT TCC AAG AAC ACG CTG TAT CTG CAA ATG AAC AGC CTG AGA GCC GAG GAC

CDR3
                                         --------------------------------
      T   A   V   Y   Y   C   A   R   E   G   D   G   S   N   I   Y   Y   Y
271  ACG GCT GTA TAT TAC TGT GCG AGA GAA GGC GAC GGT TCA AAC ATT TAT TAC TAC

CDR3
     -------------------
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 6A

Anti-IP10 IP10.53 VK

V segment: A27
    J segment: JK3

```
      E   I   V   L   T   Q   S   P   G   T   L   S   L   S   P   G   E   R
  1   GAA ATT GTG TTG ACG CAG TCT CCA GGC ACC CTG TCT TTG TCT CCA GGG GAA AGA
```

CDR1
                     ------------------------------------------------

```
      A   T   L   S   C   R   A   S   Q   S   V   S   S   S   Y   L   A   W
 55   GCC ACC CTC TCC TGC AGG GCC AGT CAG AGT GTT AGC AGC AGC TAT TTA GCC TGG
```

CDR2
                                                    ------------------

```
      Y   Q   Q   K   P   G   Q   A   P   R   L   L   I   Y   G   A   S   S
109   TAC CAG CAG AAA CCT GGC CAG GCT CCC AGG CTC CTC ATC TAT GGT GCA TCC AGC
```

CDR2
      ------------

```
      R   A   T   G   I   P   D   R   F   S   G   S   G   S   G   T   D   F
163   AGG GCC ACT GGC ATC CCA GAC AGG TTC AGT GGC AGT GGG TCT GGG ACA GAC TTC
```

CDR3
                                                                    ----

```
      T   L   T   I   S   R   L   E   P   E   D   F   A   V   Y   Y   C   Q
217   ACT CTC ACC ATC AGC AGA CTG GAG CCT GAA GAT TTT GCA GTG TAT TAC TGT CAG
```

CDR3
      ----------------------------

```
      Q   Y   G   S   S   P   I   F   T   F   G   P   G   T   K   V   D   I
271   CAG TAT GGT AGC TCA CCT ATA TTC ACT TTC GGC CCT GGG ACC AAA GTG GAT ATC

K
325   AAA
```

FIG. 6B

Anti-IP10 IP10.43 VH

```
      Q   V   Q   L   V   E   S   G   G   G   V   V   Q   P   G   R   S   L
  1 CAA GTG CAG CTG GTG GAG TCT GGG GGA GGC GTG GTC CAG CCT GGG AGG TCC CTG
```

CDR1
                                                    ~~~~~~~~~~~~~~~~~~~~~~
```
      R   L   S   C   T   A   S   G   F   T   F   S   S   Y   G   M   H   W
 55 AGA CTC TCC TGT ACA GCG TCT GGA TTC ACC TTC AGT TCG TAT GGC ATG CAC TGG
```

CDR2
                                                    ~~~~~~~~~~~~~~~~~~~~~~
```
      V   R   Q   A   P   G   K   G   L   E   W   V   A   V   I   D   F   V
109 GTC CGC CAG GCT CCA GGC AAG GGG CTG GAG TGG GTG GCA GTT ATA GAT TTT GTG
```

CDR2
~~~~~~~~~~~~~~~~~~~~~~~~~~~~~~~~~~~~~~~~~~~~~
```
      G   D   T   K   Y   Y   T   D   S   V   K   G   R   F   T   I   S   R
163 GGA GAC ACT AAA TAC TAT ACA GAC TCC GTG AAG GGC CGA TTC ACC ATC TCC AGA

D   N   S   K   N   T   L   Y   L   Q   M   N   S   L   R   A   E   D
217 GAC AAT TCC AAG AAC ACG CTG TAT CTG CAA ATG AAC AGC CTG AGA GCC GAG GAC
```

CDR3
                                          ~~~~~~~~~~~~~~~~~~~~~~~~~~~~~~~~
```
      T   A   V   Y   Y   C   A   R   E   G   A   G   S   N   I   Y   Y   Y
271 ACG GCT GTA TAT TAC TGT GCG AGA GAA GGG GCT GGT TCG AAC ATT TAT TAT TAC
```

CDR3
~~~~~~~~~~~~~~~~~~~~~~
```
      Y   G   M   D   V   W   G   Q   G   T   T   V   T   V   S   S
325 TAC GGT ATG GAC GTC TGG GGC CAA GGG ACC ACG GTC ACC GTC TCC TCA
```

FIG. 7A

Anti-IP10 IP10.43 VK

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA
```

CDR1
                    ----------------------------------------------

```
      A   T   L   S   C   R   A   S   Q   S   V   S   S   S   H   L   A   W
  55 GCC ACC CTC TCC TGC AGG GCC AGT CAG AGT GTT AGC AGC AGC CAT TTA GCC TGG
```

CDR2
                                                    ------------------

```
      Y   Q   Q   K   P   G   Q   A   P   R   L   L   I   Y   G   A   S   S
 109 TAC CAG CAG AAA CCT GGC CAG GCT CCC AGG CTC CTC ATC TAT GGT GCA TCC AGC
```

CDR2
    -----------

```
      R   A   T   G   I   P   D   R   F   S   G   S   G   S   G   T   D   F
 163 AGG GCC ACT GGC ATC CCA GAC AGG TTC AGT GGC AGT GGG TCT GGG ACA GAC TTC
```

CDR3
                                                                      ----

```
      T   L   T   I   S   R   L   E   P   E   D   F   A   V   Y   Y   C   Q
 217 ACT CTC ACC ATC AGC AGA CTG GAG CCT GAA GAT TTT GCA GTG TAT TAC TGT CAG
```

CDR3
    -------------------------------

```
      Q   Y   G   S   S   P   I   F   T   F   G   P   G   T   K   V   D   I
 271 CAG TAT GGT AGC TCA CCT ATA TTC ACT TTC GGC CCT GGG ACC AAA GTG GAT ATC

K
 325 AAA
```

FIG. 7B

Anti-IP10 IP10.47 VH

```
      Q   V   Q   L   V   E   S   G   G   G   V   V   Q   P   G   R   S   L
  1 CAA GTG CAG CTG GTG GAG TCT GGG GGA GGC GTG GTC CAG CCT GGG AGG TCC CTG

CDR1
                                       ~~~~~~~~~~~~~~~~~~~
      R   L   S   C   A   A   S   G   F   T   F   S   T   H   G   M   H   W
 55 AGA CTC TCC TGT GCA GCG TCT GGA TTC ACC TTC AGT ACC CAT GGC ATG CAC TGG

CDR2
                                            ~~~~~~~~~~~~~~~~~~~
      V   R   Q   A   P   G   K   G   L   E   W   V   A   V   I   G   F   G
109 GTC CGC CAG GCT CCA GGC AAG GGG CTG GAG TGG GTG GCA GTT ATA GGC TTT GGA

CDR2
    ~~~~~~~~~~~~~~~~~~~~~~~~~~~~~~~~~~~
      G   L   I   K   S   Y   A   D   S   V   K   G   R   F   T   I   S   R
163 GGA CTG ATT AAA TCC TAT GCA GAC TCC GTG AAG GGC CGA TTC ACC ATC TCC AGA

D   N   S   K   N   T   L   Y   L   Q   M   N   S   L   R   A   E   D
217 GAC AAT TCC AAG AAC ACG CTG TAT CTG CAA ATG AAC AGC CTG AGA GCC GAG GAC

CDR3
                                       ~~~~~~~~~~~~~~~~~~~~~~~~~~~~~~~~~~~
      T   A   V   Y   Y   C   A   R   E   G   D   G   S   S   L   Y   F   Y
271 ACG GCT GTA TAT TAC TGT GCG AGA GAA GGT GAC GGT TCC AGC CTT TAT TTT TAC

CDR3
    ~~~~~~~~~~~~~~~~~~~
      Y   G   M   D   V   W   G   Q   G   T   T   V   T   V   S   S
325 TAC GGT ATG GAC GTC TGG GGC CAA GGG ACC ACG GTC ACC GTC TCC TCA
```

FIG. 8A

Anti-IP10 IP10.47 VK

V segment: A27  
J segment: JK3

```
      E   I   V   L   T   Q   S   P   G   T   L   S   L   S   P   G   E   R
  1   GAA ATT GTG TTG ACG CAG TCT CCA GGC ACC CTG TCT TTG TCT CCA GGG GAA AGA

CDR1
                         ------------------------------------------------------
      A   T   L   S   C   R   A   S   Q   S   V   S   S   S   Y   L   A   W
 55   GCC ACC CTC TCC TGC AGG GCC AGT CAG AGT GTT AGC AGC AGC TAT TTA GCC TGG

CDR2
                                                           ---------------------
      Y   Q   Q   K   P   G   Q   A   P   R   L   L   I   Y   G   A   S   S
109   TAC CAG CAG AAA CCT GGC CAG GCT CCC AGG CTC CTC ATC TAT GGT GCA TCC AGC

CDR2
      -----------
      R   A   T   G   I   P   D   R   F   S   G   S   G   S   G   T   D   F
163   AGG GCC ACT GGC ATC CCA GAC AGG TTC AGT GGC AGT GGG TCT GGG ACA GAC TTC

CDR3
                                                                          -----
      T   L   T   I   S   R   L   E   P   E   D   F   A   V   Y   Y   C   Q
217   ACT CTC ACC ATC AGC AGA CTG GAG CCT GAA GAT TTT GCA GTG TAT TAC TGT CAG

CDR3
      -------------------------------------------
      Q   Y   G   S   S   P   I   F   T   F   G   P   G   T   K   V   D   I
271   CAG TAT GGT AGC TCA CCT ATA TTC ACT TTC GGC CCT GGG ACC AAA GTG GAT ATC

K
325   AAA
```

FIG. 8B

Anti-IP10 IP10.48 VH

```
      Q   V   Q   L   V   E   S   G   G   G   V   V   Q   P   G   R   S   L
  1  CAA GTG CAG CTG GTG GAG TCT GGG GGA GGC GTG GTC CAG CCT GGG AGG TCC CTG
```

CDR1
                                                    ~~~~~~~~~~~~~~~~~~~~~~~~
```
      R   L   S   C   A   A   S   G   F   T   F   S   N   Y   G   M   H   W
 55  AGA CTC TCC TGT GCA GCG TCT GGA TTC ACC TTC AGT AAC TAT GGC ATG CAC TGG
```

CDR2
                                                    ~~~~~~~~~~~~~~~~~~~~~~~~
```
      V   R   Q   A   P   G   K   G   L   E   W   V   A   V   I   D   F   A
109  GTC CGC CAG GCT CCA GGC AAG GGG CTG GAG TGG GTG GCA GTT ATA GAT TTT GCG
```

CDR2
~~~~~~~~~~~~~~~~~~~~~~~~~~~~~~~~~~~~~~~~~~~~~
```
      G   I   N   K   Y   Y   A   D   S   V   K   G   R   F   T   I   S   R
163  GGA ATC AAT AAA TAC TAT GCA GAC TCC GTG AAG GGC CGA TTC ACC ATC TCC AGA

D   N   S   K   N   T   L   Y   L   Q   M   N   S   L   R   A   E   D
217  GAC AAT TCC AAG AAC ACG CTG TAT CTG CAA ATG AAC AGC CTG AGA GCC GAG GAC
```

CDR3
                                           ~~~~~~~~~~~~~~~~~~~~~~~~~~~~~~~~~
```
      T   A   V   Y   Y   C   A   R   E   G   E   G   S   N   I   Y   F   F
271  ACG GCT GTA TAT TAC TGT GCG AGA GAA GGA GAA GGT TCA AAT ATT TAT TTC TTT
```

CDR3
~~~~~~~~~~~~~~~~~~~~~~
```
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 9A

Anti-IP10 IP10.48 VK

V segment: A27
   J segment: JK3

```
      E   I   V   L   T   Q   S   P   G   T   L   S   L   S   P   G   E   R
  1 GAA ATT GTG TTG ACG CAG TCT CCA GGC ACC CTG TCT TTG TCT CCA GGG GAA AGA
```

CDR1

```
      A   T   L   S   C   R   A   S   Q   S   V   S   S   S   Y   L   A   W
 55 GCC ACC CTC TCC TGC AGG GCC AGT CAG AGT GTT AGC AGC AGC TAT TTA GCC TGG
```

CDR2

```
      Y   Q   Q   K   P   G   Q   A   P   R   L   L   I   Y   G   A   S   S
109 TAC CAG CAG AAA CCT GGC CAG GCT CCC AGG CTC CTC ATC TAT GGT GCA TCC AGC
```

CDR2

```
      R   A   T   G   I   P   D   R   F   S   G   S   G   S   G   T   D   F
163 AGG GCC ACT GGC ATC CCA GAC AGG TTC AGT GGC AGT GGG TCT GGG ACA GAC TTC
```

CDR3

```
      T   L   T   I   S   R   L   E   P   E   D   F   A   V   Y   Y   C   Q
217 ACT CTC ACC ATC AGC AGA CTG GAG CCT GAA GAT TTT GCA GTG TAT TAC TGT CAG
```

CDR3

```
      Q   Y   G   S   S   P   I   F   T   F   G   P   G   T   K   V   D   I
271 CAG TAT GGT AGC TCA CCT ATA TTC ACT TTC GGC CCT GGG ACC AAA GTG GAT ATC

K
325 AAA
```

FIG. 9B

Anti-IP10 IP10.49 VH

```
      Q   V   Q   L   V   E   S   G   G   G   V   V   Q   P   G   R   S   L
  1  CAA GTG CAG CTG GTG GAG TCT GGG GGA GGC GTG GTC CAG CCT GGG AGG TCC CTG
```

CDR1
                                              ------------------------------
```
      R   L   S   C   T   A   S   G   F   T   F   S   Q   S   G   M   H   W
 55  AGA CTC TCC TGT ACA GCG TCT GGA TTC ACC TTC AGT CAG AGT GGC ATG CAC TGG
```

CDR2
                                                        ----------------------
```
      V   R   Q   A   P   G   K   G   L   E   W   V   A   V   I   G   F   G
109  GTC CGC CAG GCT CCA GGC AAG GGG CTG GAG TGG GTG GCA GTT ATA GGG TTT GGC
```

CDR2
  ----------------------------------------------
```
      G   L   I   K   S   Y   A   D   S   V   K   G   R   F   T   I   S   R
163  GGA CTG ATT AAA AGC TAT GCA GAC TCC GTG AAG GGC CGA TTC ACC ATC TCC AGA

D   N   S   K   N   T   L   Y   L   Q   M   N   S   L   R   A   E   D
217  GAC AAT TCC AAG AAC ACG CTG TAT CTG CAA ATG AAC AGC CTG AGA GCC GAG GAC
```

CDR3
                                  ----------------------------------------
```
      T   A   V   Y   Y   C   A   R   E   G   D   G   S   G   I   Y   Y   Y
271  ACG GCT GTA TAT TAC TGT GCG AGA GAA GGG GAT GGT TCG GGG ATT TAT TAC TAC
```

CDR3
  -------------------------
```
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 10A

Anti-IP10 IP10.49 VK

V segment: A27
   J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG AAA AGA

CDR1
                             -----------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                        -----------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
      ------------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                        ----
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
      -----------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 10B

Anti-IP10 IP10.50 VH

```
      Q   V   Q   L   V   E   S   G   G   G   V   V   Q   P   G   R   S   L
  1  CAA GTG CAG CTG GTG GAG TCT GGG GGA GGC GTG GTC CAG CCT GGG AGG TCC CTG
```

CDR1
                                                        ------------------------

```
      R   L   S   C   A   A   S   G   F   T   F   S   R   F   G   M   H   W
 55  AGA CTC TCC TGT GCA GCG TCT GGA TTC ACC TTC AGT CGA TTC GGC ATG CAC TGG
```

CDR2
                                                        ------------------------

```
      V   R   Q   A   P   G   K   G   L   E   W   V   A   V   I   G   Y   A
109  GTC CGC CAG GCT CCA GGC AAG GGG CTG GAG TGG GTG GCA GTT ATA GGG TAC GCG
```

CDR2
------------------------------------------------

```
      G   D   N   K   Y   Y   A   D   S   V   K   G   R   F   T   I   S   R
163  GGA GAC AAT AAA TAT TAT GCA GAC TCC GTG AAG GGC CGA TTC ACC ATC TCC AGA

D   N   S   K   N   T   L   Y   L   Q   M   N   S   L   R   A   E   D
217  GAC AAT TCC AAG AAC ACG CTG TAT CTG CAA ATG AAC AGC CTG AGA GCC GAG GAC
```

CDR3
                                        ----------------------------------------

```
      T   A   V   Y   Y   C   A   R   E   G   A   G   S   N   I   Y   Y   Y
271  ACG GCT GTA TAT TAC TGT GCG AGA GAA GGG GCA GGT TCG AAT ATT TAT TAC TAC
```

CDR3
------------------------

```
      Y   G   M   D   V   W   G   Q   G   T   T   V   T   V   S   S
325  TAC GGT ATG GAC GTC TGG GGC CAA GGG ACC ACG GTC ACC GTC TCC TCA
```

FIG. 11A

Anti-IP10 IP10.50 VK

V segment: A27
    J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                              ------------------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                      --------------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
      -----------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                        ------
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
      ---------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 11B

Anti-IP10 IP10.51 VH

```
      Q   V   Q   L   V   E   S   G   G   G   V   V   Q   P   G   R   S   L
  1 CAA GTG CAG CTG GTG GAG TCT GGG GGA GGC GTG GTC CAG CCT GGG AGG TCC CTG
```

CDR1
                                           ----------------------------------
```
      R   L   S   C   T   A   S   G   F   T   F   S   D   Y   G   M   H   W
 55 AGA CTC TCC TGT ACA GCA TCT GGA TTC ACC TTC AGT GAC TAC GGC ATG CAC TGG
```

CDR2
                                                   ------------------------------
```
      V   R   Q   A   P   G   K   G   L   E   W   V   A   V   I   G   Y   G
109 GTC CGC CAG GCT CCA GGC AAG GGG CTG GAG TGG GTG GCA GTT ATA GGG TAC GGC
```

CDR2
    --------------------------------------------------------
```
      G   L   I   K   G   Y   A   D   S   V   K   G   R   F   T   I   S   R
163 GGA CTG ATT AAA GGA TAT GCA GAC TCC GTG AAG GGC CGA TTC ACC ATC TCC AGA

D   N   S   K   N   T   L   Y   L   Q   M   N   S   L   R   A   E   D
217 GAC AAT TCC AAG AAC ACG CTG TAT CTG CAA ATG AAC AGC CTG AGA GCC GAG GAC
```

CDR3
                                     --------------------------------------------
```
      T   A   V   Y   Y   C   A   R   E   G   A   G   S   S   I   Y   Y   Y
271 ACG GCT GTA TAT TAC TGT GCG AGA GAA GGG GCA GGT TCG AGT ATA TAT TAC TAC
```

CDR3
    ------------------------
```
      Y   G   M   D   V   W   G   Q   G   T   T   V   T   V   S   S
325 TAC GGT ATG GAC GTC TGG GGC CAA GGG ACC ACG GTC ACC GTC TCC TCA
```

FIG. 12A

Anti-IP10 IP10.51 VK

V segment: A27
    J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                          ----------------------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                  ------------------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
     -----------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                      ----
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
     ---------------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 12B

Anti-IP10 IP10.54 VH

```
      Q   V   Q   L   V   E   S   G   G   G   V   V   Q   P   G   R   S   L
  1 CAA GTG CAG CTG GTG GAG TCT GGG GGA GGC GTG GTC CAG CCT GGG AGG TCC CTG

CDR1
                                        ---------------------------
      R   L   S   C   T   A   S   G   F   T   F   S   Q   Y   G   M   H   W
 55 AGA CTC TCC TGT ACA GCG TCT GGA TTC ACC TTC AGT CAG TAT GGC ATG CAC TGG

CDR2
                                                ---------------------
      V   R   Q   A   P   G   K   G   L   E   W   V   A   V   I   S   Y   G
109 GTC CGC CAG GCT CCA GGC AAG GGG CTG GAG TGG GTG GCA GTT ATA TCG TAT GGT

CDR2
    ---------------------------------------------
      G   D   I   K   Y   Y   A   D   S   V   K   G   R   F   T   I   S   R
163 GGA GAC ATC AAA TAC TAT GCA GAC TCC GTA AAG GGC CGA TTC ACC ATC TCC AGA

D   N   S   K   N   T   L   Y   L   E   M   N   S   L   R   A   E   D
217 GAC AAT TCC AAA AAC ACG CTG TAT CTG GAA ATG AAC AGC CTG AGA GCC GAG GAC

CDR3
                                    --------------------------------------
      T   A   I   Y   Y   C   A   R   E   G   E   G   S   N   I   Y   Y   Y
271 ACG GCT ATA TAT TAC TGT GCG AGA GAA GGG GAG GGT TCT AAT ATA TAT TAC TAC

CDR3
    ---------------------
      Y   G   M   D   V   W   G   Q   G   T   T   V   T   V   S   S
325 TAC GGT ATG GAC GTC TGG GGC CAA GGG ACC ACG GTC ACC GTC TCC TCA
```

FIG. 13A

Anti-IP10 IP10.54 VK

V segment: A27
    J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG AAA AGA

CDR1
                         ------------------------------------------------------
      A   T   L   S   C   R   A   S   Q   S   V   S   S   S   Y   L   A   W
 55  GCC ACC CTC TCC TGC AGG GCC AGT CAG AGT GTT AGC AGC AGC TAT TTA GCC TGG

CDR2
                                                              -----------------
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
     -----------
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                         -----
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
     --------------------------------
      Q   Y   G   S   S   P   I   F   T   F   G   P   G   T   K   V   D   I
271  CAG TAT GGT AGC TCA CCT ATA TTC ACT TTC GGC CCT GGG ACC AAA GTG GAT ATC

K
325  AAA
```

FIG. 13B

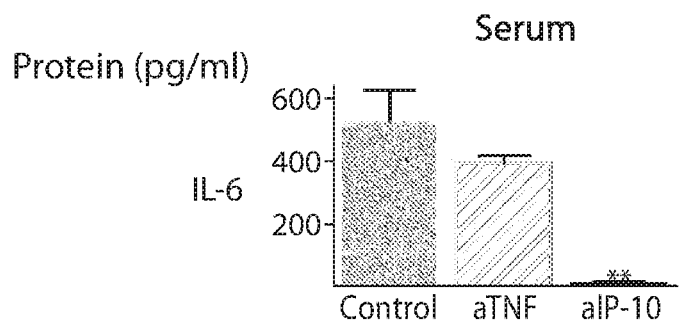
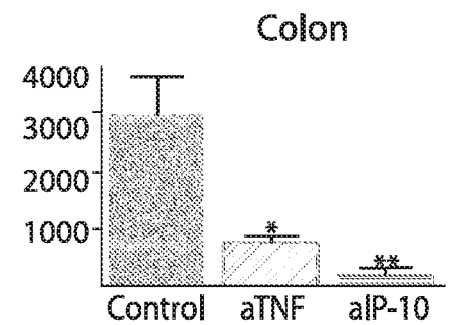
FIG. 18A  FIG. 18B
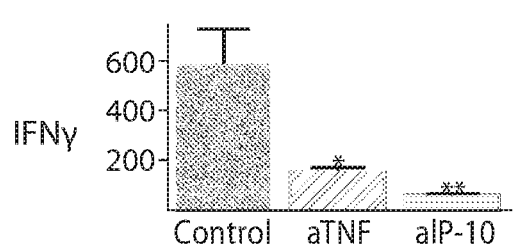
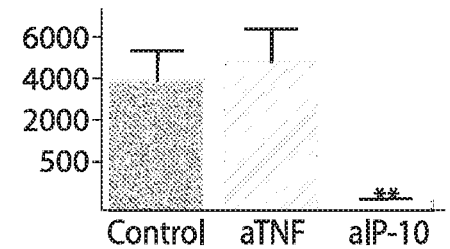
FIG. 18C  FIG. 18D
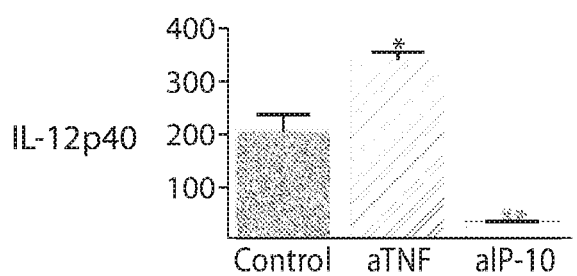
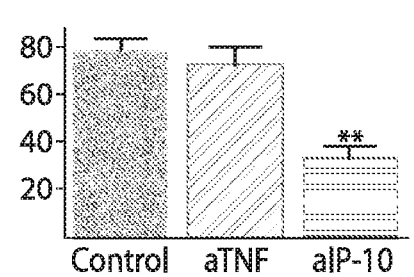
FIG. 18E  FIG. 18F

SEQUENCE LISTING

```
<160> NUMBER OF SEQ ID NOS: 168

<210> SEQ ID NO 1
<211> LENGTH: 5
<212> TYPE: PRT
<213> ORGANISM: Artificial Sequence
<220> FEATURE:
<223> OTHER INFORMATION: Synthetic: VH CDR1 a.a. IP10.1

<400> SEQUENCE: 1

Asn Asn Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic: VH CDR2 a.a. IP10.1

<400> SEQUENCE: 2

Val Ile Trp Phe Asp Gly Met Asn Lys Phe Tyr Val Asp Ser Val Lys
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: Synthetic: VH CDR3 a.a. IP10.1

<400> SEQUENCE: 3

Glu Gly Asp Gly Ser Gly Ile Tyr Tyr Tyr Tyr Gly Met Asp Val
1               5                   10                  15

<210> SEQ ID NO 4
<211> LENGTH: 124
<212> TYPE: PRT
<213> ORGANISM: Artificial Sequence
<220> FEATURE:
<223> OTHER INFORMATION: Synthetic: VH a.a. IP10.1

<400> SEQUENCE: 4

Gln Met Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asn Asn
                20                  25                  30

Gly Met His Trp Val Arg Gln Ala Pro Gly Lys Gly Leu Glu Trp Val
            35                  40                  45

Ala Val Ile Trp Phe Asp Gly Met Asn Lys Phe Tyr Val Asp Ser Val
        50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Ile Tyr Tyr Cys
                85                  90                  95
```

Ala Arg Glu Gly Asp Gly Ser Gly Ile Tyr Tyr Tyr Gly Met Asp
            100                 105                 110

Val Trp Gly Gln Gly Thr Thr Val Thr Val Ser Ser
        115                 120

<210> SEQ ID NO 5
<211> LENGTH: 372
<212> TYPE: DNA
<213> ORGANISM: Artificial Sequence
<220> FEATURE:
<223> OTHER INFORMATION: Synthetic: VH n.t. IP10.1

<400> SEQUENCE: 5
caaatgcagc tggtggagtc tgggggaggc gtggtccagc ctggagggtc cctgagactc      60
tcctgtacag cgtctggatt caccttcagt aacaatggca tgcactgggt ccgccaggct     120
ccaggcaagg ggctggagtg ggtggcagtt atatggtttg atggaatgaa taaattctat     180
gtagactccg tgaagggccg attcaccatc tccagagaca attccaagaa cacgctgtat     240
ctggaaatga acagcctgag agccgaggac acggctatat attactgtgc gagagaaggg     300
gatggttcgg ggatttatta ctactacggt atggacgtct ggggccaagg gaccacggtc     360
accgtctcct ca                                                         372

<210> SEQ ID NO 6
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.1

<400> SEQUENCE: 6

Gln Met Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asn Asn
            20                  25                  30

Gly Met His Trp Val Arg Gln Ala Pro Gly Lys Gly Leu Glu Trp Val
        35                  40                  45

Ala Val Ile Trp Phe Asp Gly Met Asn Lys Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Ile Tyr Tyr Cys
                85                  90                  95

Ala Arg Glu Gly Asp Gly Ser Gly Ile Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                    245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                    325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                    405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Lys
        450

<210> SEQ ID NO 7
<211> LENGTH: 12
<212> TYPE: PRT
<213> ORGANISM: Artificial Sequence
<220> FEATURE:
<223> OTHER INFORMATION: Synthetic: VL CDR1 a.a. IP10.1

<400> SEQUENCE: 7

Arg Ala Ser Gln Ser Val Ser Ser Ser Tyr Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic: VL CDR2 a.a.IP10.1

<400> SEQUENCE: 8

Gly Ala Ser Ser Arg Ala Thr
1               5

<210> SEQ ID NO 9
<211> LENGTH: 10
<212> TYPE: PRT

```
<213> ORGANISM: Artificial Sequence
<220> FEATURE:
<223> OTHER INFORMATION: Synthetic: VL CDR3 a.a. IP10.1

<400> SEQUENCE: 9

Gln Gln Tyr Gly Ser Ser Pro Ile Phe Thr
1               5                   10

<210> SEQ ID NO 10
<211> LENGTH: 109
<212> TYPE: PRT
<213> ORGANISM: Artificial Sequence
<220> FEATURE:
<223> OTHER INFORMATION: Synthetic: VL a.a. IP10.1

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 11
<211> LENGTH: 327
<212> TYPE: DNA
<213> ORGANISM: Artificial Sequence
<220> FEATURE:
<223> OTHER INFORMATION: Synthetic: VL n.t. IP10.1

<400> SEQUENCE: 11
gaaattgtgt tgacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327

<210> SEQ ID NO 12
<211> LENGTH: 216
<212> TYPE: PRT
<213> ORGANISM: Artificial Sequence
<220> FEATURE:
<223> OTHER INFORMATION: Synthetic: Full-length light chain a.a. IP10.1

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
```

-continued

```
                35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Ile Phe Thr Phe Gly Pro Gly Thr Lys Val Asp Ile Lys Arg Thr Val
                100                 105                 110
Ala Ala Pro Ser Val Phe Ile Phe Pro Pro Ser Asp Glu Gln Leu Lys
            115                 120                 125
Ser Gly Thr Ala Ser Val Val Cys Leu Leu Asn Asn Phe Tyr Pro Arg
        130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
Val Tyr Ala Cys Glu Val Thr His Gln Gly Leu Ser Ser Pro Val Thr
        195                 200                 205
Lys Ser Phe Asn Arg Gly Glu Cys
    210                 215

<210> SEQ ID NO 13
<211> LENGTH: 5
<212> TYPE: PRT
<213> ORGANISM: Artificial Sequence
<220> FEATURE:
<223> OTHER INFORMATION: Synthetic: VH CDR1 a.a. IP10.44

<400> SEQUENCE: 13

Glu Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic: VH CDR2 a.a. IP10.44

<400> SEQUENCE: 14

Val Ile Gly Phe Ala Gly Leu Ile Lys Gly Tyr Ala Asp Ser Val Lys
1               5                   10                  15
Gly

<210> SEQ ID NO 15
<211> LENGTH: 15
<212> TYPE: PRT
<213> ORGANISM: Artificial Sequence
<220> FEATURE:
<223> OTHER INFORMATION: Synthetic: VH CDR3 a.a. IP10.44

<400> SEQUENCE: 15

Glu Gly Ala Gly Ser Asn Ile Tyr Tyr Tyr Tyr Gly Met Asp Val
1               5                   10                  15

<210> SEQ ID NO 16
<211> LENGTH: 124
```

<212> TYPE: PRT
<213> ORGANISM: Artificial Sequence
<220> FEATURE:
<223> OTHER INFORMATION: Synthetic: VH a.a. IP10.44

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Tyr
            20                  25                  30

Gly Met His Trp Val Arg Gln Ala Pro Gly Lys Gly Leu Glu Trp Val
        35                  40                  45

Ala Val Ile Gly Phe Ala Gly Leu Ile Lys Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Asn Ile Tyr Tyr Tyr Gly Met Asp
            100                 105                 110

Val Trp Gly Gln Gly Thr Thr Val Thr Val Ser Ser
        115                 120

<210> SEQ ID NO 17
<211> LENGTH: 372
<212> TYPE: DNA
<213> ORGANISM: Artificial Sequence
<220> FEATURE:
<223> OTHER INFORMATION: Synthetic: VH n.t. IP10.44

<400> SEQUENCE: 17
caagtgcagc tggtggagtc tgggggaggc gtggtccagc ctggagggtc cctgagactc      60
tcctgtgcag cgtctggatt caccttcagt gagtatggca tgcactgggt ccgccaggct    120
ccaggcaagg ggctggagtg ggtggcagtt atagggtttg ctggactgat taaagggtat    180
gcagactccg tgaagggccg tttcaccatc tccagagaca attccaagaa cacgctgtat    240
ctgcaaatga acagcctgag agccgaggac acggctgtat attactgtgc gagagaaggc    300
gctggttcca atatttacta ctactacggt atggacgtct ggggccaagg gaccacggtc    360
accgtctcct ca                                                         372

<210> SEQ ID NO 18
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.44

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Tyr
            20                  25                  30

Gly Met His Trp Val Arg Gln Ala Pro Gly Lys Gly Leu Glu Trp Val
        35                  40                  45

Ala Val Ile Gly Phe Ala Gly Leu Ile Lys Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Gly Ala Gly Ser Asn Ile Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 19
<211> LENGTH: 11
<212> TYPE: PRT
<213> ORGANISM: Artificial Sequence
<220> FEATURE:

<223> OTHER INFORMATION: Synthetic: VL CDR1 a.a. IP10.44

<400> SEQUENCE: 19

Arg Ala Ser Gln Ser Val Ser Ser Ser Tyr Leu
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic: VL CDR2 a.a. IP10.44

<400> SEQUENCE: 20

Gly Ala Ser Ser Arg Ala Thr
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic: VL CDR3 a.a. IP10.44

<400> SEQUENCE: 21

Gln Gln Tyr Gly Ser Ser Pro Ile Phe Thr
1               5                   10

<210> SEQ ID NO 22
<211> LENGTH: 109
<212> TYPE: PRT
<213> ORGANISM: Artificial Sequence
<220> FEATURE:
<223> OTHER INFORMATION: Synthetic: VL a.a. IP10.44

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 23
<211> LENGTH: 327
<212> TYPE: DNA
<213> ORGANISM: Artificial Sequence
<220> FEATURE:
<223> OTHER INFORMATION: Synthetic: VL n.t. IP10.44

<400> SEQUENCE: 23
gaaattgtgt tgacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca gcagggccac tggcatccca     180

-continued

```
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327
```

<210> SEQ ID NO 24
<211> LENGTH: 216
<212> TYPE: PRT
<213> ORGANISM: Artificial Sequence
<220> FEATURE:
<223> OTHER INFORMATION: Synthetic: Full-length light chain a.a. IP10.44

<400> SEQUENCE: 24

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 25
<211> LENGTH: 5
<212> TYPE: PRT
<213> ORGANISM: Artificial Sequence
<220> FEATURE:
<223> OTHER INFORMATION: Synthetic: VH CDR1 a.a. IP10.45

<400> SEQUENCE: 25

```
Lys His Gly Met His
1               5
```

<210> SEQ ID NO 26
<211> LENGTH: 17
<212> TYPE: PRT
<213> ORGANISM: Artificial Sequence
<220> FEATURE:
<223> OTHER INFORMATION: Synthetic: VH CDR2 a.a. IP10.45

<400> SEQUENCE: 26

Val Ile Gly Phe Ala Gly Val Ile Lys Ser Tyr Ala Asp Ser Val Lys
1               5                   10                  15

Gly

<210> SEQ ID NO 27
<211> LENGTH: 15
<212> TYPE: PRT
<213> ORGANISM: Artificial Sequence
<220> FEATURE:
<223> OTHER INFORMATION: Synthetic: VH CDR3 a.a. IP10.45

<400> SEQUENCE: 27

Glu Gly Glu Gly Ser Asn Ile Tyr Phe Tyr Tyr Gly Met Asp Val
1               5                   10                  15

<210> SEQ ID NO 28
<211> LENGTH: 124
<212> TYPE: PRT
<213> ORGANISM: Artificial Sequence
<220> FEATURE:
<223> OTHER INFORMATION: Synthetic: VH a.a. IP10.45

<400> SEQUENCE: 28

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Lys His
                20                  25                  30

Gly Met His Trp Val Arg Gln Ala Pro Gly Lys Gly Leu Glu Trp Val
            35                  40                  45

Ala Val Ile Gly Phe Ala Gly Val Ile Lys Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Gly Ser Asn Ile Tyr Phe Tyr Tyr Gly Met Asp
            100                 105                 110

Val Trp Gly Gln Gly Thr Thr Val Thr Val Ser Ser
        115                 120

<210> SEQ ID NO 29
<211> LENGTH: 372
<212> TYPE: DNA
<213> ORGANISM: Artificial Sequence
<220> FEATURE:
<223> OTHER INFORMATION: Synthetic: VH n.t. IP10.45

<400> SEQUENCE: 29
caagtgcagc tggtggagtc tgggggaggc gtggtccagc ctggggaggtc cctgagactc      60 tcctgtacag cgtctggatt caccttcagt aagcatggca tgcactgggt ccgccaggct     120
ccaggcaagg ggctggagtg ggtggcagtt atagggttcg ctggagtcat taaatcgtat     180
gcagactccg tgaagggccg attcaccatc tccagagaca attccaagaa cacgctgtat     240
ctgcaaatga acagcctgag agccgaggac acggctgtat attactgtgc gagagaaggg     300
gaaggctcga atatttattt ctactatggt atggacgtct ggggccaagg gaccacggtc     360
accgtctcct ca                                                        372

```
<210> SEQ ID NO 30
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.45

<400> SEQUENCE: 30
```

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Lys His
            20                  25                  30

Gly Met His Trp Val Arg Gln Ala Pro Gly Lys Gly Leu Glu Trp Val
        35                  40                  45

Ala Val Ile Gly Phe Ala Gly Val Ile Lys Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Gly Ser Asn Ile Tyr Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

-continued

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 31
<211> LENGTH: 12
<212> TYPE: PRT
<213> ORGANISM: Artificial Sequence
<220> FEATURE:
<223> OTHER INFORMATION: Synthetic: VL CDR1 a.a. IP10.45

<400> SEQUENCE: 31

Arg Ala Ser Gln Ser Val Ser Ser Ser Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic: VL CDR2 a.a. IP10.45

<400> SEQUENCE: 32

Gly Ala Ser Ser Arg Ala Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic: VL CDR3 a.a. IP10.45

<400> SEQUENCE: 33

Gln Gln Tyr Gly Ser Ser Pro Ile Phe Thr
1               5                   10

<210> SEQ ID NO 34
<211> LENGTH: 109
<212> TYPE: PRT
<213> ORGANISM: Artificial Sequence
<220> FEATURE:
<223> OTHER INFORMATION: Synthetic: VL a.a. IP10.45

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Phe Thr Phe Gly Pro Gly Thr Lys Val Asp Ile Lys
            100                 105
```

<210> SEQ ID NO 35
<211> LENGTH: 327
<212> TYPE: DNA
<213> ORGANISM: Artificial Sequence
<220> FEATURE:
<223> OTHER INFORMATION: Synthetic: VL n.t. IP10.45

<400> SEQUENCE: 35

```
gaaattgtgt tgacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327
```

<210> SEQ ID NO 36
<211> LENGTH: 216
<212> TYPE: PRT
<213> ORGANISM: Artificial Sequence
<220> FEATURE:
<223> OTHER INFORMATION: Synthetic: Full-length light chain a.a. IP10.45

<400> SEQUENCE: 36

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205
```

```
Lys Ser Phe Asn Arg Gly Glu Cys
    210             215
```

```
<210> SEQ ID NO 37
<211> LENGTH: 5
<212> TYPE: PRT
<213> ORGANISM: Artificial Sequence
<220> FEATURE:
<223> OTHER INFORMATION: Synthetic: VH CDR1 a.a. IP10.46

<400> SEQUENCE: 37

Gln Tyr Gly Met His
1               5
```

```
<210> SEQ ID NO 38
<211> LENGTH: 17
<212> TYPE: PRT
<213> ORGANISM: Artificial Sequence
<220> FEATURE:
<223> OTHER INFORMATION: Synthetic: VH CDR2 a.a. IP10.46

<400> SEQUENCE: 38

Val Ile Ser Tyr Gly Gly Asp Ile Lys Tyr Tyr Ala Asp Ser Val Lys
1               5                   10                  15
Gly
```

```
<210> SEQ ID NO 39
<211> LENGTH: 15
<212> TYPE: PRT
<213> ORGANISM: Artificial Sequence
<220> FEATURE:
<223> OTHER INFORMATION: Synthetic: VH CDR3 a.a. IP10.46

<400> SEQUENCE: 39

Glu Gly Glu Gly Ser Asn Ile Tyr Tyr Tyr Gly Met Asp Val
1               5                   10                  15
```

```
<210> SEQ ID NO 40
<211> LENGTH: 124
<212> TYPE: PRT
<213> ORGANISM: Artificial Sequence
<220> FEATURE:
<223> OTHER INFORMATION: Synthetic: VH a.a. IP10.46

<400> SEQUENCE: 40

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Gln Tyr
            20                  25                  30

Gly Met His Trp Val Arg Gln Ala Pro Gly Lys Gly Leu Glu Trp Val
        35                  40                  45

Ala Val Ile Ser Tyr Gly Gly Asp Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Gly Ser Asn Ile Tyr Tyr Tyr Gly Met Asp
                100                 105                 110

Val Trp Gly Gln Gly Thr Thr Val Thr Val Ser Ser
            115                 120
```

<210> SEQ ID NO 41
<211> LENGTH: 372
<212> TYPE: DNA
<213> ORGANISM: Artificial Sequence
<220> FEATURE:
<223> OTHER INFORMATION: Synthetic: VH n.t. IP10.46

<400> SEQUENCE: 41

```
caagtgcagc tggtggagtc tgggggaggc gtggtccagc ctggggaggtc cctgagactc      60 tcctgtacag cgtctggatt caccttcagt cagtatggca tgcactgggt ccgccaggct     120
ccaggcaagg ggctggagtg ggtggcagtt atatcgtatg gtggagacat caaatactat     180
gcagactccg taaagggccg attcaccatc tccagagaca attccaaaaa cacgctgtat     240
ctgcaaatga acagcctgag agccgaggac acggctgtat attactgtgc gagagaaggg     300
gagggttcta atatatatta ctactacggt atggacgtct ggggccaagg gaccacggtc     360
accgtctcct ca                                                        372
```

<210> SEQ ID NO 42
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.46

<400> SEQUENCE: 42

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gln Tyr
            20                  25                  30

Gly Met His Trp Val Arg Gln Ala Pro Gly Lys Gly Leu Glu Trp Val
        35                  40                  45

Ala Val Ile Ser Tyr Gly Gly Asp Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Gly Ser Asn Ile Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

```
Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 43
<211> LENGTH: 12
<212> TYPE: PRT
<213> ORGANISM: Artificial Sequence
<220> FEATURE:
<223> OTHER INFORMATION: Synthetic: VL CDR1 a.a. IP10.46

<400> SEQUENCE: 43

Arg Ala Ser Gln Ser Val Ser Ser Ser Tyr Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic: VL CDR2 a.a. IP10.46

<400> SEQUENCE: 44

Gly Ala Ser Ser Arg Ala Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic: VL CDR3 a.a. IP10.46

<400> SEQUENCE: 45

Gln Gln Tyr Gly Ser Ser Pro Ile Phe Thr
```

<210> SEQ ID NO 46
<211> LENGTH: 109
<212> TYPE: PRT
<213> ORGANISM: Artificial Sequence
<220> FEATURE:
<223> OTHER INFORMATION: Synthetic: VL a.a. IP10.46

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 47
<211> LENGTH: 327
<212> TYPE: DNA
<213> ORGANISM: Artificial Sequence
<220> FEATURE:
<223> OTHER INFORMATION: Synthetic: VL n.t. IP10.46

<400> SEQUENCE: 47
gaaattgtgt tgacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327

<210> SEQ ID NO 48
<211> LENGTH: 216
<212> TYPE: PRT
<213> ORGANISM: Artificial Sequence
<220> FEATURE:
<223> OTHER INFORMATION: Synthetic: Full-length light chain a.a. IP10.46

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 49
<211> LENGTH: 5
<212> TYPE: PRT
<213> ORGANISM: Artificial Sequence
<220> FEATURE:
<223> OTHER INFORMATION: Synthetic: VH CDR1 a.a. IP10.52

<400> SEQUENCE: 49

Asp Tyr Gly Met His
1               5

<210> SEQ ID NO 50
<211> LENGTH: 17
<212> TYPE: PRT
<213> ORGANISM: Artificial Sequence
<220> FEATURE:
<223> OTHER INFORMATION: Synthetic: VH CDR2 a.a. IP10.52

<400> SEQUENCE: 50

Val Ile Gly Tyr Gly Gly Leu Ile Lys Gly Tyr Ala Asp Ser Val Lys
1               5                   10                  15

Gly

<210> SEQ ID NO 51
<211> LENGTH: 15
<212> TYPE: PRT
<213> ORGANISM: Artificial Sequence
<220> FEATURE:
<223> OTHER INFORMATION: Synthetic: VH CDR3 a.a. IP10.52

<400> SEQUENCE: 51

Glu Gly Ala Gly Ser Ser Val Tyr Tyr Tyr Gly Met Asp Val
1               5                   10                  15

<210> SEQ ID NO 52
<211> LENGTH: 124
<212> TYPE: PRT
<213> ORGANISM: Artificial Sequence
<220> FEATURE:
<223> OTHER INFORMATION: Synthetic: VH a.a. IP10.52

<400> SEQUENCE: 52
```

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asp Tyr
            20                  25                  30

Gly Met His Trp Val Arg Gln Ala Pro Gly Lys Gly Leu Glu Trp Val
            35                  40                  45

Ala Val Ile Gly Tyr Gly Gly Leu Ile Lys Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Ser Val Tyr Tyr Tyr Tyr Gly Met Asp
            100                 105                 110

Val Trp Gly Gln Gly Thr Thr Val Thr Val Ser Ser
        115                 120

<210> SEQ ID NO 53
<211> LENGTH: 372
<212> TYPE: DNA
<213> ORGANISM: Artificial Sequence
<220> FEATURE:
<223> OTHER INFORMATION: Synthetic: VH n.t. IP10.52

<400> SEQUENCE: 53
caagtgcagc tggtggagtc tgggggaggc gtggtccagc ctggagggtc cctgagactc      60
tcctgtacag cgtctggatt caccttcagt gactacggca tgcactgggt ccgccaggct     120
ccaggcaagg ggctggagtg ggtggcagtt ataggtacg gcggactgat taaggatat     180 gcagactccg tgaagggccg attcaccatc tccagagaca attccaagaa cacgctgtat     240
ctgcaaatga acagcctgag agccgaggac acggctgtat attactgtgc gagagaaggg     300
gcaggttcga gtgtgtatta ctactacggt atggacgtct ggggccaagg gaccacggtc     360
accgtctcct ca                                                         372

<210> SEQ ID NO 54
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.52

<400> SEQUENCE: 54

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asp Tyr
            20                  25                  30

Gly Met His Trp Val Arg Gln Ala Pro Gly Lys Gly Leu Glu Trp Val
            35                  40                  45

Ala Val Ile Gly Tyr Gly Gly Leu Ile Lys Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Ser Val Tyr Tyr Tyr Tyr Gly Met Asp
            100                 105                 110

```
Val Trp Gly Gln Gly Thr Thr Val Thr Val Ser Ser Ala Ser Thr Lys
            115                 120                 125
Gly Pro Ser Val Phe Pro Leu Ala Pro Ser Ser Lys Ser Thr Ser Gly
130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Leu Gly Thr Gln Thr Tyr Ile Cys Asn
        195                 200                 205
Val Asn His Lys Pro Ser Asn Thr Lys Val Asp Lys Arg Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 55
<211> LENGTH: 12
<212> TYPE: PRT
<213> ORGANISM: Artificial Sequence
<220> FEATURE:
<223> OTHER INFORMATION: Synthetic: VL CDR1 a.a. IP10.52

<400> SEQUENCE: 55

Arg Ala Ser Gln Ser Val Ser Ser Tyr Leu Ala
1               5                   10
```

<210> SEQ ID NO 56
<211> LENGTH: 7
<212> TYPE: PRT
<213> ORGANISM: Artificial Sequence
<220> FEATURE:
<223> OTHER INFORMATION: Synthetic: VL CDR2 a.a. IP10.52

<400> SEQUENCE: 56

Gly Ala Ser Ser Arg Ala Thr
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic: VL CDR3 a.a. IP10.52

<400> SEQUENCE: 57

Gln Gln Tyr Gly Ser Ser Pro Ile Phe Thr
1               5                   10

<210> SEQ ID NO 58
<211> LENGTH: 109
<212> TYPE: PRT
<213> ORGANISM: Artificial Sequence
<220> FEATURE:
<223> OTHER INFORMATION: Synthetic: VL a.a. IP10.52

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 59
<211> LENGTH: 327
<212> TYPE: DNA
<213> ORGANISM: Artificial Sequence
<220> FEATURE:
<223> OTHER INFORMATION: Synthetic: VL n.t. IP10.52

<400> SEQUENCE: 59
gaaattgtgt tgacgcagtc tccaggcacc ctgtctttgt ctccagggga aagagccacc     60
ctctcctgca gggccagtca gagtgttagc agcagctatt tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctat attcactttc    300
ggccctggga ccaaagtgga tatcaaa                                        327

-continued

<210> SEQ ID NO 60
<211> LENGTH: 216
<212> TYPE: PRT
<213> ORGANISM: Artificial Sequence
<220> FEATURE:
<223> OTHER INFORMATION: Synthetic: Full-length light chain a.a. IP10.52

<400> SEQUENCE: 60

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 61
<211> LENGTH: 5
<212> TYPE: PRT
<213> ORGANISM: Artificial Sequence
<220> FEATURE:
<223> OTHER INFORMATION: Synthetic: VH CDR1 a.a. IP10.53

<400> SEQUENCE: 61

```
Asp Tyr Gly Met His
1               5
```

<210> SEQ ID NO 62
<211> LENGTH: 17
<212> TYPE: PRT
<213> ORGANISM: Artificial Sequence
<220> FEATURE:
<223> OTHER INFORMATION: Synthetic: VH CDR2 a.a. IP10.53

<400> SEQUENCE: 62

```
Val Ile Ser His Asn Gly Ala Ile Lys Gly Tyr Ala Asp Ser Val Lys
1               5                   10                  15

Gly
```

<210> SEQ ID NO 63
<211> LENGTH: 15
<212> TYPE: PRT
<213> ORGANISM: Artificial Sequence
<220> FEATURE:
<223> OTHER INFORMATION: Synthetic: VH CDR3 a.a. IP10.53

<400> SEQUENCE: 63

Glu Gly Asp Gly Ser Asn Ile Tyr Tyr Tyr Gly Met Asp Val
1               5                   10                  15

<210> SEQ ID NO 64
<211> LENGTH: 124
<212> TYPE: PRT
<213> ORGANISM: Artificial Sequence
<220> FEATURE:
<223> OTHER INFORMATION: Synthetic: VH a.a. IP10.53

<400> SEQUENCE: 64

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Ser His Asn Gly Ala Ile Lys Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Gly Ser Asn Ile Tyr Tyr Tyr Gly Met Asp
            100                 105                 110

Val Trp Gly Gln Gly Thr Thr Val Thr Val Ser Ser
        115                 120

<210> SEQ ID NO 65
<211> LENGTH: 372
<212> TYPE: DNA
<213> ORGANISM: Artificial Sequence
<220> FEATURE:
<223> OTHER INFORMATION: Synthetic: VH n.t. IP10.53

<400> SEQUENCE: 65
caagtgcagc tggtggagtc tgggggaggc gtggtccagc ctggagggtc cctgagactc      60
tcctgtgcag cgtctggatt caccttcagt gactatggca tgcactgggt ccgccaggct     120
ccaggcaagg ggctggagtg ggtggcagtt ataagccata atggagccat taaaggttat     180
gctgactccg tgaagggccg attcaccatc tccagagaca attccaagaa cacgctgtat     240
ctgcaaatga acagcctgag agccgaggac acggctgtat attactgtgc gagagaaggc     300
gacggttcaa acatttatta ctactacggt atggacgtct ggggccaagg gaccacggtc     360
accgtctcct ca                                                          372

<210> SEQ ID NO 66
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.53

<400> SEQUENCE: 66

| | | | | | | | | | | | | | | |
|---|---|---|---|---|---|---|---|---|---|---|---|---|---|---|
| Gln | Val | Gln | Leu | Val | Glu | Ser | Gly | Gly | Val | Val | Gln | Pro | Gly | Arg |
| 1 | | | | 5 | | | | | 10 | | | | | 15 |
| Ser | Leu | Arg | Leu | Ser | Cys | Ala | Ala | Ser | Gly | Phe | Thr | Phe | Ser | Asp | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Val | Ile | Ser | His | Asn | Gly | Ala | Ile | Lys | Gly | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Glu | Gly | Asp | Gly | Ser | Asn | Ile | Tyr | Tyr | Tyr | Gly | Met | Asp |
| | | | 100 | | | | | 105 | | | | | 110 | |
| Val | Trp | Gly | Gln | Gly | Thr | Thr | Val | Thr | Val | Ser | Ser | Ala | Ser | Thr | Lys |
| | | 115 | | | | | 120 | | | | | 125 | | | |
| Gly | Pro | Ser | Val | Phe | Pro | Leu | Ala | Pro | Ser | Ser | Lys | Ser | Thr | Ser | Gly |
| | 130 | | | | | 135 | | | | | 140 | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Ser | Leu | Gly | Thr | Gln | Thr | Tyr | Ile | Cys | Asn |
| | | 195 | | | | | 200 | | | | | 205 | | | |
| Val | Asn | His | Lys | Pro | Ser | Asn | Thr | Lys | Val | Asp | Lys | Arg | Val | Glu | Pro |
| | 210 | | | | | 215 | | | | | 220 | | | | |
| Lys | Ser | Cys | Asp | Lys | Thr | His | Thr | Cys | Pro | Pro | Cys | Pro | Ala | Pro | Glu |
| 225 | | | | | 230 | | | | | 235 | | | | | 240 |
| Leu | Leu | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | 275 | | | | | 280 | | | | | 285 | | | |
| Val | Glu | Val | His | Asn | Ala | Lys | Thr | Lys | Pro | Arg | Glu | Glu | Gln | Tyr | Asn |
| | 290 | | | | | 295 | | | | | 300 | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Pro |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Ser | Arg | Glu | Glu | Met | Thr | Lys | Asn |
| | | 355 | | | | | 360 | | | | | 365 | | | |
| Gln | Val | Ser | Leu | Thr | Cys | Leu | Val | Lys | Gly | Phe | Tyr | Pro | Ser | Asp | Ile |
| | 370 | | | | | 375 | | | | | 380 | | | | |
| Ala | Val | Glu | Trp | Glu | Ser | Asn | Gly | Gln | Pro | Glu | Asn | Asn | Tyr | Lys | Thr |
| 385 | | | | | 390 | | | | | 395 | | | | | 400 |
| Thr | Pro | Pro | Val | Leu | Asp | Ser | Asp | Gly | Ser | Phe | Phe | Leu | Tyr | Ser | Lys |

```
                    405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 67
<211> LENGTH: 12
<212> TYPE: PRT
<213> ORGANISM: Artificial Sequence
<220> FEATURE:
<223> OTHER INFORMATION: Synthetic: VL CDR1 a.a. IP10.53

<400> SEQUENCE: 67

Arg Ala Ser Gln Ser Val Ser Ser Ser Tyr Leu Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetic: VL CDR2 a.a. IP10.53

<400> SEQUENCE: 68

Gly Ala Ser Ser Arg Ala Thr
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic: VL CDR3 a.a. IP10.53

<400> SEQUENCE: 69

Gln Gln Tyr Gly Ser Ser Pro Ile Phe Thr
1               5                   10

<210> SEQ ID NO 70
<211> LENGTH: 109
<212> TYPE: PRT
<213> ORGANISM: Artificial Sequence
<220> FEATURE:
<223> OTHER INFORMATION: Synthetic: VL a.a. IP10.53

<400> SEQUENCE: 70

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
                100                 105
```

<210> SEQ ID NO 71
<211> LENGTH: 327
<212> TYPE: DNA
<213> ORGANISM: Artificial Sequence
<220> FEATURE:
<223> OTHER INFORMATION: Synthetic: VL n.t. IP10.53

<400> SEQUENCE: 71

```
gaaattgtgt tgacgcagtc tccaggcacc ctgtctttgt ctccagggga aagagccacc    60
ctctcctgca gggccagtca gagtgttagc agcagctatt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctat attcactttc   300
ggccctggga ccaaagtgga tatcaaa                                       327
```

<210> SEQ ID NO 72
<211> LENGTH: 216
<212> TYPE: PRT
<213> ORGANISM: Artificial Sequence
<220> FEATURE:
<223> OTHER INFORMATION: Synthetic: Full-length light chain a.a. IP10.53

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 73
<211> LENGTH: 5

```
<212> TYPE: PRT
<213> ORGANISM: Artificial Sequence
<220> FEATURE:
<223> OTHER INFORMATION: Synthetic: VH CDR1 a.a. IP10.43

<400> SEQUENCE: 73

Ser Tyr Gly Met His
1               5

<210> SEQ ID NO 74
<211> LENGTH: 17
<212> TYPE: PRT
<213> ORGANISM: Artificial Sequence
<220> FEATURE:
<223> OTHER INFORMATION: Synthetic: VH CDR2 a.a. IP10.43

<400> SEQUENCE: 74

Val Ile Asp Phe Val Gly Asp Thr Lys Tyr Tyr Thr Asp Ser Val Lys
1               5                   10                  15

Gly

<210> SEQ ID NO 75
<211> LENGTH: 15
<212> TYPE: PRT
<213> ORGANISM: Artificial Sequence
<220> FEATURE:
<223> OTHER INFORMATION: Synthetic: VH CDR3 a.a. IP10.43

<400> SEQUENCE: 75

Glu Gly Ala Gly Ser Asn Ile Tyr Tyr Tyr Tyr Gly Met Asp Val
1               5                   10                  15

<210> SEQ ID NO 76
<211> LENGTH: 124
<212> TYPE: PRT
<213> ORGANISM: Artificial Sequence
<220> FEATURE:
<223> OTHER INFORMATION: Synthetic: VH a.a. IP10.43

<400> SEQUENCE: 76

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Asp Phe Val Gly Asp Thr Lys Tyr Tyr Thr Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Asn Ile Tyr Tyr Tyr Tyr Gly Met Asp
            100                 105                 110

Val Trp Gly Gln Gly Thr Thr Val Thr Val Ser Ser
        115                 120

<210> SEQ ID NO 77
<211> LENGTH: 372
<212> TYPE: DNA
<213> ORGANISM: Artificial Sequence
<220> FEATURE:
<223> OTHER INFORMATION: Synthetic: VH n.t. IP10.43
```

<400> SEQUENCE: 77

```
caagtgcagc tggtggagtc tgggggaggc gtggtccagc ctggagggtc cctgagactc    60
tcctgtacag cgtctggatt caccttcagt tcgtatggca tgcactgggt ccgccaggct   120
ccaggcaagg gctggagtg gtggcagtt atagattttg tgggagacac taaatactat   180
acagactccg tgaagggccg attcaccatc tccagagaca attccaagaa cacgctgtat   240
ctgcaaatga acagcctgag agccgaggac acggctgtat attactgtgc gagagaaggg   300
gctggttcga acatttatta ttactacggt atggacgtct ggggccaagg gaccacggtc   360
accgtctcct ca                                                       372
```

<210> SEQ ID NO 78
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.43

<400> SEQUENCE: 78

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Asp Phe Val Gly Asp Thr Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Asn Ile Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
```

```
                275                 280                 285
Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 79
<211> LENGTH: 12
<212> TYPE: PRT
<213> ORGANISM: Artificial Sequence
<220> FEATURE:
<223> OTHER INFORMATION: Synthetic: VL CDR1 a.a. IP10.43

<400> SEQUENCE: 79

Arg Ala Ser Gln Ser Val Ser Ser Ser His Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Synthetic: VL CDR2 a.a.IP10.43

<400> SEQUENCE: 80

Gly Ala Ser Ser Arg Ala Thr
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic: VL CDR3 a.a. IP10.43

<400> SEQUENCE: 81

Gln Gln Tyr Gly Ser Ser Pro Ile Phe Thr
1               5                   10

<210> SEQ ID NO 82
<211> LENGTH: 109
<212> TYPE: PRT
<213> ORGANISM: Artificial Sequence
```

<220> FEATURE:
<223> OTHER INFORMATION: Synthetic: VL a.a. IP10.43

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 83
<211> LENGTH: 327
<212> TYPE: DNA
<213> ORGANISM: Artificial Sequence
<220> FEATURE:
<223> OTHER INFORMATION: Synthetic: VL n.t. IP10.43

<400> SEQUENCE: 83
gaaattgtgt tgacgcagtc tccaggcacc ctgtctttgt ctccagggga aagagccacc      60
ctctcctgca gggccagtca gagtgttagc agcagccatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327

<210> SEQ ID NO 84
<211> LENGTH: 216
<212> TYPE: PRT
<213> ORGANISM: Artificial Sequence
<220> FEATURE:
<223> OTHER INFORMATION: Synthetic: Full-length light chain a.a. IP10.43

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

```
Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
        210                 215

<210> SEQ ID NO 85
<211> LENGTH: 5
<212> TYPE: PRT
<213> ORGANISM: Artificial Sequence
<220> FEATURE:
<223> OTHER INFORMATION: Synthetic: VH CDR1 a.a. IP10.47

<400> SEQUENCE: 85

Thr His Gly Met His
1               5

<210> SEQ ID NO 86
<211> LENGTH: 17
<212> TYPE: PRT
<213> ORGANISM: Artificial Sequence
<220> FEATURE:
<223> OTHER INFORMATION: Synthetic: VH CDR2 a.a. IP10.47

<400> SEQUENCE: 86

Val Ile Gly Phe Gly Gly Leu Ile Lys Ser Tyr Ala Asp Ser Val Lys
1               5                   10                  15

Gly

<210> SEQ ID NO 87
<211> LENGTH: 15
<212> TYPE: PRT
<213> ORGANISM: Artificial Sequence
<220> FEATURE:
<223> OTHER INFORMATION: Synthetic: VH CDR3 a.a. IP10.47

<400> SEQUENCE: 87

Glu Gly Asp Gly Ser Ser Leu Tyr Phe Tyr Tyr Gly Met Asp Val
1               5                   10                  15

<210> SEQ ID NO 88
<211> LENGTH: 124
<212> TYPE: PRT
<213> ORGANISM: Artificial Sequence
<220> FEATURE:
<223> OTHER INFORMATION: Synthetic: VH a.a. IP10.47

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr His
            20                  25                  30

Gly Met His Trp Val Arg Gln Ala Pro Gly Lys Gly Leu Glu Trp Val
```

```
                35                  40                  45
Ala Val Ile Gly Phe Gly Gly Leu Ile Lys Ser Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Asp Gly Ser Ser Leu Tyr Phe Tyr Tyr Gly Met Asp
            100                 105                 110

Val Trp Gly Gln Gly Thr Thr Val Thr Val Ser Ser
        115                 120

<210> SEQ ID NO 89
<211> LENGTH: 372
<212> TYPE: DNA
<213> ORGANISM: Artificial Sequence
<220> FEATURE:
<223> OTHER INFORMATION: Synthetic: VH n.t. IP10.47

<400> SEQUENCE: 89
caagtgcagc tggtggagtc tgggggaggc gtggtccagc ctggggaggtc cctgagactc      60 tcctgtgcag cgtctggatt caccttcagt acccatggca tgcactgggt ccgccaggct     120
ccaggcaagg ggctggagtg ggtggcagtt ataggctttg gaggactgat taaatcctat     180
gcagactccg tgaagggccg attcaccatc tccagagaca attccaagaa cacgctgtat     240
ctgcaaatga acagcctgag agccgaggac acggctgtat attactgtgc gagagaaggt     300
gacggttcca gcctttattt ttactacggt atggacgtct ggggccaagg gaccacggtc     360
accgtctcct ca                                                         372

<210> SEQ ID NO 90
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.47

<400> SEQUENCE: 90

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Thr His
                20                  25                  30

Gly Met His Trp Val Arg Gln Ala Pro Gly Lys Gly Leu Glu Trp Val
            35                  40                  45

Ala Val Ile Gly Phe Gly Gly Leu Ile Lys Ser Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Asp Gly Ser Ser Leu Tyr Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
```

-continued

```
                145                 150                 155                 160
Val Thr Val Ser Trp Asn Ser Gly Ala Leu Thr Ser Gly Val His Thr
                    165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 91
<211> LENGTH: 12
<212> TYPE: PRT
<213> ORGANISM: Artificial Sequence
<220> FEATURE:
<223> OTHER INFORMATION: Synthetic: VL CDR1 a.a. IP10.47

<400> SEQUENCE: 91

Arg Ala Ser Gln Ser Val Ser Ser Ser Tyr Leu Ala
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Synthetic: VL CDR2 a.a.IP10.47
```

<400> SEQUENCE: 92

Gly Ala Ser Ser Arg Ala Thr
1               5

<210> SEQ ID NO 93
<211> LENGTH: 10
<212> TYPE: PRT
<213> ORGANISM: Artificial Sequence
<220> FEATURE:
<223> OTHER INFORMATION: Synthetic: VL CDR3 a.a. IP10.47

<400> SEQUENCE: 93

Gln Gln Tyr Gly Ser Ser Pro Ile Phe Thr
1               5                   10

<210> SEQ ID NO 94
<211> LENGTH: 109
<212> TYPE: PRT
<213> ORGANISM: Artificial Sequence
<220> FEATURE:
<223> OTHER INFORMATION: Synthetic: VL a.a. IP10.47

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 95
<211> LENGTH: 327
<212> TYPE: DNA
<213> ORGANISM: Artificial Sequence
<220> FEATURE:
<223> OTHER INFORMATION: Synthetic: VL n.t. IP10.47

<400> SEQUENCE: 95
gaaattgtgt tgacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327

<210> SEQ ID NO 96
<211> LENGTH: 216
<212> TYPE: PRT
<213> ORGANISM: Artificial Sequence
<220> FEATURE:
<223> OTHER INFORMATION: Synthetic: Full-length light chain a.a. IP10.47

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 97
<211> LENGTH: 5
<212> TYPE: PRT
<213> ORGANISM: Artificial Sequence
<220> FEATURE:
<223> OTHER INFORMATION: Synthetic: VH CDR1 a.a. IP10.48

<400> SEQUENCE: 97

Asn Tyr Gly Met His
1               5

<210> SEQ ID NO 98
<211> LENGTH: 17
<212> TYPE: PRT
<213> ORGANISM: Artificial Sequence
<220> FEATURE:
<223> OTHER INFORMATION: Synthetic: VH CDR2 a.a. IP10.48

<400> SEQUENCE: 98

Val Ile Asp Phe Ala Gly Ile Asn Lys Tyr Tyr Ala Asp Ser Val Lys
1               5                   10                  15

Gly

<210> SEQ ID NO 99
<211> LENGTH: 15
<212> TYPE: PRT
<213> ORGANISM: Artificial Sequence
<220> FEATURE:

<223> OTHER INFORMATION: Synthetic: VH CDR3 a.a. IP10.48

<400> SEQUENCE: 99

Glu Gly Glu Gly Ser Asn Ile Tyr Phe Phe Tyr Gly Met Asp Val
1               5                   10                  15

<210> SEQ ID NO 100
<211> LENGTH: 124
<212> TYPE: PRT
<213> ORGANISM: Artificial Sequence
<220> FEATURE:
<223> OTHER INFORMATION: Synthetic: VH a.a. IP10.48

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Asp Phe Ala Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Gly Ser Asn Ile Tyr Phe Phe Tyr Gly Met Asp
            100                 105                 110

Val Trp Gly Gln Gly Thr Thr Val Thr Val Ser Ser
        115                 120

<210> SEQ ID NO 101
<211> LENGTH: 372
<212> TYPE: DNA
<213> ORGANISM: Artificial Sequence
<220> FEATURE:
<223> OTHER INFORMATION: Synthetic: VH n.t. IP10.48

<400> SEQUENCE: 101
caagtgcagc tggtggagtc tgggggaggc gtggtccagc ctgggaggtc cctgagactc      60
tcctgtgcag cgtctggatt caccttcagt aactatggca tgcactgggt ccgccaggct    120
ccaggcaagg gctggagtg gtggcagtt atagattttg cgggaatcaa taaatactat     180
gcagactccg tgaagggccg attcaccatc tccagagaca attccaagaa cacgctgtat    240
ctgcaaatga acagcctgag agccgaggac acggctgtat attactgtgc gagagaagga    300
gaaggttcaa atatttattt cttttacggt atggacgtct ggggccaagg gaccacggtc    360
accgtctcct ca                                                         372

<210> SEQ ID NO 102
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.48

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr

-continued

```
                20                  25                  30
Gly Met His Trp Val Arg Gln Ala Pro Gly Lys Gly Leu Glu Trp Val
                35                  40                  45
Ala Val Ile Asp Phe Ala Gly Ile Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Glu Gly Glu Gly Ser Asn Ile Tyr Phe Phe Tyr Gly Met Asp
               100                 105                 110
Val Trp Gly Gln Gly Thr Thr Val Thr Val Ser Ser Ala Ser Thr Lys
               115                 120                 125
Gly Pro Ser Val Phe Pro Leu Ala Pro Ser Ser Lys Ser Thr Ser Gly
               130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
               165                 170                 175
Phe Pro Ala Val Leu Gln Ser Ser Gly Leu Tyr Ser Leu Ser Ser Val
               180                 185                 190
Val Thr Val Pro Ser Ser Ser Leu Gly Thr Gln Thr Tyr Ile Cys Asn
               195                 200                 205
Val Asn His Lys Pro Ser Asn Thr Lys Val Asp Lys Arg Val Glu Pro
               210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
               245                 250                 255
Thr Leu Met Ile Ser Arg Thr Pro Glu Val Thr Cys Val Val Val Asp
               260                 265                 270
Val Ser His Glu Asp Pro Glu Val Lys Phe Asn Trp Tyr Val Asp Gly
               275                 280                 285
Val Glu Val His Asn Ala Lys Thr Lys Pro Arg Glu Glu Gln Tyr Asn
               290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
               325                 330                 335
Ala Pro Ile Glu Lys Thr Ile Ser Lys Ala Lys Gly Gln Pro Arg Glu
               340                 345                 350
Pro Gln Val Tyr Thr Leu Pro Pro Ser Arg Glu Glu Met Thr Lys Asn
               355                 360                 365
Gln Val Ser Leu Thr Cys Leu Val Lys Gly Phe Tyr Pro Ser Asp Ile
               370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
               405                 410                 415
Leu Thr Val Asp Lys Ser Arg Trp Gln Gln Gly Asn Val Phe Ser Cys
               420                 425                 430
Ser Val Met His Glu Ala Leu His Asn His Tyr Thr Gln Lys Ser Leu
               435                 440                 445
```

<210> SEQ ID NO 103
<211> LENGTH: 12
<212> TYPE: PRT
<213> ORGANISM: Artificial Sequence
<220> FEATURE:
<223> OTHER INFORMATION: Synthetic: VL CDR1 a.a. IP10.48

<400> SEQUENCE: 103

Arg Ala Ser Gln Ser Val Ser Ser Ser Tyr Leu Ala
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Synthetic: VL CDR2 a.a.IP10.48

<400> SEQUENCE: 104

Gly Ala Ser Ser Arg Ala Thr
1               5

<210> SEQ ID NO 105
<211> LENGTH: 10
<212> TYPE: PRT
<213> ORGANISM: Artificial Sequence
<220> FEATURE:
<223> OTHER INFORMATION: Synthetic: VL CDR3 a.a. IP10.48

<400> SEQUENCE: 105

Gln Gln Tyr Gly Ser Ser Pro Ile Phe Thr
1               5                   10

<210> SEQ ID NO 106
<211> LENGTH: 109
<212> TYPE: PRT
<213> ORGANISM: Artificial Sequence
<220> FEATURE:
<223> OTHER INFORMATION: Synthetic: VL a.a. IP10.48

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 107
<211> LENGTH: 327
<212> TYPE: DNA
<213> ORGANISM: Artificial Sequence
<220> FEATURE:
<223> OTHER INFORMATION: Synthetic: VL n.t. IP10.48

<400> SEQUENCE: 107

```
gaaattgtgt tgacgcagtc tccaggcacc ctgtctttgt ctccagggga aagagccacc        60
ctctcctgca gggccagtca gagtgttagc agcagctatt tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcacctat attcactttc       300
ggccctggga ccaaagtgga tatcaaa                                           327
```

<210> SEQ ID NO 108
<211> LENGTH: 216
<212> TYPE: PRT
<213> ORGANISM: Artificial Sequence
<220> FEATURE:
<223> OTHER INFORMATION: Synthetic: Full-length light chain a.a. IP10.48

<400> SEQUENCE: 108

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 109
<211> LENGTH: 5
<212> TYPE: PRT
<213> ORGANISM: Artificial Sequence
<220> FEATURE:
<223> OTHER INFORMATION: Synthetic: VH CDR1 a.a. IP10.49

<400> SEQUENCE: 109

```
Gln Ser Gly Met His
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic: VH CDR2 a.a. IP10.49

<400> SEQUENCE: 110

Val Ile Gly Phe Gly Gly Leu Ile Lys Ser Tyr Ala Asp Ser Val Lys
1               5                   10                  15

Gly

<210> SEQ ID NO 111
<211> LENGTH: 15
<212> TYPE: PRT
<213> ORGANISM: Artificial Sequence
<220> FEATURE:
<223> OTHER INFORMATION: Synthetic: VH CDR3 a.a. IP10.49

<400> SEQUENCE: 111

Glu Gly Asp Gly Ser Gly Ile Tyr Tyr Tyr Gly Met Asp Val
1               5                   10                  15

<210> SEQ ID NO 112
<211> LENGTH: 124
<212> TYPE: PRT
<213> ORGANISM: Artificial Sequence
<220> FEATURE:
<223> OTHER INFORMATION: Synthetic: VH a.a. IP10.49

<400> SEQUENCE: 112

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gln Ser
            20                  25                  30

Gly Met His Trp Val Arg Gln Ala Pro Gly Lys Gly Leu Glu Trp Val
        35                  40                  45

Ala Val Ile Gly Phe Gly Gly Leu Ile Lys Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Gly Ser Gly Ile Tyr Tyr Tyr Gly Met Asp
            100                 105                 110

Val Trp Gly Gln Gly Thr Thr Val Thr Val Ser Ser
        115                 120

<210> SEQ ID NO 113
<211> LENGTH: 372
<212> TYPE: DNA
<213> ORGANISM: Artificial Sequence
<220> FEATURE:
<223> OTHER INFORMATION: Synthetic: VH n.t. IP10.49

<400> SEQUENCE: 113
caagtgcagc tggtggagtc tgggggaggc gtggtccagc ctggagggtc cctgagactc    60
tcctgtacag cgtctggatt caccttcagt cagagtggca tgcactgggt ccgccaggct   120
```

```
ccaggcaagg ggctggagtg ggtggcagtt atagggtttg gcggactgat taaaagctat    180
gcagactccg tgaagggccg attcaccatc tccagagaca attccaagaa cacgctgtat    240
ctgcaaatga acagcctgag agccgaggac acggctgtat attactgtgc gagagaaggg    300
gatggttcgg ggatttatta ctactacggt atggacgtct ggggccaagg gaccacggtc    360
accgtctcct ca                                                        372
```

\<210\> SEQ ID NO 114
\<211\> LENGTH: 454
\<212\> TYPE: PRT
\<213\> ORGANISM: Artificial Sequence
\<220\> FEATURE:
\<223\> OTHER INFORMATION: Synthetic: Full-length heavy chain a.a. IP10.49

\<400\> SEQUENCE: 114

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gln Ser
            20                  25                  30

Gly Met His Trp Val Arg Gln Ala Pro Gly Lys Gly Leu Glu Trp Val
        35                  40                  45

Ala Val Ile Gly Phe Gly Gly Leu Ile Lys Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Gly Ser Gly Ile Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

```
Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 115
<211> LENGTH: 12
<212> TYPE: PRT
<213> ORGANISM: Artificial Sequence
<220> FEATURE:
<223> OTHER INFORMATION: Synthetic: VL CDR1 a.a. IP10.49

<400> SEQUENCE: 115

Arg Ala Ser Gln Ser Val Ser Ser Ser Tyr Leu Ala
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Synthetic: VL CDR2 a.a.IP10.49

<400> SEQUENCE: 116

Gly Ala Ser Ser Arg Ala Thr
1               5

<210> SEQ ID NO 117
<211> LENGTH: 10
<212> TYPE: PRT
<213> ORGANISM: Artificial Sequence
<220> FEATURE:
<223> OTHER INFORMATION: Synthetic: VL CDR3 a.a. IP10.49

<400> SEQUENCE: 117

Gln Gln Tyr Gly Ser Ser Pro Ile Phe Thr
1               5                   10

<210> SEQ ID NO 118
<211> LENGTH: 109
<212> TYPE: PRT
<213> ORGANISM: Artificial Sequence
<220> FEATURE:
<223> OTHER INFORMATION: Synthetic: VL a.a. IP10.49

<400> SEQUENCE: 118

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105
```

<210> SEQ ID NO 119
<211> LENGTH: 327
<212> TYPE: DNA
<213> ORGANISM: Artificial Sequence
<220> FEATURE:
<223> OTHER INFORMATION: Synthetic: VL n.t. IP10.49

<400> SEQUENCE: 119

```
gaaattgtgt tgacgcagtc tccaggcacc ctgtctttgt ctccagggga aagagccacc    60
ctctcctgca gggccagtca gagtgttagc agcagctatt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctat attcactttc   300
ggccctggga ccaaagtgga tatcaaa                                        327
```

<210> SEQ ID NO 120
<211> LENGTH: 216
<212> TYPE: PRT
<213> ORGANISM: Artificial Sequence
<220> FEATURE:
<223> OTHER INFORMATION: Synthetic: Full-length light chain a.a. IP10.49

<400> SEQUENCE: 120

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
```

```
145                 150                 155                 160
Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 121
<211> LENGTH: 5
<212> TYPE: PRT
<213> ORGANISM: Artificial Sequence
<220> FEATURE:
<223> OTHER INFORMATION: Synthetic: VH CDR1 a.a. IP10.50

<400> SEQUENCE: 121

Arg Phe Gly Met His
1               5

<210> SEQ ID NO 122
<211> LENGTH: 17
<212> TYPE: PRT
<213> ORGANISM: Artificial Sequence
<220> FEATURE:
<223> OTHER INFORMATION: Synthetic: VH CDR2 a.a. IP10.50

<400> SEQUENCE: 122

Val Ile Gly Tyr Ala Gly Asp Asn Lys Tyr Tyr Ala Asp Ser Val Lys
1               5                   10                  15

Gly

<210> SEQ ID NO 123
<211> LENGTH: 15
<212> TYPE: PRT
<213> ORGANISM: Artificial Sequence
<220> FEATURE:
<223> OTHER INFORMATION: Synthetic: VH CDR3 a.a. IP10.50

<400> SEQUENCE: 123

Glu Gly Ala Gly Ser Asn Ile Tyr Tyr Tyr Gly Met Asp Val
1               5                   10                  15

<210> SEQ ID NO 124
<211> LENGTH: 124
<212> TYPE: PRT
<213> ORGANISM: Artificial Sequence
<220> FEATURE:
<223> OTHER INFORMATION: Synthetic: VH a.a. IP10.50

<400> SEQUENCE: 124

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Val Ile Gly Tyr Ala Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Glu Gly Ala Gly Ser Asn Ile Tyr Tyr Tyr Gly Met Asp
            100                 105                 110

Val Trp Gly Gln Gly Thr Thr Val Thr Val Ser Ser
        115                 120

<210> SEQ ID NO 125
<211> LENGTH: 372
<212> TYPE: DNA
<213> ORGANISM: Artificial Sequence
<220> FEATURE:
<223> OTHER INFORMATION: Synthetic: VH n.t. IP10.50

<400> SEQUENCE: 125
caagtgcagc tggtggagtc tgggggaggc gtggtccagc ctggagggtc cctgagactc      60
tcctgtgcag cgtctggatt caccttcagt cgattcggca tgcactgggt ccgccaggct     120
ccaggcaagg ggctggagtg ggtggcagtt atagggtacg cgggagacaa taaatattat     180
gcagactccg tgaagggccg attcaccatc tccagagaca attccaagaa cacgctgtat     240
ctgcaaatga acagcctgag agccgaggac acggctgtat attactgtgc gagagaaggg     300
gcaggttcga atatttatta ctactacggt atggacgtct ggggccaagg gaccacggtc     360
accgtctcct ca                                                        372

<210> SEQ ID NO 126
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.50

<400> SEQUENCE: 126

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Val Ile Gly Tyr Ala Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Asn Ile Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 127
<211> LENGTH: 12
<212> TYPE: PRT
<213> ORGANISM: Artificial Sequence
<220> FEATURE:
<223> OTHER INFORMATION: Synthetic: VL CDR1 a.a. IP10.50

<400> SEQUENCE: 127

Arg Ala Ser Gln Ser Val Ser Ser Ser Tyr Leu Ala
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Synthetic: VL CDR2 a.a.IP10.50

<400> SEQUENCE: 128

Gly Ala Ser Ser Arg Ala Thr
1               5

```
<210> SEQ ID NO 129
<211> LENGTH: 10
<212> TYPE: PRT
<213> ORGANISM: Artificial Sequence
<220> FEATURE:
<223> OTHER INFORMATION: Synthetic: VL CDR3 a.a. IP10.50

<400> SEQUENCE: 129

Gln Gln Tyr Gly Ser Ser Pro Ile Phe Thr
1               5                   10

<210> SEQ ID NO 130
<211> LENGTH: 109
<212> TYPE: PRT
<213> ORGANISM: Artificial Sequence
<220> FEATURE:
<223> OTHER INFORMATION: Synthetic: VL a.a. IP10.50

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 131
<211> LENGTH: 327
<212> TYPE: DNA
<213> ORGANISM: Artificial Sequence
<220> FEATURE:
<223> OTHER INFORMATION: Synthetic: VL n.t. IP10.50

<400> SEQUENCE: 131
gaaattgtgt tgacgcagtc tccaggcacc ctgtctttgt ctccagggga aagagccacc      60
ctctcctgca gggccagtca gagtgttagc agcagctatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctat attcactttc     300
ggccctggga ccaaagtgga tatcaaa                                         327

<210> SEQ ID NO 132
<211> LENGTH: 216
<212> TYPE: PRT
<213> ORGANISM: Artificial Sequence
<220> FEATURE:
<223> OTHER INFORMATION: Synthetic: Full-length light chain a.a. IP10.50

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                20              25              30
Tyr Leu Ala Trp Tyr Gln Gln Lys Pro Gly Gln Ala Pro Arg Leu Leu
            35              40              45

Ile Tyr Gly Ala Ser Ser Arg Ala Thr Gly Ile Pro Asp Arg Phe Ser
        50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Ser Ser Pro
                85              90              95

Ile Phe Thr Phe Gly Pro Gly Thr Lys Val Asp Ile Lys Arg Thr Val
            100             105             110

Ala Ala Pro Ser Val Phe Ile Phe Pro Pro Ser Asp Glu Gln Leu Lys
        115             120             125

Ser Gly Thr Ala Ser Val Val Cys Leu Leu Asn Asn Phe Tyr Pro Arg
    130             135             140

Glu Ala Lys Val Gln Trp Lys Val Asp Asn Ala Leu Gln Ser Gly Asn
145             150             155             160

Ser Gln Glu Ser Val Thr Glu Gln Asp Ser Lys Asp Ser Thr Tyr Ser
                165             170             175

Leu Ser Ser Thr Leu Thr Leu Ser Lys Ala Asp Tyr Glu Lys His Lys
            180             185             190

Val Tyr Ala Cys Glu Val Thr His Gln Gly Leu Ser Ser Pro Val Thr
        195             200             205

Lys Ser Phe Asn Arg Gly Glu Cys
    210             215

<210> SEQ ID NO 133
<211> LENGTH: 5
<212> TYPE: PRT
<213> ORGANISM: Artificial Sequence
<220> FEATURE:
<223> OTHER INFORMATION: Synthetic: VH CDR1 a.a. IP10.51

<400> SEQUENCE: 133

Asp Tyr Gly Met His
1               5

<210> SEQ ID NO 134
<211> LENGTH: 17
<212> TYPE: PRT
<213> ORGANISM: Artificial Sequence
<220> FEATURE:
<223> OTHER INFORMATION: Synthetic: VH CDR2 a.a. IP10.51

<400> SEQUENCE: 134

Val Ile Gly Tyr Gly Gly Leu Ile Lys Gly Tyr Ala Asp Ser Val Lys
1               5                   10                  15

Gly

<210> SEQ ID NO 135
<211> LENGTH: 15
<212> TYPE: PRT
<213> ORGANISM: Artificial Sequence
<220> FEATURE:
<223> OTHER INFORMATION: Synthetic: VH CDR3 a.a. IP10.51

<400> SEQUENCE: 135

Glu Gly Ala Gly Ser Ser Ile Tyr Tyr Tyr Gly Met Asp Val
1               5                   10                  15
```

<210> SEQ ID NO 136
<211> LENGTH: 124
<212> TYPE: PRT
<213> ORGANISM: Artificial Sequence
<220> FEATURE:
<223> OTHER INFORMATION: Synthetic: VH a.a. IP10.51

<400> SEQUENCE: 136

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Gly Tyr Gly Gly Leu Ile Lys Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Ser Ile Tyr Tyr Tyr Gly Met Asp
            100                 105                 110

Val Trp Gly Gln Gly Thr Thr Val Thr Val Ser Ser
        115                 120
```

<210> SEQ ID NO 137
<211> LENGTH: 372
<212> TYPE: DNA
<213> ORGANISM: Artificial Sequence
<220> FEATURE:
<223> OTHER INFORMATION: Synthetic: VH n.t. IP10.51

<400> SEQUENCE: 137

```
caagtgcagc tggtggagtc tgggggaggc gtggtccagc ctgggaggtc cctgagactc    60
tcctgtacag catctggatt caccttcagt gactacggca tgcactgggt ccgccaggct   120
ccaggcaagg ggctggagtg ggtggcagtt atagggtacg gcggactgat taaggatat    180 gcagactccg tgaagggccg attcaccatc tccagagaca attccaagaa cacgctgtat   240
ctgcaaatga acagcctgag agccgaggac acggctgtat attactgtgc gagagaaggg   300
gcaggttcga gtatatatta ctactacggt atggacgtct ggggccaagg gaccacggtc   360
accgtctcct ca                                                      372
```

<210> SEQ ID NO 138
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.51

<400> SEQUENCE: 138

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Gly Tyr Gly Gly Leu Ile Lys Gly Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Ala Gly Ser Ser Ile Tyr Tyr Tyr Gly Met Asp
        100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 139
<211> LENGTH: 12

```
<212> TYPE: PRT
<213> ORGANISM: Artificial Sequence
<220> FEATURE:
<223> OTHER INFORMATION: Synthetic: VL CDR1 a.a. IP10.51

<400> SEQUENCE: 139

Arg Ala Ser Gln Ser Val Ser Ser Ser Tyr Leu Ala
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Synthetic: VL CDR2 a.a.IP10.51

<400> SEQUENCE: 140

Gly Ala Ser Ser Arg Ala Thr
1               5

<210> SEQ ID NO 141
<211> LENGTH: 10
<212> TYPE: PRT
<213> ORGANISM: Artificial Sequence
<220> FEATURE:
<223> OTHER INFORMATION: Synthetic: VL CDR3 a.a. IP10.51

<400> SEQUENCE: 141

Gln Gln Tyr Gly Ser Ser Pro Ile Phe Thr
1               5                   10

<210> SEQ ID NO 142
<211> LENGTH: 109
<212> TYPE: PRT
<213> ORGANISM: Artificial Sequence
<220> FEATURE:
<223> OTHER INFORMATION: Synthetic: VL a.a. IP10.51

<400> SEQUENCE: 142

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 143
<211> LENGTH: 327
<212> TYPE: DNA
<213> ORGANISM: Artificial Sequence
<220> FEATURE:
<223> OTHER INFORMATION: Synthetic: VL n.t. IP10.51

<400> SEQUENCE: 143
gaaattgtgt tgacgcagtc tccaggcacc ctgtctttgt ctccagggga aagagccacc    60
```

```
ctctcctgca gggccagtca gagtgttagc agcagctatt tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctat attcactttc    300
ggccctggga ccaaagtgga tatcaaa                                        327
```

<210> SEQ ID NO 144
<211> LENGTH: 216
<212> TYPE: PRT
<213> ORGANISM: Artificial Sequence
<220> FEATURE:
<223> OTHER INFORMATION: Synthetic: Full-length light chain a.a. IP10.51

<400> SEQUENCE: 144

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 145
<211> LENGTH: 5
<212> TYPE: PRT
<213> ORGANISM: Artificial Sequence
<220> FEATURE:
<223> OTHER INFORMATION: Synthetic: VH CDR1 a.a. IP10.54

<400> SEQUENCE: 145

```
Gln Tyr Gly Met His
1               5
```

<210> SEQ ID NO 146
<211> LENGTH: 17
<212> TYPE: PRT

<213> ORGANISM: Artificial Sequence
<220> FEATURE:
<223> OTHER INFORMATION: Synthetic: VH CDR2 a.a. IP10.54

<400> SEQUENCE: 146

Val Ile Ser Tyr Gly Gly Asp Ile Lys Tyr Tyr Ala Asp Ser Val Lys
1               5                   10                  15
Gly

<210> SEQ ID NO 147
<211> LENGTH: 15
<212> TYPE: PRT
<213> ORGANISM: Artificial Sequence
<220> FEATURE:
<223> OTHER INFORMATION: Synthetic: VH CDR3 a.a. IP10.54

<400> SEQUENCE: 147

Glu Gly Glu Gly Ser Asn Ile Tyr Tyr Tyr Gly Met Asp Val
1               5                   10                  15

<210> SEQ ID NO 148
<211> LENGTH: 124
<212> TYPE: PRT
<213> ORGANISM: Artificial Sequence
<220> FEATURE:
<223> OTHER INFORMATION: Synthetic: VH a.a. IP10.54

<400> SEQUENCE: 148

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Gln Tyr
            20                  25                  30

Gly Met His Trp Val Arg Gln Ala Pro Gly Lys Gly Leu Glu Trp Val
        35                  40                  45

Ala Val Ile Ser Tyr Gly Gly Asp Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Ile Tyr Tyr Cys
                85                  90                  95

Ala Arg Glu Gly Glu Gly Ser Asn Ile Tyr Tyr Tyr Gly Met Asp
            100                 105                 110

Val Trp Gly Gln Gly Thr Thr Val Thr Val Ser Ser
        115                 120

<210> SEQ ID NO 149
<211> LENGTH: 372
<212> TYPE: DNA
<213> ORGANISM: Artificial Sequence
<220> FEATURE:
<223> OTHER INFORMATION: Synthetic: VH n.t. IP10.54

<400> SEQUENCE: 149
caagtgcagc tggtggagtc tgggggaggc gtggtccagc ctggaggtc cctgagactc       60 tcctgtacag cgtctggatt caccttcagt cagtatggca tgcactgggt ccgccaggct     120
ccaggcaagg ggctggagtg ggtggcagtt atatcgtatg gtggagacat caaatactat     180
gcagactccg taaagggccg attcaccatc tccagagaca attccaaaaa cacgctgtat     240
ctggaaatga acagcctgag agccgaggac acggctatat attactgtgc gagagaaggg     300
gagggttcta atatatatta ctactacggt atggacgtct ggggccaagg gaccacggtc     360
accgtctcct ca                                                          372

<210> SEQ ID NO 150
<211> LENGTH: 454
<212> TYPE: PRT
<213> ORGANISM: Artificial Sequence
<220> FEATURE:
<223> OTHER INFORMATION: Synthetic: Full-length heavy chain a.a. IP10.54

<400> SEQUENCE: 150

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gln Tyr
            20                  25                  30

Gly Met His Trp Val Arg Gln Ala Pro Gly Lys Gly Leu Glu Trp Val
        35                  40                  45

Ala Val Ile Ser Tyr Gly Gly Asp Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Ile Tyr Tyr Cys
                85                  90                  95

Ala Arg Glu Gly Glu Gly Ser Asn Ile Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

-continued

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 151
<211> LENGTH: 12
<212> TYPE: PRT
<213> ORGANISM: Artificial Sequence
<220> FEATURE:
<223> OTHER INFORMATION: Synthetic: VL CDR1 a.a. IP10.54

<400> SEQUENCE: 151

Arg Ala Ser Gln Ser Val Ser Ser Ser Tyr Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Synthetic: VL CDR2 a.a.IP10.54

<400> SEQUENCE: 152

Gly Ala Ser Ser Arg Ala Thr
1               5

<210> SEQ ID NO 153
<211> LENGTH: 10
<212> TYPE: PRT
<213> ORGANISM: Artificial Sequence
<220> FEATURE:
<223> OTHER INFORMATION: Synthetic: VL CDR3 a.a. IP10.54

<400> SEQUENCE: 153

Gln Gln Tyr Gly Ser Ser Pro Ile Phe Thr
1               5                   10

<210> SEQ ID NO 154
<211> LENGTH: 109
<212> TYPE: PRT
<213> ORGANISM: Artificial Sequence
<220> FEATURE:
<223> OTHER INFORMATION: Synthetic: VL a.a. IP10.54

<400> SEQUENCE: 154

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
         50                   55                  60

Gly Ser Gly Ser Gly Thr Asp Phe Thr Leu Thr Ile Ser Arg Leu Glu
65                   70                  75                  80

Pro Glu Asp Phe Ala Val Tyr Tyr Cys Gln Gln Tyr Gly Ser Ser Pro
                    85                  90                  95

Ile Phe Thr Phe Gly Pro Gly Thr Lys Val Asp Ile Lys
                100                 105
```

<210> SEQ ID NO 155
<211> LENGTH: 327
<212> TYPE: DNA
<213> ORGANISM: Artificial Sequence
<220> FEATURE:
<223> OTHER INFORMATION: Synthetic: VL n.t. IP10.54

<400> SEQUENCE: 155

```
gaaattgtgt tgacgcagtc tccaggcacc ctgtctttgt ctccagggga aagagccacc        60
ctctcctgca gggccagtca gagtgttagc agcagctatt tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcacctat attcactttc       300
ggccctggga ccaaagtgga tatcaaa                                          327
```

<210> SEQ ID NO 156
<211> LENGTH: 216
<212> TYPE: PRT
<213> ORGANISM: Artificial Sequence
<220> FEATURE:
<223> OTHER INFORMATION: Synthetic: Full-length light chain a.a. IP10.54

<400> SEQUENCE: 156

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
         50                   55                  60

Gly Ser Gly Ser Gly Thr Asp Phe Thr Leu Thr Ile Ser Arg Leu Glu
65                   70                  75                  80

Pro Glu Asp Phe Ala Val Tyr Tyr Cys Gln Gln Tyr Gly Ser Ser Pro
                    85                  90                  95

Ile Phe Thr Phe Gly Pro Gly Thr Lys Val Asp Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190
```

```
Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 157
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: Human IP-10 a.a.

<400> SEQUENCE: 157

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 158
<211> LENGTH: 368
<212> TYPE: PRT
<213> ORGANISM: Homo sapiens
<220> FEATURE:
<221> NAME/KEY: misc_feature
<222> LOCATION: (1)..(368)
<223> OTHER INFORMATION: Human CXCR3 a.a.

<400> SEQUENCE: 158

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
130                 135                 140

Ile Ser Phe Asp Arg Tyr Leu Asn Ile Val His Ala Thr Gln Leu Tyr
```

```
            145                 150                 155                 160
    Arg Arg Gly Pro Pro Ala Arg Val Thr Leu Thr Cys Leu Ala Val Trp
                    165                 170                 175

Gly Leu Cys Leu Leu Phe Ala Leu Pro Asp Phe Ile Phe Leu Ser Ala
                    180                 185                 190

His His Asp Glu Arg Leu Asn Ala Thr His Cys Gln Tyr Asn Phe Pro
                    195                 200                 205

Gln Val Gly Arg Thr Ala Leu Arg Val Leu Gln Leu Val Ala Gly Phe
                    210                 215                 220

Leu Leu Pro Leu Leu Val Met Ala Tyr Cys Tyr Ala His Ile Leu Ala
    225                 230                 235                 240

Val Leu Leu Val Ser Arg Gly Gln Arg Arg Leu Arg Ala Met Arg Leu
                    245                 250                 255

Val Val Val Val Val Ala Phe Ala Leu Cys Trp Thr Pro Tyr His
                    260                 265                 270

Leu Val Val Leu Val Asp Ile Leu Met Asp Leu Gly Ala Leu Ala Arg
                    275                 280                 285

Asn Cys Gly Arg Glu Ser Arg Val Asp Val Ala Lys Ser Val Thr Ser
                    290                 295                 300

Gly Leu Gly Tyr Met His Cys Cys Leu Asn Pro Leu Leu Tyr Ala Phe
    305                 310                 315                 320

Val Gly Val Lys Phe Arg Glu Arg Met Trp Met Leu Leu Leu Arg Leu
                    325                 330                 335

Gly Cys Pro Asn Gln Arg Gly Leu Gln Arg Gln Pro Ser Ser Ser Arg
                    340                 345                 350

Arg Asp Ser Ser Trp Ser Glu Thr Ser Glu Ala Ser Tyr Ser Gly Leu
                    355                 360                 365

<210> SEQ ID NO 159
<211> LENGTH: 98
<212> TYPE: PRT
<213> ORGANISM: Macaca mulatta
<220> FEATURE:
<221> NAME/KEY: misc_feature
<222> LOCATION: (1)..(98)
<223> OTHER INFORMATION: Rhesus monkey IP-10 a.a.

<400> SEQUENCE: 159

Met Asn Gln Thr Ala Ile Leu Ile Cys Cys Leu Val Phe Leu Thr Leu
    1               5                   10                  15

Ser Gly Ile Gln Gly Ile Pro Leu Ser Arg Thr Val Arg Cys Thr Cys
                    20                  25                  30

Ile Ser Ile Ser Asn Gln Pro Val Asn Pro Arg Ser Leu Glu Lys Leu
                    35                  40                  45

Glu Ile Ile Pro Pro Ser Gln Phe Cys Pro His Val Glu Ile Ile Ala
                    50                  55                  60

Thr Met Lys Lys Lys Gly Glu Lys Arg Cys Leu Asn Pro Glu Ser Lys
    65                  70                  75                  80

Ala Ile Lys Asn Leu Leu Lys Ala Val Ser Lys Glu Arg Ser Lys Arg
                    85                  90                  95

Ser Pro

<210> SEQ ID NO 160
<211> LENGTH: 98
<212> TYPE: PRT
<213> ORGANISM: Mus musculus
<220> FEATURE:
```

<221> NAME/KEY: misc_feature
<222> LOCATION: (1)..(98)
<223> OTHER INFORMATION: Mouse IP-10

<400> SEQUENCE: 160

Met Asn Pro Ser Ala Ala Val Ile Phe Cys Leu Ile Leu Leu Gly Leu
1               5                   10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
        35                  40                  45

Glu Ile Ile Pro Ala Ser Leu Ser Cys Pro Arg Val Glu Ile Ile Ala
50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro

<210> SEQ ID NO 161
<211> LENGTH: 125
<212> TYPE: PRT
<213> ORGANISM: Homo sapiens
<220> FEATURE:
<221> NAME/KEY: misc_feature
<222> LOCATION: (1)..(125)
<223> OTHER INFORMATION: Human MIG a.a.

<400> SEQUENCE: 161

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125

<210> SEQ ID NO 162
<211> LENGTH: 94
<212> TYPE: PRT
<213> ORGANISM: Homo sapiens
<220> FEATURE:
<221> NAME/KEY: misc_feature
<222> LOCATION: (1)..(94)
<223> OTHER INFORMATION: Human ITAC a.a.a

<400> SEQUENCE: 162

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

```
Ile Gly Pro Gly Val Lys Ala Val Lys Val Ala Asp Ile Glu Lys Ala
            35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 163
<211> LENGTH: 6
<212> TYPE: PRT
<213> ORGANISM: Artificial Sequence
<220> FEATURE:
<223> OTHER INFORMATION: Synthetic: Epitope Peptide 1

<400> SEQUENCE: 163

Ser Ile Ser Asn Gln Pro
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic: Epitope Peptide 2

<400> SEQUENCE: 164

Val Asn Pro Arg Ser Leu Glu Lys Leu
1               5

<210> SEQ ID NO 165
<211> LENGTH: 15
<212> TYPE: PRT
<213> ORGANISM: Artificial Sequence
<220> FEATURE:
<223> OTHER INFORMATION: Synthetic: Epitope Peptide 3

<400> SEQUENCE: 165

Ile Ile Pro Ala Ser Gln Phe Cys Pro Arg Val Glu Ile Ile Ala
1               5                   10                  15

<210> SEQ ID NO 166
<211> LENGTH: 124
<212> TYPE: PRT
<213> ORGANISM: Artificial Sequence
<220> FEATURE:
<223> OTHER INFORMATION: Synthetic: VH a.a. consensus all Abs
<220> FEATURE:
<221> NAME/KEY: misc_feature
<222> LOCATION: (23)..(23)
<223> OTHER INFORMATION: X can be T or A
<220> FEATURE:
<221> NAME/KEY: misc_feature
<222> LOCATION: (31)..(31)
<223> OTHER INFORMATION: X can be S or E or K or Q or T or N or R or D
<220> FEATURE:
<221> NAME/KEY: misc_feature
<222> LOCATION: (32)..(32)
<223> OTHER INFORMATION: X can be Y or H or S or F
<220> FEATURE:
<221> NAME/KEY: misc_feature
<222> LOCATION: (52)..(52)
<223> OTHER INFORMATION: X can be D or G or S
<220> FEATURE:
<221> NAME/KEY: misc_feature
<222> LOCATION: (53)..(53)
<223> OTHER INFORMATION: X can be  F or Y or H
```

```
<220> FEATURE:
<221> NAME/KEY: misc_feature
<222> LOCATION: (54)..(54)
<223> OTHER INFORMATION: X can be  V or A or G or N
<220> FEATURE:
<221> NAME/KEY: misc_feature
<222> LOCATION: (56)..(56)
<223> OTHER INFORMATION: X can be D or L or V or I or A
<220> FEATURE:
<221> NAME/KEY: misc_feature
<222> LOCATION: (57)..(57)
<223> OTHER INFORMATION: X can be T or I or N
<220> FEATURE:
<221> NAME/KEY: misc_feature
<222> LOCATION: (59)..(59)
<223> OTHER INFORMATION: X can be Y or G or S
<220> FEATURE:
<221> NAME/KEY: misc_feature
<222> LOCATION: (61)..(61)
<223> OTHER INFORMATION: X can be T or A
<220> FEATURE:
<221> NAME/KEY: misc_feature
<222> LOCATION: (82)..(82)
<223> OTHER INFORMATION: X can be Q or E
<220> FEATURE:
<221> NAME/KEY: misc_feature
<222> LOCATION: (93)..(93)
<223> OTHER INFORMATION: X can be V or I
<220> FEATURE:
<221> NAME/KEY: misc_feature
<222> LOCATION: (101)..(101)
<223> OTHER INFORMATION: X can be A or E or D
<220> FEATURE:
<221> NAME/KEY: misc_feature
<222> LOCATION: (104)..(14)
<223> OTHER INFORMATION: X can be N or S or G
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: X can be I or L or V
<220> FEATURE:
<221> NAME/KEY: misc_feature
<222> LOCATION: (107)..(107)
<223> OTHER INFORMATION: X can be Y or F
<220> FEATURE:
<221> NAME/KEY: misc_feature
<222> LOCATION: (108)..(108)
<223> OTHER INFORMATION: X can be Y or F

<400> SEQUENCE: 166

Gln Val Gln Leu Val Glu Ser Gly Gly Gly Val Val Gln Pro Gly Arg
1               5                   10                  15

Ser Leu Arg Leu Ser Cys Xaa Ala Ser Gly Phe Thr Phe Ser Xaa Xaa
            20                  25                  30

Gly Met His Trp Val Arg Gln Ala Pro Gly Lys Gly Leu Glu Trp Val
        35                  40                  45

Ala Val Ile Xaa Xaa Xaa Gly Xaa Xaa Lys Xaa Tyr Xaa Asp Ser Val
    50                  55                  60

Lys Gly Arg Phe Thr Ile Ser Arg Asp Asn Ser Lys Asn Thr Leu Tyr
65                  70                  75                  80

Leu Xaa Met Asn Ser Leu Arg Ala Glu Asp Thr Ala Xaa Tyr Tyr Cys
            85                  90                  95

Ala Arg Glu Gly Xaa Gly Ser Xaa Xaa Tyr Xaa Xaa Tyr Gly Met Asp
            100                 105                 110

Val Trp Gly Gln Gly Thr Thr Val Thr Val Ser Ser
        115                 120
```

```
<210> SEQ ID NO 167
<211> LENGTH: 124
<212> TYPE: PRT
<213> ORGANISM: Artificial Sequence
<220> FEATURE:
<223> OTHER INFORMATION: Synthetic: VH a.a. consensus Abs IP10.44,
      IP10.45, IP10.46, IP10.52, and IP10.53
<220> FEATURE:
<221> NAME/KEY: misc_feature
<222> LOCATION: (23)..(23)
<223> OTHER INFORMATION: X can be T or  A
<220> FEATURE:
<221> NAME/KEY: misc_feature
<222> LOCATION: (31)..(31)
<223> OTHER INFORMATION: X can be E or  K or  Q or   D
<220> FEATURE:
<221> NAME/KEY: misc_feature
<222> LOCATION: (32)..(32)
<223> OTHER INFORMATION: X can be Y or  H
<220> FEATURE:
<221> NAME/KEY: misc_feature
<222> LOCATION: (52)..(52)
<223> OTHER INFORMATION: X can be G or  S
<220> FEATURE:
<221> NAME/KEY: misc_feature
<222> LOCATION: (53)..(53)
<223> OTHER INFORMATION: X can be F or  Y or  H
<220> FEATURE:
<221> NAME/KEY: misc_feature
<222> LOCATION: (54)..(54)
<223> OTHER INFORMATION: X can be A or  G or  N
<220> FEATURE:
<221> NAME/KEY: misc_feature
<222> LOCATION: (56)..(56)
<223> OTHER INFORMATION: X can be D or  L or  V or  A
<220> FEATURE:
<221> NAME/KEY: misc_feature
<222> LOCATION: (59)..(59)
<223> OTHER INFORMATION: X can be Y or  G or  S
<220> FEATURE:
<221> NAME/KEY: misc_feature
<222> LOCATION: (101)..(101)
<223> OTHER INFORMATION: X can be A or  E
<220> FEATURE:
<221> NAME/KEY: misc_feature
<222> LOCATION: (104)..(104)
<223> OTHER INFORMATION: X can be N or  S
<220> FEATURE:
<221> NAME/KEY: misc_feature
<222> LOCATION: (105)..(105)
<223> OTHER INFORMATION: X can be I or  V
<220> FEATURE:
<221> NAME/KEY: misc_feature
<222> LOCATION: (107)..(107)
<223> OTHER INFORMATION: X can be Y or  F

<400> SEQUENCE: 167

Gln Val Gln Leu Val Glu Ser Gly Gly Gly Val Val Gln Pro Gly Arg
1               5                   10                  15

Ser Leu Arg Leu Ser Cys Xaa Ala Ser Gly Phe Thr Phe Ser Xaa Xaa
                20                  25                  30

Gly Met His Trp Val Arg Gln Ala Pro Gly Lys Gly Leu Glu Trp Val
            35                  40                  45

Ala Val Ile Xaa Xaa Xaa Gly Xaa Ile Lys Xaa Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Xaa Gly Ser Xaa Xaa Tyr Xaa Tyr Tyr Gly Met Asp
            100                 105                 110
```

```
Val Trp Gly Gln Gly Thr Thr Val Thr Val Ser Ser
        115                 120

<210> SEQ ID NO 168
<211> LENGTH: 124
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: X can be T or  A
<220> FEATURE:
<221> NAME/KEY: misc_feature
<222> LOCATION: (31)..(31)
<223> OTHER INFORMATION: X can be E or  D
<220> FEATURE:
<221> NAME/KEY: misc_feature
<222> LOCATION: (53)..(53)
<223> OTHER INFORMATION: X can be F or  Y
<220> FEATURE:
<221> NAME/KEY: misc_feature
<222> LOCATION: (54)..(54)
<223> OTHER INFORMATION: X can be A or  G
<220> FEATURE:
<221> NAME/KEY: misc_feature
<222> LOCATION: (104)..(104)
<223> OTHER INFORMATION: X can be N or  S
<220> FEATURE:
<221> NAME/KEY: misc_feature
<222> LOCATION: (105)..(105)
<223> OTHER INFORMATION: X can be I or  V

<400> SEQUENCE: 168

Gln Val Gln Leu Val Glu Ser Gly Gly Val Val Gln Pro Gly Arg
1               5                   10                  15

Ser Leu Arg Leu Ser Cys Xaa Ala Ser Gly Phe Thr Phe Ser Xaa Tyr
            20                  25                  30

Gly Met His Trp Val Arg Gln Ala Pro Gly Lys Gly Leu Glu Trp Val
        35                  40                  45

Ala Val Ile Gly Xaa Xaa Gly Leu Ile Lys Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Gly Ser Xaa Xaa Tyr Tyr Tyr Gly Met Asp
            100                 105                 110

Val Trp Gly Gln Gly Thr Thr Val Thr Val Ser Ser
        115                 120
```

IP-10 ANTIBODIES AND THEIR USES

RELATED APPLICATIONS

This application is a divisional of U.S. application Ser. No. 15/364,612, filed on Nov. 30, 2016 (allowed), which claims priority to U.S. Provisional Application No. 62/374,622, filed on Aug. 12, 2016 and U.S. Provisional Provisional Application No. 62/261,210, filed on Nov. 30, 2015, the contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Feb. 8, 2017, is named MXI-541 Sequence Listing.txt and is 156,454 bytes in size.

BACKGROUND OF THE INVENTION

Interferon gamma inducible protein 10 (IP-10) (also known as CXCL10) is a 10 kDa chemokine that was originally identified based on expression of the IP-10 gene in cells treated with interferon gamma (IFN-gamma) (Luster, A. D. et al. (1985) *Nature* 315:672-676). IP-10 shows homology to proteins having chemotactic activity, such as platelet factor 4 and beta-thromoboglobulin, and to proteins having mitogenic activity, such as connective tissue-activating peptide III (Luster, A. D. et al. (1987) *Proc. Natl. Acad. Sci. USA* 84:2868-2871). IP-10 is secreted by a variety of cells, including endothelial cells, monocytes, fibroblasts, and keratinocytes, in response to IFN-gamma (Luster, A. D. and Ravetch, J. V. (1987) *J. Exp. Med.* 166:1084-1097). IP-10 also has been shown to be present in dermal macrophages and endothelial cells in delayed type hypersensitivity (DTH) responses in human skin (Kaplan, G. et al. (1987) *J. Exp. Med.* 166:1098-1108). Although originally identified based on its being induced by IFN-gamma, IP-10 also can be induced by IFN-alpha, for example in dendritic cells (Padovan, E. et al. (2002) *J. Leukoc. Biol.* 71:669-676). IP-10 expression can also be induced in cells of the central nervous system, such as astrocytes and microglia, by stimuli such as IFN-gamma, viruses and lipopolysaccharide (Vanguri, R. and Farber, J. M. (1994) *J. Immunol.* 152:1411-1418; Ren, L. Q. et al. (1998) *Brain Res. Mol. Brain Res.* 59:256-263). The immunobiology of IP-10 is reviewed in Neville, L. F et al. (1997) *Cytokine Growth Factor Rev.* 8:207-219.

The receptor for IP-10 has been identified as CXCR3, a seven transmembrane receptor (Loetscher, M. et al. (1996) *J. Exp. Med.* 184:963-969). CXCR3 has been shown to be expressed on activated T lymphocytes but not on resting T lymphocytes, nor on B lymphocytes, monocytes or granulocytes (Loetscher, M. et al., supra). CXCR3 expression has been shown to be upregulated on NK cells by stimulation with TGF-beta 1 (Inngjerdingen, M. et al. (2001) *Blood* 97:367-375). Two other ligands for CXCR3 have also been identified: MIG (Loetscher, M. et al., supra) and ITAC (Cole, K. E. et al. (1998) *J. Exp. Med.* 187:2009-2021).

Binding of IP-10 to CXCR3 has been shown to mediate calcium mobilization and chemotaxis in activated T cells (Loetscher, M. et al., supra). Chemotaxis and intracellular calcium mobilization are also induced by IP-10 binding to CXCR3 on activated NK cells (Maghazachi, A. A. et al. (1997) *FASEB J.* 11:765-774). Within the thymus, IP-10 has been shown to be a chemoattractant for TCRαβ+ CD8+ T cells, TCRαβ+ T cells and NK-type cells (Romagnani, P. et al. (2001) *Blood* 97:601-607).

IP-10 or its receptor CXCR3 have been identified in a variety of different inflammatory and autoimmune conditions, including multiple sclerosis (see e.g., Sorensen, T. L. et al. (1999) *J. Clin. Invest.* 103:807-815), rheumatoid arthritis (see e.g., Patel, D. D. et al. (2001) *Clin. Immunol.* 98:39-45), ulcerative colitis (see e.g., Uguccioni, M. et al. (1999) *Am. J. Pathol.* 155:331-336), hepatitis (see e.g., Narumi, S. et al. (1997) *J. Immunol.* 158:5536-5544), spinal cord injury (see e.g., McTigue, D. M. et al. (1998) *J. Neurosci. Res.* 53:368-376; Gonzalez et al. 2003. *Exp. Neurol.* 184:456-463), systemic lupus erythematosus (see e.g., Narumi, S. et al. (2000) *Cytokine* 12:1561-1565), transplant rejection (see e.g., Zhang, Z. et al. (2002) *J. Immunol.* 168:3205-3212), Sjogren's syndrome (see e.g., Ogawa, N. et al. (2002) *Arthritis Rheum.* 46:2730-2741).

Antibodies which bind to IP-10 for treating such conditions are known in the art, e.g., as described in WO2005/058815. However, the need exists for improved therapeutic agents (e.g., antibodies) that inhibit the activity of IP-10, in particular agents that are suitable for use in humans.

SUMMARY OF THE INVENTION

The present invention provides isolated monoclonal antibodies (e.g., human monoclonal antibodies) that bind Interferon gamma inducible protein 10 (IP-10) (also known as CXCL10), e.g., human IP-10, and have optimized physical stability and improved functional features compared to previously described anti-IP-10 antibodies. In particular, the invention relates to a modified form of antibody IP10.1 (WO 2005/058815, also referred to as antibody 6A5), which exhibits significantly improved stability and activity compared to the unmodified antibody. Specifically, by altering the heavy chain CDR domains of antibody IP10.1 it was shown that the modified antibody exhibited higher thermal stability and thermal reversibility (e.g., higher thermal stability and thermal reversibility with first melting temperature at 70.2° C. (TM1 for IP10.1 at 64° C.) and thermal reversibility of 41.2% at 73° C. At the same time, it was unexpectedly observed that the modified antibody exhibited at least a 50-fold improvement in binding affinity to human IP-10, as well as improvement in other functional features compared to the unmodified antibody, including, e.g., at least a 5-fold increase in blocking exogenous IP-10 binding to its target cells (such as CXCR3-expressing cells (CXCR3/300.19) and gut epithelial cells (KM12SM)), at least 6-fold increase in inhibiting endogenous IP-10-mediated IL-6 secretion by hPBMCs stimulated with IFNα/γ, at least 4-fold greater potency in inhibiting endogenous IP-10-mediated IL-12p40 secretion by hPBMCs stimulated with IFNγ/LPS, and at least 150-fold greater potency in terms of Pharmacokinetic/Pharmacodynamic (PK/PD) modeling. Other improved functional features exhibited by the modified antibodies described herein compared to their unmodified counterparts include:

(a) increased (e.g., at least 4-fold better) potency in inhibiting endogenous IP-10-mediated IL-12p40 secretion by hPBMCs;

(b) increased inhibition of IL-6 and IL-12p40 in blood (colitis model);

(c) increased suppression of free IP-10, e.g., up to 10 days;

(d) reduced human CXCR3+NK cell frequency in mouse spleens;

(e) increased (e.g., at least 8-fold better) potency in inhibiting mouse IP-10-induced calcium flux in CXCR3/300.19 cells;

(f) increased reduction in circulating levels of cytokines; and/or (g) increased (e.g., at least 2-fold better) body serum clearance (CLT).

In addition, the modified antibodies (like antibody IP10.1) lack substantial cross-reactivity with either human MIG, human ITAC or mouse IP-10. The combined increase in stability and binding/biological activity of the modified antibodies was surprising, particularly in view of the criticality of CDRs regions to antibody function.

Accordingly, the antibodies of the present invention exhibit improved physical properties (i.e., thermal and chemical stability) compared to antibody IP10.1, as well as improved functional features (e.g., binding affinity for human IP-10 and potency).

In a particular embodiment, the isolated monoclonal antibody (e.g., a human antibody), or an antigen-binding portion thereof, comprises heavy and light chain variable regions, wherein the heavy chain CDR1, CDR2, and CDR3 regions are from the heavy chain variable region of SEQ ID NOs: 16, 28, 40, 52, 64, 76, 88, 100, 112, 124, 136, or 148, such as the CDR1, CDR2, and CDR3 sequences from SEQ ID NO: 16 (e.g., as set forth in SEQ ID NOs: 13, 14, and 15, respectively).

In another embodiment, the light chain CDR1, CDR2, and CDR3 regions are from the light chain variable region of SEQ ID NOs: 22, 34, 46, 58, 70, 82, 94, 106, 118, 130, 142, or 154, such as the CDR1, CDR2, and CDR3 sequences from SEQ ID NO: 22 (e.g., as set forth in SEQ ID NOs: 19, 20, and 21, respectively).

In yet another embodiment, the heavy chain variable region comprises the amino acid sequence of SEQ ID NO: 16, 28, 40, 52, 64, 76, 88, 100, 112, 124, 136, or 148, and/or the light chain variable region comprises the amino acid sequence of SEQ ID NO: 22, 34, 46, 58, 70, 82, 94, 106, 118, 130, 142, or 154 (e.g., the amino acid sequence of SEQ ID NO: 16 and/or 22), or sequences having at least 95% amino acid identity to SEQ ID NOs: 16, 28, 40, 52, 64, 76, 88, 100, 112, 124, 136, or 148, and/or SEQ ID NO: 22, 34, 46, 58, 70, 82, 94, 106, 118, 130, 142, or 154 (e.g., sequences having at least 95% amino acid identity to SEQ ID NO: 16 and/or 22, respectively). Alternatively, the heavy chain variable region comprises the consensus amino acid sequence as set forth in SEQ ID NO: 166, 167, or 168.

In another embodiment, the heavy and light chain CDR1, CDR2, and CDR3 regions comprise the following amino acid sequences, respectively:

(a) SEQ ID NOs: 13, 14, and 15 and SEQ ID NOs: 19, 20, and 21;

(b) SEQ ID NOs: 25, 26, and 27 and SEQ ID NOs: 31, 32, and 33;

(c) SEQ ID NOs: 37, 38, and 39 and SEQ ID NOs: 43, 44, and 45;

(d) SEQ ID NOs: 49, 50, and 51 and SEQ ID NOs: 55, 56, and 57;

(e) SEQ ID NOs: 61, 62, and 63 and SEQ ID NOs: 67, 68, and 69;

(f) SEQ ID NOs: 73, 74, and 75 and SEQ ID NOs: 79, 80, and 81;

(g) SEQ ID NOs: 85, 86, and 87 and SEQ ID NOs: 91, 92, and 93;

(h) SEQ ID NOs: 97, 98, and 99 and SEQ ID NOs: 103, 104, and 105;

(i) SEQ ID NOs: 109, 110, and 111 and SEQ ID NOs: 115, 116, and 117;

(j) SEQ ID NOs: 121, 122, and 123 and SEQ ID NOs: 127, 128, and 129;

(k) SEQ ID NOs: 133, 134, and 135 and SEQ ID NOs: 139, 140, and 141; or (l) SEQ ID NOs: 145, 146, and 147 and SEQ ID NOs: 152, 152, and 153.

The antibodies described herein (or antigen-binding portions thereof) can be used for a variety of applications, including inhibition of an inflammatory or autoimmune response mediated by activated T cells or NK cell, inhibition of a viral or bacterial infection involving unwanted IP-10 activity, as well as detection of IP-10 protein.

In particular embodiments, the human IP-10 comprises a polypeptide having an amino acid sequence as set forth in SEQ ID NO: 157 (Genbank Acc. No. NP_001556); the CXCR3 comprises a polypeptide having an amino acid sequence as set forth in SEQ ID NO: 158 (Genbank Acc. No. NP_001495); the rhesus monkey IP-10 comprises a polypeptide having an amino acid sequence as set forth in SEQ ID NO: 159 (Genbank Acc. No. AAK95955); the mouse IP-10 comprises a polypeptide having an amino acid sequence as set forth in SEQ ID NO: 160 (Genbank Acc. No. NP_067249); the human MIG comprises a polypeptide having an amino acid sequence as set forth in SEQ ID NO: 161 (Genbank Acc. No. NP_002407); and/or the human ITAC comprises a polypeptide having an amino acid sequence as set forth in SEQ ID NO: 162 (Genbank Acc. No. NP_005400).

In another embodiment, the antibody, or antigen-binding portion thereof, further exhibits at least one of the following properties:

(a) inhibits binding of IP-10 to CXCR3;
(b) inhibits IP-10 induced calcium flux;
(c) inhibits IP-10 induced cell migration;
(d) cross-reacts with rhesus monkey IP-10;
(e) does not cross-react with mouse IP-10;
(f) does not cross-react with human MIG; and/or
(g) does not cross-react with human ITAC.

For example, the antibody, or antigen-binding portion thereof, exhibits at least two of properties (a), (b), (c), (d), (e), (f), and (g). Alternatively, the antibody, or antigen-binding portion thereof, exhibits at least three of properties (a), (b), (c), (d), (e), (f), and (g), or at least four, five, six, or all seven of properties (a), (b), (c), (d), (e), (f), and (g).

In another embodiment, the antibody, or antigen-binding portion thereof, binds to human IP-10 with a $K_D$ of $1\times10^{-9}$M or less, e.g., a $K_D$ of $1\times10^{-10}$ M or less, or a $K_D$ of $1\times10^{-11}$ M or less.

In yet another embodiment, the antibody, or antigen-binding portion thereof, binds to amino acid residues within SISNQP (SEQ ID NO: 163), VNPRSLEKL (SEQ ID NO: 164), and/or IIPASQFCPRVEIIA (SEQ ID NO: 165) of human IP-10.

Antibodies of the invention can be full-length antibodies, for example, of an IgG1, IgG2 or IgG4 isotype, e.g., an IgG1 isotype, optionally with a serine to proline mutation in the heavy chain constant region hinge region (at a position corresponding to position 241 as described in Angal et al. (1993) *Mol. Immunol.* 30:105-108), such that inter-heavy chain disulfide bridge heterogeneity is reduced or abolished. In one aspect, the constant region isotype is IgG4 with a mutation at amino acid residues 228, e.g., S228P. Alternatively, the antibodies can be antibody fragments (e.g. binding fragments), such as Fab, Fab' or Fab'2 fragments, or single chain antibodies.

In another aspect, the antibody (or antigen-binding portion thereof) is part of an immunoconjugate which includes a therapeutic agent, e.g., a cytotoxin or a radioactive isotope, linked to the antibody. In another aspect, the antibody is part of a bispecific molecule which includes a second functional moiety (e.g., a second antibody) having a different binding specificity than said antibody, or antigen binding portion thereof.

Compositions comprising antibodies, or antigen-binding portions thereof, immunoconjugates or bispecific molecules of the invention, optionally formulated in a pharmaceutically acceptable carrier, also are provided.

Nucleic acid molecules encoding the antibodies, or antigen-binding portions (e.g., variable regions and/or CDRs) thereof, also are provided, as well as expression vectors comprising such nucleic acids and host cells comprising such expression vectors. Methods for preparing anti-IP-10 antibodies using the host cells comprising such expression vectors also are provided, and can include the steps of (i) expressing the antibody in the host cell and (ii) isolating the antibody from the host cell.

In another aspect, the invention provides a method of inhibiting an inflammatory or autoimmune response mediated by activated T cells or NK cells comprising contacting the T cells or NK cells with the antibody, or antigen-binding portion thereof, of the invention, such that the inflammatory or autoimmune response is inhibited. In yet another aspect, the invention provides a method of treating an inflammatory or autoimmune disease in a subject in need of treatment comprising administering to the subject the antibody, or antigen-binding portion thereof, of the invention, such that the inflammatory or autoimmune disease in the subject is treated. The disease can be, for example, multiple sclerosis, rheumatoid arthritis, inflammatory bowel disease (e.g., ulcerative colitis, Crohn's disease), systemic lupus erythematosus, Type I diabetes, inflammatory skin disorders (e.g., psoriasis, lichen planus), autoimmune thyroid disease (e.g., Graves' disease, Hashimoto's thyroiditis), Sjogren's syndrome, pulmonary inflammation (e.g., asthma, chronic obstructive pulmonary disease, pulmonary sarcoidosis, lymphocytic alveolitis), transplant rejection, spinal cord injury, brain injury (e.g., stroke), neurodegenerative diseases (e.g., Alzheimer's disease, Parkinson's disease), gingivitis, gene therapy-induced inflammation, diseases of angiogenesis, inflammatory kidney disease (e.g., IgA nephropathy, membranoproliferative glomerulonephritis, rapidly progressive glomerulonephritis) and atherosclerosis.

In still another aspect, the invention provides a method of treating a viral or bacterial infection involving unwanted IP-10 activity in a subject in need of treatment comprising administering to the subject the antibody, or antigen-binding portion thereof, of the invention, such that the viral or bacterial infection in the subject is treated. For example, the antibodies can be used to treat viral meningitis, viral encephalitis or bacterial meningitis. Viral infection to be treated by the method of the invention can be mediated by, for example, human immunodeficiency virus (HIV), hepatitis C virus (HCV), herpes simplex virus type I (HSV-1) or the Severe Acute Respiratory Syndrome (SARS) virus.

In one embodiment, the method comprises administration of a single dose of between 30-450 mg of the anti-IP-10 antibody (or antigen-binding portion thereof), for example, a single dose of the antibody at a dose of 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 450 mg, or a dose of 35 mg, 45 mg, 55 mg, 65 mg, 75 mg, 85 mg, 95 mg, 105 mg, 115 mg, 125 mg, 135 mg, 145 mg, 155 mg, 165 mg, 175 mg, 185 mg, 195 mg, 205 mg, 215 mg, 225 mg, 235 mg, 245 mg, 255 mg, 265 mg, 275 mg, 285 mg, 295 mg, 305 mg, 315 mg, 325 mg, 335 mg, 345 mg, 355 mg, 355 mg, 375 mg, 385 mg, 395 mg, 405 mg, or 445 mg.

In another embodiment, the antibody is administered every week or every two weeks. In yet another embodiment, the antibody is administered for a period of about twelve weeks, e.g., on Days 1, 15, 29, 43, 57, and 71.

The antibody can be administered to a subject by any suitable means, for example, by intravenous administration or subcutaneous administration.

In one embodiment, the method is for treating ulcerative colitis comprising intravenous administration of a single dose of about 40 mg of the antibody, or antigen-binding portion thereof, every two weeks for a period of about twelve weeks.

In yet another embodiment, the anti-IP-10 antibody is administered as a first ("front") line of treatment (e.g., the initial or first treatment). In another embodiment, the anti-IP-10 antibody is administered as a second line of treatment (e.g., after initial treatment with the same or a different therapeutic, including after relapse and/or where the first treatment has failed).

The efficacy of the treatment methods provided herein can be assessed using any suitable means. In one embodiment, the treatment produces at least one therapeutic effect, e.g., a complete response, partial response, and stable disease.

Also provided are kits that include a pharmaceutical composition containing an anti-IP-10 antibody, such as IP10.44 (BMS-986184), and a pharmaceutically-acceptable carrier, in a therapeutically effective amount adapted for use in the methods described herein. In one embodiment, the kit comprises:

(a) a dose of an anti-IP-10 antibody comprising CDR1, CDR2 and CDR3 domains of the heavy chain variable region having the sequence set forth in SEQ ID NOs: 16, 28, 40, 52, 64, 76, 88, 100, 112, 124, 136, or 148, such as the CDR1, CDR2, and CDR3 sequences from SEQ ID NO: 16 (e.g., as set forth in SEQ ID NOs: 13, 14, and 15, respectively), and CDR1, CDR2 and CDR3 domains of the light chain variable region having the sequence set forth in SEQ ID NOs: 22, 34, 46, 58, 70, 82, 94, 106, 118, 130, 142, or 154, such as the CDR1, CDR2, and CDR3 sequences from SEQ ID NO: 22 (e.g., as set forth in SEQ ID NOs: 19, 20, and 21, respectively); and (b) instructions for using the anti-IP-10 antibody in a method of the invention.

In another embodiment, these methods comprise administering a composition, bispecific, or immunoconjugate of the invention.

In another aspect, the invention provides anti-IP-10 antibodies and compositions of the invention for use in the foregoing methods, or for the manufacture of a medicament for use in the foregoing methods (e.g., for treatment).

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 5) and amino acid sequence (SEQ ID NO: 4) of the heavy chain variable region of the IP10.1 (6A5) human monoclonal antibody. The CDR1 (SEQ ID NO: 1), CDR2 (SEQ ID NO: 2) and CDR3 (SEQ ID NO: 3) regions are delineated and the V, D and J germline derivations are indicated.

FIG. 1B shows the nucleotide sequence (SEQ ID NO:11) and amino acid sequence (SEQ ID NO: 10) of the light chain variable region of the 1P10.1 human monoclonal antibody. The CDR1 (SEQ ID NO:7), CDR2 (SEQ ID NO:8) and CDR3 (SEQ ID NO:9) regions are delineated and the V and J germline derivations are indicated.

FIG. 2A shows the nucleotide sequence (SEQ ID NO:17) and amino acid sequence (SEQ ID NO:16) of the heavy chain variable region of the IP10.44 human monoclonal antibody. The CDR1 (SEQ ID NO: 13), CDR2 (SEQ ID NO: 14) and CDR3 (SEQ ID NO: 15) regions are delineated and the V, D and J germline derivations are indicated.

FIG. 2B shows the nucleotide sequence (SEQ ID NO:23) and amino acid sequence (SEQ ID NO:22) of the light chain variable region of the IP10.44 human monoclonal antibody. The CDR1 (SEQ ID NO: 19), CDR2 (SEQ ID NO:20) and CDR3 (SEQ ID NO:21) regions are delineated and the V and J germline derivations are indicated.

FIG. 3A shows the nucleotide sequence (SEQ ID NO:29) and amino acid sequence (SEQ ID NO:28) of the heavy chain variable region of the IP10.45 human monoclonal antibody. The CDR1 (SEQ ID NO: 25), CDR2 (SEQ ID NO: 26) and CDR3 (SEQ ID NO: 27) regions are delineated and the V, D and J germline derivations are indicated.

FIG. 3B shows the nucleotide sequence (SEQ ID NO:35) and amino acid sequence (SEQ ID NO:34) of the light chain variable region of the IP10.45 human monoclonal antibody. The CDR1 (SEQ ID NO:31), CDR2 (SEQ ID NO:32) and CDR3 (SEQ ID NO: 33) regions are delineated and the V and J germline derivations are indicated.

FIG. 4A shows the nucleotide sequence (SEQ ID NO:41) and amino acid sequence (SEQ ID NO:40) of the heavy chain variable region of the IP10.46 human monoclonal antibody. The CDR1 (SEQ ID NO: 37), CDR2 (SEQ ID NO: 38) and CDR3 (SEQ ID NO: 39) regions are delineated and the V, D and J germline derivations are indicated.

FIG. 4B shows the nucleotide sequence (SEQ ID NO:47) and amino acid sequence (SEQ ID NO:46) of the light chain variable region of the IP10.46 human monoclonal antibody. The CDR1 (SEQ ID NO:43), CDR2 (SEQ ID NO: 44) and CDR3 (SEQ ID NO: 45) regions are delineated and the V and J germline derivations are indicated.

FIG. 5A shows the nucleotide sequence (SEQ ID NO:53) and amino acid sequence (SEQ ID NO:52) of the heavy chain variable region of the IP10.52 human monoclonal antibody. The CDR1 (SEQ ID NO: 49), CDR2 (SEQ ID NO:50) and CDR3 (SEQ ID NO:51) regions are delineated and the V, D and J germline derivations are indicated.

FIG. 5B shows the nucleotide sequence (SEQ ID NO: 59) and amino acid sequence (SEQ ID NO: 58) of the light chain variable region of the IP10.52 human monoclonal antibody. The CDR1 (SEQ ID NO: 55), CDR2 (SEQ ID NO: 56) and CDR3 (SEQ ID NO: 57) regions are delineated and the V and J germline derivations are indicated.

FIG. 6A shows the nucleotide sequence (SEQ ID NO: 65) and amino acid sequence (SEQ ID NO: 64) of the heavy chain variable region of the IP10.53 human monoclonal antibody. The CDR1 (SEQ ID NO: 61), CDR2 (SEQ ID NO: 62) and CDR3 (SEQ ID NO: 63) regions are delineated and the V, D and J germline derivations are indicated.

FIG. 6B shows the nucleotide sequence (SEQ ID NO: 71) and amino acid sequence (SEQ ID NO: 70) of the light chain variable region of the IP10.53 human monoclonal antibody. The CDR1 (SEQ ID NO: 67), CDR2 (SEQ ID NO: 68) and CDR3 (SEQ ID NO: 69) regions are delineated and the V and J germline derivations are indicated.

FIG. 7A shows the nucleotide sequence (SEQ ID NO: 77) and amino acid sequence (SEQ ID NO: 76) of the heavy chain variable region of the IP10.43 human monoclonal antibody. The CDR1 (SEQ ID NO: 73), CDR2 (SEQ ID NO: 74) and CDR3 (SEQ ID NO: 75) regions are delineated and the V, D and J germline derivations are indicated.

FIG. 7B shows the nucleotide sequence (SEQ ID NO: 83) and amino acid sequence (SEQ ID NO: 82) of the light chain variable region of the IP10.43 human monoclonal antibody. The CDR1 (SEQ ID NO: 79), CDR2 (SEQ ID NO: 80) and CDR3 (SEQ ID NO: 81) regions are delineated and the V and J germline derivations are indicated.

FIG. 8A shows the nucleotide sequence (SEQ ID NO: 89) and amino acid sequence (SEQ ID NO: 88) of the heavy chain variable region of the IP10.47 human monoclonal antibody. The CDR1 (SEQ ID NO: 85), CDR2 (SEQ ID NO: 86) and CDR3 (SEQ ID NO: 87) regions are delineated and the V, D and J germline derivations are indicated.

FIG. 8B shows the nucleotide sequence (SEQ ID NO: 95) and amino acid sequence (SEQ ID NO: 94) of the light chain variable region of the IP10.47 human monoclonal antibody. The CDR1 (SEQ ID NO: 91), CDR2 (SEQ ID NO: 92) and CDR3 (SEQ ID NO: 93) regions are delineated and the V and J germline derivations are indicated.

FIG. 9A shows the nucleotide sequence (SEQ ID NO: 101) and amino acid sequence (SEQ ID NO: 100) of the heavy chain variable region of the IP10.48 human monoclonal antibody. The CDR1 (SEQ ID NO: 97), CDR2 (SEQ ID NO: 98) and CDR3 (SEQ ID NO: 99) regions are delineated and the V, D and J germline derivations are indicated.

FIG. 9B shows the nucleotide sequence (SEQ ID NO: 107) and amino acid sequence (SEQ ID NO: 106) of the light chain variable region of the IP10.48 human monoclonal antibody. The CDR1 (SEQ ID NO: 103), CDR2 (SEQ ID NO: 104) and CDR3 (SEQ ID NO: 105) regions are delineated and the V and J germline derivations are indicated.

FIG. 10A shows the nucleotide sequence (SEQ ID NO: 113) and amino acid sequence (SEQ ID NO: 112) of the heavy chain variable region of the IP10.49 human monoclonal antibody. The CDR1 (SEQ ID NO: 109), CDR2 (SEQ ID NO: 110) and CDR3 (SEQ ID NO: 111) regions are delineated and the V, D and J germline derivations are indicated.

FIG. 10B shows the nucleotide sequence (SEQ ID NO: 119) and amino acid sequence (SEQ ID NO: 118) of the light chain variable region of the IP10.49 human monoclonal antibody. The CDR1 (SEQ ID NO: 115), CDR2 (SEQ ID NO: 116) and CDR3 (SEQ ID NO: 117) regions are delineated and the V and J germline derivations are indicated.

FIG. 11A shows the nucleotide sequence (SEQ ID NO: 125) and amino acid sequence (SEQ ID NO: 124) of the heavy chain variable region of the IP10.50 human monoclonal antibody. The CDR1 (SEQ ID NO: 121), CDR2 (SEQ ID NO: 122) and CDR3 (SEQ ID NO: 123) regions are delineated and the V, D and J germline derivations are indicated.

FIG. 11B shows the nucleotide sequence (SEQ ID NO: 131) and amino acid sequence (SEQ ID NO: 130) of the light chain variable region of the IP10.50 human monoclonal antibody. The CDR1 (SEQ ID NO: 127), CDR2 (SEQ ID NO: 128) and CDR3 (SEQ ID NO: 129) regions are delineated and the V and J germline derivations are indicated.

FIG. 12A shows the nucleotide sequence (SEQ ID NO: 137) and amino acid sequence (SEQ ID NO: 136) of the heavy chain variable region of the IP10.51 human monoclonal antibody. The CDR1 (SEQ ID NO: 133), CDR2 (SEQ ID NO: 134) and CDR3 (SEQ ID NO: 135) regions are delineated and the V, D and J germline derivations are indicated.

FIG. 12B shows the nucleotide sequence (SEQ ID NO: 143) and amino acid sequence (SEQ ID NO: 142) of the light chain variable region of the IP10.51 human monoclonal antibody. The CDR1 (SEQ ID NO: 139), CDR2 (SEQ ID NO: 140) and CDR3 (SEQ ID NO: 141) regions are delineated and the V and J germline derivations are indicated.

FIG. 13A shows the nucleotide sequence (SEQ ID NO: 149) and amino acid sequence (SEQ ID NO: 148) of the heavy chain variable region of the IP10.54 human monoclonal antibody. The CDR1 (SEQ ID NO: 145), CDR2 (SEQ ID NO: 146) and CDR3 (SEQ ID NO: 147) regions are delineated and the V, D and J germline derivations are indicated.

FIG. 13B shows the nucleotide sequence (SEQ ID NO: 155) and amino acid sequence (SEQ ID NO: 154) of the light chain variable region of the IP10.54 human monoclonal antibody. The CDR1 (SEQ ID NO: 151), CDR2 (SEQ ID NO: 152) and CDR3 (SEQ ID NO: 153) regions are delineated and the V and J germline derivations are indicated.

FIG. 18A and FIG. 18B (IL-6), FIG. 18C and FIG. 18D (IFNγ), and FIG. 18E and FIG. 18F (IL-12p40) are graphs showing the activity of antibody surrogates of IP10.44 (18G2) and anti-TNFα antibody to reduce circulating levels of cytokines in m and inflamed gut using the CD40-induced colitis model.

DETAILED DESCRIPTION OF THE INVENTION

Figure 14:
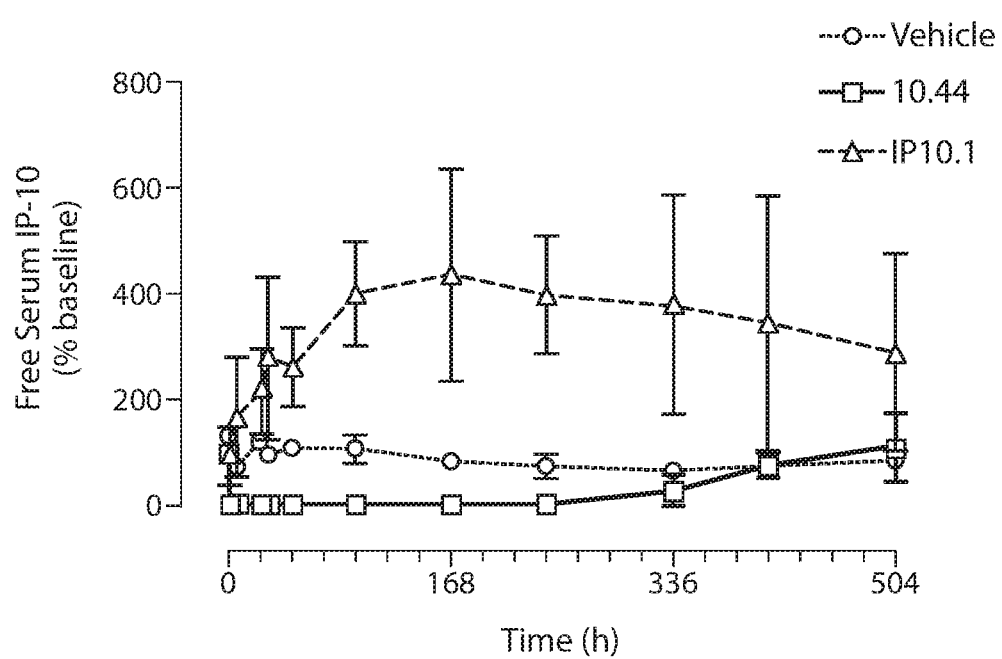
FIG. 14 is a graph showing the activity of antibodies IP10.1 and IP10.44 to suppress free serum IP-10.

In order that the present invention may be more readily understood, certain terms are first defined. Additional definitions are set forth throughout the detailed description.

The terms "6A5," "antibody 6A5," "antibody IP10.1," IP10.1," and "Eldelumab" refer to the anti-human IP-10 antibody, 6A5, described in WO2005/058815. The nucleotide sequence (SEQ ID NO: 5) encoding the heavy chain variable region of IP10.1 and the corresponding amino acid sequence (SEQ ID NO: 4) are shown in FIG. 1A (with CDR sequences designated as SEQ ID NOs: 1, 2, and 3, respectively). The nucleotide sequence (SEQ ID NO: 11) encoding the light chain variable region of IP10.1 and the corresponding amino acid sequence (SEQ ID NO: 10) are shown in FIG. 1B (with CDR sequences designated as SEQ ID NOs: 7, 8, and 9, respectively).

The terms "interferon gamma inducible protein 10" "IP-10," and "CXCL10" are used interchangeably, and include variants, isoforms and species homologs of human IP-10. Accordingly, human antibodies of the invention may, in certain cases, cross-react with IP-10 from species other than human. In other cases, the antibodies may be completely specific for human IP-10 and may not exhibit species or other types of cross-reactivity. The complete amino acid sequence of human IP-10 has Genbank accession number NP_001556 (SEQ ID NO: 157). The complete amino acid sequence of rhesus monkey IP-10 has Genbank accession number AAK95955 (SEQ ID NO: 159). The complete amino acid sequence of mouse IP-10 has Genbank accession number NP_067249 (SEQ ID NO: 160).

The term "CXCR3" refers to the receptor for IP-10 (CXCL10). The complete amino acid sequence of human CXCR3 has Genbank accession number NP_001495 (SEQ ID NO: 158).

The term "MIG" refers to a ligand for CXCR3, also known as monokine induced by gamma interferon, that is distinct from IP-10. The complete amino acid sequence of human MIG has Genbank accession number NP_002407 (SEQ ID NO: 161).

The term "ITAC" refers to a ligand for CXCR3, also known as interferon-inducible T cell alpha chemoattractant, that is distinct from IP-10. The complete amino acid sequence of human ITAC has Genbank accession number NP_005400 (SEQ ID NO: 162).

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the CXCR3 receptor to which the IP-10 molecule binds.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., IP-10). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds IP-10 is substantially free of antibodies that specifically bind antigens other than IP-10). An isolated antibody that specifically binds IP-10 may, however, have cross-reactivity to other antigens, such as IP-10 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human IP-10" is intended to refer to an antibody that binds to human IP-10 with a $K_D$ of $5\times10^{-9}$ M or less, more preferably $1\times10^{-10}$ M or less, and even more preferably $1\times10^{-11}$ M or less. An antibody that "cross-reacts with rhesus monkey IP-10" is intended to refer to an antibody that binds to rhesus monkey IP-10 with a $K_D$ of $1\times10^{-9}$ M or less, more preferably $1\times10^{-10}$ M or less, and even more preferably $1\times10^{-11}$ M or less. An antibody that "does not crossreact with mouse IP-10" or "does not cross-react with human MIG" or "does not cross-react with human ITAC" is intended to refer to an antibody that binds to mouse IP-10, human MIG or human ITAC with a $K_D$ of $1.5\times10^{-8}$ M or greater, more preferably a $K_D$ of $5$-$10\times10^{-8}$M or greater and even more preferably $1\times10^{-7}$ M or greater. In certain embodiments, such antibodies that do not cross-react with mouse IP-10, human MIG and/or human ITAC exhibit essentially undetectable binding against these proteins in standard binding assays.

As used herein, an antibody that "inhibits binding of IP-10 to CXCR3" is intended to refer to an antibody that inhibits IP-10 binding to CXCR3 with a $K_i$ of 1 nM or less, more preferably 0.75 nM or less, even more preferably 0.5 nM or less and even more preferably 0.25 nM or less.

As used herein, an antibody that "inhibits IP-10 induced calcium flux" is intended to refer to an antibody that inhibits IP-10 induced calcium flux with a $IC_{50}$ of 10 nM or less, more preferably 7.5 nM or less, even more preferably 5 nM or less and even more preferably 2.5 nM or less.

As used herein, an antibody that "inhibits IP-10 induced cell migration" is intended to refer to an antibody that inhibits human IP-10 induced cell migration with a $IC_{50}$ of 2 µg/ml or less, more preferably 1 µg/ml or less, even more preferably 0.5 µg/ml or less and even more preferably 0.25 µg/ml or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$M or less, more preferably $10^{-8}$M or less.

As used herein, the term "subject" includes any human or nonhuman animal. The term "nonhuman animal" includes all vertebrates, e.g., mammals and non-mammals, such as nonhuman primates, sheep, dogs, cats, horses, cows chickens, amphibians, reptiles, etc.

Various aspects of the invention are described in further detail in the following subsections.

Anti-IP-10 Antibodies

The antibodies of the invention bind specifically to human IP-10 and are characterized by particularly improved functional features or properties of the antibodies, as described above. Additionally, the antibodies may cross react with IP-10 from one or more non-human primates, such as rhesus monkey. Preferably, the antibodies do not cross react with mouse IP-10. Moreover, although MIG and ITAC are also ligands for the CXCR3 receptor, the antibodies of the invention preferably do not cross react with human MIG or human ITAC.

Preferably, an antibody of the invention binds to IP-10 with high affinity, for example with a $K_D$ of $10^{-8}$ M or less or $10^{-9}$ M or less or even $10^{-10}$ M or less.

Furthermore, the antibodies of the invention are capable of inhibiting one or more functional activities of IP-10. For example, in one embodiment, the antibodies inhibit the binding of IP-10 to CXCR3. In another embodiment, the antibodies inhibit IP-10 induced calcium flux. In yet another embodiment, the antibodies inhibit IP-10 induced cell migration (chemotaxis).

Standard assays to evaluate the binding ability of the antibodies toward IP-10 of various species and/or MIG or ITAC are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of IP-10 (e.g., receptor binding, calcium flux, chemotaxis) are described in further detail in the Examples.

Accordingly, an antibody that "inhibits" one or more of these IP-10 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). Preferably an antibody that inhibits an IP-10 activity effects such a statistically significant decrease by at least 10% of the measured parameter, more preferably by at least 20%, 30%, 40%, 50%, 60%, 70%, 80% or 90%, and in certain preferred embodiments an antibody of the invention may inhibit greater than 92%, 94%, 95%, 97%, 98% or 99% of an IP-10 functional activity.

Monoclonal Antibodies IP10.44, IP10.52, IP10.45, IP10.46, IP10.53, IP10.43, IP10.47, IP10.48, IP10.49, IP10.50, IP10.51, and IP10.54

Preferred antibodies of the invention are the human monoclonal antibodies IP10.44, IP10.43, IP10.45, IP10.46, IP10.47, IP10.48, IP10.49, IP10.50, IP10.51, IP10.52, IP10.53, or IP10.54. The $V_H$ amino acid sequences of IP10.44, IP10.43, IP10.45, IP10.46, IP10.47, IP10.48, IP10.49, IP10.50, IP10.51, IP10.52, IP10.53, and IP10.54 are shown in SEQ ID NOs: 16, 28, 40, 52, 64, 76, 88, 100, 112, 124, 136, and 148. The $V_L$ amino acid sequences of IP10.44, IP10.43, IP10.45, IP10.46, IP10.47, IP10.48, IP10.49, IP10.50, IP10.51, IP10.52, IP10.53, and IP10.54 are shown in SEQ ID NOs: 22, 34, 46, 58, 70, 82, 94, 106, 118, 130, 142, and 154.

A particular antibody of the invention is human monoclonal antibody, IP10.44 (also referred to herein as BMS-986184), structurally and chemically characterized as described below and in the following Examples. The $V_H$ amino acid sequence of IP10.44 is shown in SEQ ID NO: 16 (FIG. 2A). The $V_L$ amino acid sequence of IP10.44 is shown in SEQ ID NO: 22 (FIG. 2B).

The $V_H$ and $V_L$ sequences (or CDR sequences) of the antibodies described herein which bind human IP-10 can be "mixed and matched" with the $V_H$ and $V_L$ sequences (or CDR sequences) of other antibodies which bind human IP-10. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

For example, antibodies of the invention, or antigen binding portions thereof, comprise:

(a) a heavy chain variable region comprising the amino acid sequence of IP10.44, IP10.43, IP10.45, IP10.46, IP10.47, IP10.48, IP10.49, IP10.50, IP10.51, IP10.52, IP10.53, or IP10.54, e.g., SEQ ID NO: 16 (i.e., the $V_H$ of IP10.44); and (b) a light chain variable region comprising the amino acid sequence of IP10.44, IP10.43, IP10.45, IP10.46, IP10.47, IP10.48, IP10.49, IP10.50, IP10.51, IP10.52, IP10.53, or IP10.54, e.g., SEQ ID NO: 22 (i.e., the $V_L$ of IP10.44) or the $V_L$ of another anti-IP-10 antibody (i.e., which differs from IP10.44, IP10.43, IP10.45, IP10.46, IP10.47, IP10.48, IP10.49, IP10.50, IP10.51, IP10.52, IP10.53, or IP10.54); wherein the antibody specifically binds human IP-10.

In another embodiment, antibodies of the invention, or antigen binding portions thereof, comprise:

(a) the CDR1, CDR2, and CDR3 regions of the heavy chain variable region of IP10.44, IP10.43, IP10.45, IP10.46, IP10.47, IP10.48, IP10.49, IP10.50, IP10.51, IP10.52, IP10.53, or IP10.54, e.g., the CDR1, CDR2, and CDR3 regions of the heavy chain variable region comprising amino acid sequence SEQ ID NO: 16 (i.e., the CDR sequences of IP10.44, SEQ ID NOs: 13, 14, and 15, respectively); and (b) the CDR1, CDR2, and CDR3 regions of the light chain variable region of IP10.44, IP10.43, IP10.45, IP10.46, IP10.47, IP10.48, IP10.49, IP10.50, IP10.51, IP10.52, IP10.53, or IP10.54, e.g., the CDR1, CDR2, and CDR3 regions of the light chain variable region comprising amino acid sequence SEQ ID NO: 22 (i.e., the CDR sequences of IP10.44, SEQ ID NOs: 19, 20, and 21, respectively) or the CDRs of another anti-IP-10 antibody (i.e., which differs from IP10.44, IP10.43, IP10.45, IP10.46, IP10.47, IP10.48, IP10.49, IP10.50, IP10.51, IP10.52, IP10.53, or IP10.54); wherein the antibody specifically binds human IP-10. For example, the antibody, or antigen binding portion thereof, can include the heavy chain variable CDR1, CDR2, and CDR3 regions of IP10.44 combined with one or more of the light chain CDR1, CDR2, and/or CDR3 regions of other antibodies which bind human IP-10.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: Scientific Review 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152:5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention include at least the CDR3 region of the heavy chain variable region of IP10.44, IP10.43, IP10.45, IP10.46, IP10.47, IP10.48, IP10.49, IP10.50, IP10.51, IP10.52, IP10.53, or IP10.54 and at least the CDR3 of the light chain variable region of IP10.44, IP10.43, IP10.45, IP10.46, IP10.47, IP10.48, IP10.49, IP10.50, IP10.51, IP10.52, IP10.53, or IP10.54 (e.g., SEQ ID NOs: 15 and 21, the CDR3 of the heavy and light chain variable regions of IP10.44). These antibodies preferably (a) compete for binding with; (b) retain the functional characteristics; (c) bind to the same epitope; and/or (d) have a similar binding affinity as the antibody from which the CDR3 sequences are derived, e.g., antibody IP10.44.

Amino Acid Modifications

In another embodiment, antibodies of the invention comprise a heavy and/or light chain variable region sequences of CDR1, CDR2 and CDR3 sequences which differ from those of IP10.44, IP10.43, IP10.45, IP10.46, IP10.47, IP10.48, IP10.49, IP10.50, IP10.51, IP10.52, IP10.53, or IP10.54 (e.g., IP10.44) by one or more conservative modifications. In a preferred embodiment, however, (a) the glutamic acid and tyrosine residues of the $V_H$ CDR1 of IP10.44 (as underlined in the following sequence <u>EY</u>GMH (SEQ ID NO: 13)) are not modified, (b) the glycine, alanine, leucine, isoleucine, glycine, and alanine residues of the $V_H$ CDR2 of IP10.44 (as underlined in the following sequence V<u>IG</u>F<u>A</u>G LIK<u>GYA</u>DSVKG (SEQ ID NO: 14)) are not modified, and (c) the alanine and asparagines residues of the $V_H$ CDR3 of IP10.44 (as underlined in the following sequence EG<u>A</u>GS <u>N</u>IYYYYGMDV (SEQ ID NO: 15)) are not modified. It is understood in the art that certain conservative sequence modification can be made which do not remove antigen binding. See, e.g., Brummell et al. (1993) *Biochem* 32:1180-8; de Wildt et al. (1997) *Prot. Eng.* 10:835-41; Komissarov et al. (1997) *J. Biol. Chem.* 272:26864-26870; Hall et al. (1992) *J. Immunol.* 149:1605-12; Kelley and O'Connell (1993) *Biochem.* 32:6862-35; Adib-Conquy et al. (1998) *Int. Immunol.* 10:341-6 and Beers et al. (2000) *Clin. Can. Res.* 6:2835-43. Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises SEQ ID NO: 13, and/or conservative modifications thereof, except the glutamic acid and tyrosine residues of the $V_H$ CDR1 of IP10.44 (as underlined in the following sequence <u>EY</u>GMH (SEQ ID NO: 13)) are not modified; and/or (b) the heavy chain variable region CDR2 sequence comprises SEQ ID NO: 14, and/or conservative modifications thereof, except the glycine, alanine, leucine, isoleucine, glycine, and alanine residues of the $V_H$ CDR2 of IP10.44 (as underlined in the following sequence V<u>IG</u>F<u>A</u>G LIK<u>GYA</u>DSVKG (SEQ ID NO: 14)) are not modified; and/or (c) the heavy chain variable region CDR3 sequence comprises SEQ ID NO: 15, and conservative modifications thereof, except the alanine and asparagines residues of the $V_H$ CDR3 of IP10.44 (as underlined in the following sequence EG<u>A</u>GS<u>N</u>IYYYYGMDV (SEQ ID NO: 15)) are not modified; and/or (d) the light chain variable region CDR1, and/or CDR2, and/or CDR3 sequences comprise SEQ ID NO: 19, and/or, SEQ ID NO: 20, and/or SEQ ID NO: 21, and/or conservative modifications thereof; and (e) the antibody specifically binds human IP-10.

Additionally or alternatively, the antibody can possess one or more of the following functional properties described above, such as high affinity binding to human IP-10, the ability to bind to monkey IP-10 (e.g., cynomolgus monkey, rhesus monkey), but not substantially bind to mouse IP-10, the ability to not cross react with human MIG or human ITAC, and the ability to inhibit (a) the binding of IP-10 to CXCR3, (b) IP-10 induced calcium flux, and/or (c) IP-10 induced cell migration (chemotaxis).

In various embodiments, the antibody can be, for example, a human, humanized or chimeric antibody As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H$ and/or $V_L$ sequences of IP10.44, IP10.43, IP10.45, IP10.46, IP10.47, IP10.48, IP10.49, IP10.50, IP10.51, IP10.52, IP10.53, or IP10.54 (e.g., antibody IP10.44) as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332:323-327; Jones et al. (1986) *Nature* 321:522-525; Queen et al. (1989) *Proc. Natl. Acad. See. U.S.A.* 86:10029-10033; U.S. Pat. Nos. 5,225, 539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences of IP10.44, IP10.43, IP10.45, IP10.46, IP10.47, IP10.48, IP10.49, IP10.50, IP10.51, IP10.52, IP10.53, or IP10.54 (e.g., SEQ ID NOs: 13, 14, and 15, respectively), and/or a light chain variable region comprising CDR1, CDR2, and CDR3 sequences of IP10.44, IP10.43, IP10.45, IP10.46, IP10.47, IP10.48, IP10.49, IP10.50, IP10.51, IP10.52, IP10.53, or IP10.54 (e.g., SEQ ID NOs: 19, 20, and 21, respectively). While these antibodies contain the $V_H$ and $V_L$ CDR sequences of monoclonal antibody IP10.44 or other antibody described herein, they can contain differing framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline $V_H$ Sequences Reveals about Fifty Groups of $V_H$ Segments with Different Hypervariable Loops" *J. Mol. Biol.* 227:776-798; and Cox et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG_0010109, NT_024637 & BC070333), 3-33 (NG_0010109 & NT_024637) and 3-7 (NG_0010109 & NT_024637). As another example, the following heavy chain germline sequences found in the HCo12 HuMAb mouse are available in the accompanying Genbank Accession Nos.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art.

Preferred framework sequences for use in the antibodies of the invention are those that are structurally similar to the framework sequences used by selected antibodies of the invention, e.g., similar to the $V_H$ 3-33 framework sequences and/or the $V_K$ A27 framework sequences used by IP10.44. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-IP-10 monoclonal antibodies, or antigen binding portions thereof, comprising heavy and/or light chain variable region sequences described herein, wherein these sequences include one or more amino acid substitutions, deletions or additions. For example, an isolated anti-IP-10 monoclonal antibody, or antigen binding portion thereof, comprising a heavy chain variable region comprising: (a) a $V_H$ CDR1 region comprising SEQ ID NO: 13, or an amino acid sequence having one, two, or three amino acid substitutions, deletions or additions as compared to SEQ ID NO: 13 (preferably wherein the glutamic acid and tyrosine residues of the $V_H$ CDR1 of IP10.44 (as underlined in the following sequence EYGMH) are the same as in SEQ ID NO:13); (b) a $V_H$ CDR2 region comprising SEQ ID NO: 14, or an amino acid sequence having one, two, three, four or five amino acid substitutions, deletions or additions as compared to SEQ ID NO: 14 (preferably wherein the glycine, alanine, leucine, isoleucine, glycine, and alanine residues of the $V_H$ CDR2 of IP10.44 (as underlined in the following sequence VIGFAGLIKGYADSVKG) are the same as in SEQ ID NO:14); (c) a $V_H$ CDR3 region comprising SEQ ID NO: 15, or an amino acid sequence having one, two, three, four or five amino acid substitutions, deletions or additions as compared to SEQ ID NO: 15 (preferably wherein the alanine and asparagines residues of the $V_H$ CDR3 of IP10.44 (as underlined in the following sequence EGAGSNIYYYYGMDV) are the same as in SEQ ID NO:15); (d) a $V_L$ CDR1 region comprising SEQ ID NO: 19, or an amino acid sequence having one, two, three, four or five amino acid substitutions, deletions or additions as compared to SEQ ID NO: 19; (e) a $V_L$ CDR2 region comprising SEQ ID NO: 20, or an amino acid sequence having one, two, three, four or five amino acid substitutions, deletions or additions as compared to SEQ ID NO: 20; and (f) a $V_L$ CDR3 region comprising SEQ ID NO: 21, or an amino acid sequence having one, two, three, four or five amino acid substitutions, deletions or additions as compared to SEQ ID NO: 21.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In a preferred embodiment, the antibody is an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) J. Biol. Chem. 276:6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna.

Methods for production of antibodies in a plant system are disclosed in the art PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al. (1975) Biochem. 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Antibody Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J. Immunol 172:5489-94; Wallick et al (1988) J. Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. In some instances, it is preferred to have an anti-IP-10 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-IP-10 antibody that contains a pI value that falls in the normal range. This can be achieved either by selecting antibodies with a pI in the normal range or by mutating charged surface residues.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the IP10.44 monoclonal antibody. The DNA sequences encoding the VH and VL sequences of IP10.44 are shown in SEQ ID NOs: 17 and 23, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., el al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

In a preferred embodiment, the antibodies of the invention are human monoclonal antibodies. Such human monoclonal antibodies directed against IP-10 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IP-10 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-IP-10 antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-IP-10 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of IP-10 antigen and/or recombinant IP-10, or an IP-10 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 μs) of IP-10 antigen can be used to immunize the human Ig mice intraperitoneally.

Detailed procedures to generate fully human monoclonal antibodies to IP-10 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-IP-10 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12).

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

In another aspect, the present invention features an anti-IP-10 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-IP-10 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IP-10 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs)), and to target cells expressing IP-10. These bispecific molecules target IP-10 expressing cells to effector cell and trigger Fc receptor-mediated effector cell activities, such as phagocytosis of an IP-10 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-IP-10 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_C$ receptor or target cell antigen. The "anti-enhancement factor portion" can bind an $F_C$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9 M^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022C$_L$1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7 M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-IP-10 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-IP-10 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration of the antibody once per week, once every two weeks, once every three weeks, once every four weeks, once a month, once every 3 months or once every three to 6 months. For example, dosage regimens for the antibody include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. Preferred dosage regimens for the antibody also include administration of a single dose of between 30-450 mg of the anti-IP-10 antibody (or antigen-binding portion thereof). For example, a single dose of the antibody at a dose of 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 450 mg, or a dose of 35 mg, 45 mg, 55 mg, 65 mg, 75 mg, 85 mg, 95 mg, 105 mg, 115 mg, 125 mg, 135 mg, 145 mg, 155 mg, 165 mg, 175 mg, 185 mg, 195 mg, 205 mg, 215 mg, 225 mg, 235 mg, 245 mg, 255 mg, 265 mg, 275 mg, 285 mg, 295 mg, 305 mg, 315 mg, 325 mg, 335 mg, 345 mg, 355 mg, 355 mg, 375 mg, 385 mg, 395 mg, 405 mg, or 445 mg. In some methods, the antibody is administered every week or every two weeks. In yet another method, the antibody is administered for a period of about twelve weeks, e.g., on Days 1, 15, 29, 43, 57, and 71. For example, the method can include a single dose of about 40 mg of the antibody, or antigen-binding portion thereof, every two weeks for a period of about twelve weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, the antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the antibody (and other active component) in the pharmaceutical compositions of the present invention may be varied so as to obtain an amount of the antibody which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IP-10 antibody preferably results in a decrease in severity of disease symptoms, an increase in frequency and duration of disease symptom-free periods, or a prevention of impairment or disability due to the disease affliction. In the case of Rheumatoid Arthritis (RA), a therapeutically effective dose preferably prevents further deterioration of physical symptoms associated with RA, such as, for example, pain, fatigue, morning stiffness (lasting more than one hour), diffuse muscular aches, loss of appetite, weakness, joint pain with warmth, swelling, tenderness, and stiffness of a joint after inactivity. A therapeutically effective dose preferably also prevents or delays onset of RA, such as may be desired when early or preliminary signs of the disease are present. Likewise it includes delaying chronic progression associated with RA. Laboratory tests utilized in the diagnosis of RA include chemistries (including the measurement of IP-10 levels), hematology, serology and radiology. Accordingly, any clinical or biochemical assay that monitors any of the foregoing may be used to determine whether a particular treatment is a therapeutically effective dose for treating RA. One of ordinary skill in the art would be able to determine such amounts based on such factors as the subject's size, the severity of the subject's symptoms, and the particular composition or route of administration selected.

Compositions used in the present invention can be administered via one or more routes of administration using one or more of a variety of methods known in the art. As will be appreciated by the skilled artisan, the route and/or mode of administration will vary depending upon the desired results. Preferred routes of administration for antibodies include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the antibody can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies employed in the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. The term "subject" as used herein in intended to includes human and non-human animals. Non-human animals includes all vertebrates, e.g., mammals and non-mammals, such as non-human primates, sheep, dogs, cats, cows, horses, chickens, amphibians, and reptiles. The methods are particularly suitable for treating human patients having a disorder associated with aberrant IP-10 expression. When antibodies to IP-10 are administered together with another agent, the two can be administered in either order or simultaneously.

In one embodiment, the antibodies (and immunoconjugates and bispecific molecules) of the invention can be used to detect levels of IP-10, or levels of cells that contain IP-10. This can be achieved, for example, by contacting a sample (such as an in vitro sample) and a control sample with the anti-IP-10 antibody under conditions that allow for the formation of a complex between the antibody and IP-10. Any complexes formed between the antibody and IP-10 are detected and compared in the sample and the control. For example, standard detection methods, well-known in the art, such as ELISA and flow cytometic assays, can be performed using the compositions of the invention.

Accordingly, in one aspect, the invention further provides methods for detecting the presence of IP-10 (e.g., human IP-10 antigen) in a sample, or measuring the amount of IP-10, comprising contacting the sample, and a control sample, with an antibody of the invention, or an antigen binding portion thereof, which specifically binds to IP-10, under conditions that allow for formation of a complex between the antibody or portion thereof and IP-10. The formation of a complex is then detected, wherein a difference in complex formation between the sample compared to the control sample is indicative of the presence of IP-10 in the sample.

Also within the scope of the invention are kits comprising the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

IP-10 is know to have a chemoattractant effect on activated T cells and NK cells and to recruit such cells to sites of inflammation and autoimmune responses. Accordingly, the anti-IP-10 antibodies (and immunoconjugates and bispecific molecules) of the invention can be used to inhibit inflammatory or autoimmune response mediated by activated T cells and/or NK cells in a variety of clinical indications. The invention, therefore, provides a method of inhibiting an inflammatory or autoimmune response mediated by activated T cells and/or NK cells comprising contacting the T cells or NK cells with an antibody, or antigen-binding portion thereof, of the invention (or immunoconjugate or bispecific molecule of the invention) such that the inflammatory or autoimmune response is inhibited. Specific examples of inflammatory or autoimmune conditions in which the antibodies of the invention can be used include, but are not limited to, the following:

A. Multiple Sclerosis and Other Demyelinating Diseases

Expression of IP-10 mRNA has been shown to be increased in murine experimental allergic encephalomyelitis (EAE), a mouse model of multiple sclerosis (Godiska, R. et al. (1995) *J. Neuroimmunol.* 58:167-176). Moreover, increased levels of IP-10 have been found in the cerebrospinal fluid of MS patients during acute demyelinating events (Sorensen, T. L. et al. (1999) *J. Clin. Invest.* 103: 807-815; Franciotta et al. (2001) *J. Neuroimmunol.* 115:192-198). IP-10 also has been shown to be expressed by astrocytes in MS lesions, but not in unaffected white matter (Balashov, K. E. et al. (1999) *Proc. Natl. Acad. Sci. USA* 96:6873-6878) and to be expressed by macrophages within MS plaques and by reactive astrocytes in the surrounding parenchyma (Simpson, J. E. et al. (2000) *Neuropathol. Appl. Neurobiol.* 26:133-142). PCT Patent Publication WO 02/15932 showed administration of anti-IP-10 antibodies in a mouse hepatitis virus (MHV) model of MS resulted in reduced T lymphocyte and macrophage invasion, inhibited progression of demyelination, increased remyelination and improved neurological function (see also Liu, M. T. et al. (2001) *J. Immunol.* 167:4091-4097). Administration of murine anti-IP-10 antibodies has been shown to decrease clinical and histological disease incidence and severity in murine EAE (Fife, B. T. et al. (2001) *J. Immunol.* 166:7617-7624).

In view of the foregoing, the anti-IP-10 antibodies of the invention can be used in the treatment of MS and other demyelinating diseases by administering the antibody to a subject in need of treatment. The antibody can be used alone or in combination with other anti-MS agents, such as interferon beta-la (e.g., Avonex®, Rebif®), interferon beta-1b (e.g., Betaseron®), glatiramer acetate (e.g., Copaxone®) and/or mitoxantrone (e.g., Novantrone®).

B. Rheumatoid Arthritis

IP-10 levels have been shown to be significantly elevated in synovial fluid, synovial tissue and serum of patients with rheumatoid arthritis (RA) (Patel, D. D. et al. (2001) *Clin. Immunol.* 98:39-45; Hanaoka, R. et al. (2003) *Arthritis Res. and Therapy* 5:R74-R81). The IP-10 receptor, CXCR3, has been shown to be preferentially expressed on mast cells within synovial tissue from RA patients (Ruschpler, P. et al. (2003) *Arthritis Res. Ther.* 5:R241-R252). In an adjuvant induced arthritis (AA) rat model, a detectable autoantibody response against self IP-10 has been reported (Salomon, I. et al. (2002) *J. Immunol.* 169:2685-2693). Moreover, administration of an IP-10-encoding DNA vaccine augmented production of neutralizing anti-IP-10 antibodies within the rats, and these IP-10 autoantibodies could adoptively transfer resistance to AA to naïve rats (Salomon, I. et al., supra).

In view of the foregoing, the anti-IP-10 antibodies of the invention can be used in the treatment of rheumatoid arthritis by administering the antibody to a subject in need of treatment. The antibody can be used alone or in combination with other anti-RA agents, such as non-steroidal anti-inflammatory drugs (NSAIDs), analgesics, corticosteroids (e.g., prednisone, hydrocortisone), TNF-inhibitors (including adilimumab (Humira®), etanercept (Enbrel®) and infliximab (Remicade®)), disease-modifying anti-rheumatic drugs (including methotrexate, cyclophosphamide, cyclosporine, auranofin, azathioprine, gold sodium thiomalate, hydroxychloroquine sulfate, leflunomide, minocycline, penicillamine and sulfasalazine), fibromyalgia medications, osteoporosis medications and gout medications.

C. Inflammatory Bowel Disease

IP-10 expression has been shown to be significantly enhanced in cells infiltrating the lamina propria of colonic biopsies taken from ulcerative colitis patients (Uguccioni, M. et al. (1999) *Am. J. Pathol.* 155:331-336). Furthermore, neutralization of IP-10 has been shown to protect mice from epithelial ulceration in acute colitis and to enhance crypt cell survival (Sasaki, S. et al. (2002) *Eur. J Immunol.* 32:3197-3205). Also, in IL-10−/− mice, which develop colitis similar to Crohn's disease in humans, treatment with anti-IP-10 antibodies led to improvement in scoring of inflammation (Singh, U. P. et al. (2003) *J. Immunol.* 171:1401-1406).

In view of the foregoing, the anti-IP-10 antibodies of the invention can be used in the treatment of inflammatory bowel disease (IBD), including ulcerative colitis and Crohn's disease, by administering the antibody to a subject in need of treatment. The antibody can be used alone or in combination with other anti-IBD agents, such as drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., predinisone, hydrocortisone), TNF-inhibitors (including adilimumab (Humira®), etanercept (Enbrel®) and infliximab (Remicade®)), immunosuppressants (such as 6-mercaptopurine, azathioprine and cyclosporine A), and antibiotics.

D. Systemic Lupus Erythematosus

Serum IP-10 levels have been shown to be markedly increased in patients with systemic lupus erythematosus (SLE) and the levels have been shown to correlate with disease activity (see e.g., Narumi, S. et al. (2000) *Cytokine* 12:1561-1565). Accordingly, in another embodiment, the anti-IP-10 antibodies of the invention can be used in the treatment of SLE by administering the antibody to a subject in need of treatment. The antibody can be used alone or in combination with other anti-SLE agents, such as non-steroidal anti-inflammatory drugs (NSAIDs), analgesics, corticosteroids (e.g., predinisone, hydrocortisone), immunosuppressants (such as cyclophosphamide, azathioprine, and methotrexate), antimalarials (such as hydroxychloroquine) and biologic drugs that inhibit the production of dsDNA antibodies (e.g., LJP 394).

E. Type I Diabetes

Serum IP-10 levels have been shown to be elevated in patients with Type I diabetes, particularly those with recent onset disease, and the levels were shown to correlate with the number of GAD-reactive gamma-interferon-producing T cells in patients positive for GAD autoantibodies (Shimada, A. et al. (2001) *Diabetes Care* 24:510-515). In a separate study, serum IP-10 levels were found to be increased in patients with newly diagnosed disease and in patients at high risk for the disease, and IP-10 concentrations correlated with IFN-gamma levels (Nicoletti, F. et al. (2002) *Diabetologia* 45:1107-1110). Moreover, beta cells have been demonstrated to secrete IP-10, leading to chemoattraction of T cells, and mice deficient in CXCR3 have been shown to have delayed onset of Type I diabetes (Frigerio, S. et al. (2002) *Nature Medicine* 8:1414-1420).

Accordingly, in another embodiment, the anti-IP-10 antibodies of the invention can be used in the treatment of Type I diabetes by administering the antibody to a subject in need of treatment. The antibody can be used alone or in combination with other anti-diabetic agents, such as insulin.

F. Inflammatory Skin Disorders

IP-10 expression has been shown to be associated with a variety of inflammatory skin disorders. For example, IP-10 has been detected in keratinocytes and the dermal infiltrate from active psoriatic plaques (Gottlieb, A. B. et al. (1988) *J. Exp. Med.* 168:941-948). Moreover, CXCR3 is expressed by dermal CD3+ lymphocytes, suggesting that CXCR3 is involved in T lymphocyte trafficking to the psoriatic dermis (Rottman, J. B. et al. (2001) *Lab. Invest.* 81:335-347). Accordingly, in another embodiment, the anti-IP-10 antibodies of the invention can be used in the treatment of psoriasis by administering the antibody to a subject in need of treatment. The antibody can be used alone or in combination with other agents or treatments, such as topical treatments (e.g., steroids, coal tar, calcipotriene, tazarotene, anthralin, salicylic acid), phototherapy, systemic medications (e.g., methotrexate, oral retinoids, cyclosporine, fumaric acid esters) and/or biologic drugs (e.g., alefacept, efalizumab).

Lichen planus, a chronic inflammatory disease of the skin and oral mucosa, has been shown to be associated with infiltrating CD4+ and CD8+ T cells that express CXCR3 and, moreover, the CD8+ infiltrating cytolytic T cells have to shown to have IP-10 in their cytolytic granules and the lesional keratinocytes have been shown to overexpress IP-10 (Iijima, W. et al. (2003) *Am. J. Pathol.* 163:261-268). Accordingly, in another embodiment, the anti-IP-10 antibodies of the invention can be used in the treatment of lichen planus by administering the antibody to a subject in need of treatment. The antibody can be used alone or in combination with other agents or treatments, such as anti-inflammatory agents, anti-histamines, corticosteroids and light therapy.

IP-10 expression has been shown to be elevated in other inflammatory skin disorders, such as chronic discoid lupus erythematosus and Jessner's lymphocytic infiltration of the skin (Flier, J. et al. (2001) *J. Pathol.* 194:398-405). Accordingly, the anti-IP-10 antibodies of the invention can be used in the treatment of these inflammatory skin disorders by administering the antibody to a subject in need of treatment. The antibody can be used alone or in combination with other agents or treatments, as described above.

G. Autoimmune Thyroid Disease

Both IP-10 and CXCR3 have been shown to be expressed in the thyroid gland of patients suffering from Graves' Disease (GD), but not to be expressed (or poorly expressed) in normal thyroid tissue, and expression was highest in patients with recent onset GD (Romagnani, P. et al. (*Am. J. Pathol.* 161:195-206). IP-10 also has been shown to be expressed in thyroid tissue of patients suffering from Hashimoto's thyroiditis (Kemp, E. H. et al. (2003) *Clin. Endocrinol.* 59:207-213). Accordingly, in another embodiment, the anti-IP-10 antibodies of the invention can be used in the treatment of autoimmune thyroid disease, including Graves' Disease and Hashimoto's thyroiditis, by administering the antibody to a subject in need of treatment. The antibody can be used alone or in combination with other agents or treatments, such as anti-thyroid drugs, radioactive iodine and subtotal thyroidectomy.

H. Sjogren's Syndrome

The expression of IP-10 mRNA has been shown to be significantly upregulated in the salivary glands of patients with Sjogren's syndrome (SS), with expression being most prominent in the ductal epithelium adjacent to lymphoid infiltrates (see e.g., Ogawa, N. et al. (2002) *Arthritis Rheum.* 46:2730-2741). Accordingly, in another embodiment, the anti-IP-10 antibodies of the invention can be used in the treatment of Sjogren's Syndrome by administering the antibody to a subject in need of treatment. The antibody can be used alone or in combination with other anti-SS agents, such as artificial lubricants (e.g., preservative-free artificial tears, artificial salivas, unscented skin lotions, saline nasal sprays, and vaginal lubricants), Lacriserts® for treatment of dry eyes, pilocarpine hydrochloride (Salagen®) and ceyimeline (Eyoxac®) for treatment of dry mouth, non-steroidal anti-inflammatory drugs (NSAIDs), steroids and immunosuppressive drugs.

I. Pulmonary Inflammation

IP-10 expression has been examined in a mouse model of allergic asthma, with the results demonstrating that IP-10 is upregulated in the lungs after allergen challenge and that overexpression of IP-10 was associated with increased airway hyperactivity, eosinophilia, increased IL-4 levels and recruitment of CD8+ lymphocytes (Medoff, B. D. et al. (2002) *J. Immunol.* 168:5278-5286). Moreover, smokers who develop chronic obstructive pulmonary disease (COPD) have been shown to express IP-10 in their bronchiolar epithelium (Saetta, M. et al. (2002) *Am. J. Respir. Crit. Care Med.* 165:1404-1409). Still further, high levels of IP-10 have been demonstrated in the bronchoalveolar lavage fluid of patients with pulmonary sarcoidosis and lymphocytic alveolitis (Agostini, C. et al. (1998) *J. Immunol.* 161:6413-6420).

Accordingly, in another embodiment, the anti-IP-10 antibodies of the invention can be used in the treatment of disease characterized by pulmonary inflammation, such as asthma, COPD, pulmonary sarcoidosis or lymphocytic alveolitis, by administering the antibody to a subject in need of treatment. The antibody can be used alone or in combination with other agents for reducing pulmonary inflammation, such as cromolyn sodium, nedocromil sodium, inhaled corticosteroids, systemic (e.g., oral) corticosteroids, short acting beta antagonists, short acting bronchodilators, long acting beta antagonists or agonists (oral or inhaled), leukotriene modifiers, theophylline and oxygen therapy.

J. Transplant Rejection

IP-10 has been shown to play a role in rejection of transplanted tissue. For example, treatment of mice with neutralizing anti-IP-10 antibodies increased the survival of small bowel allografts and reduced accumulation of host Tcells and NK cells in the lamina propria (Zhang, Z. et al. (2002) *J. Immunol.* 168:3205-3212). Furthermore, in mice receiving pancreatic islet allografts, anti-IP-10 antibody treatment also resulted in increased allograft survival and decreased lymphocytic graft infiltration (Baker, M. S. et al. (2003) *Surgery* 134:126-133). Additionally, cardiac allografts, but not normal hearts, were shown to express IP-10 and CXCR3, and elevated IP-10 levels were associated with cardiac allograft vasculopathy (Zhao, D. X. et al. (2002) *J. Immunol.* 169:1556-1560). CXCR3 and IP-10 also have been shown to be expressed by inflammatory cells infiltrating lung allografts (Agostini, C. et al. (2001) *Am J. Pathol.* 158:1703-1711). Neutralization of CXCR3 or IP-10 in vivo was shown to attenuate bronchiolitis obliterans syndrome (BOS), the major limitation to survival for lung transplant recipients, in a murine lung transplant model (Belperio, J. A. et al. (2002) *J. Immunol.* 169:1037-1049).

In view of the foregoing, the invention also provides a method of inhibiting transplant rejection by administering an anti-IP-10 antibody of the invention to a transplant recipient in need of treatment. Examples of tissue transplants that can be treated include, but are not limited to, liver, lung (e.g., treatment of BOS), kidney, heart, small bowel, and pancreatic islet cells. The antibody can be used alone or in combination with other agents for inhibiting transplant rejection, such as immunosuppressive agents (e.g., cyclosporine, azathioprine, methylprednisolone, prednisolone, prednisone, mycophenolate mofetil, sirilimus, rapamycin, tacrolimus), anti-infective agents (e.g., acyclovir, clotrimazole, ganciclovir, nystatin, trimethoprimsulfarnethoxazole), diuretics (e.g., bumetanide, furosemide, metolazone) and ulcer medications (e.g., cimetidine, famotidine, lansoprazole, omeprazole, ranitidine, sucralfate).

K. Spinal Cord Injury

Traumatic injury to the spinal cord leads to infiltration of inflammatory cells. IP-10 has been shown to play a central role in secondary degeneration following spinal cord injury (Gonzalez et al. (2003) *Exp. Neurol.* 184:456-463; see also PCT patent publication WO 03/06045). IP-10 has been shown to be significantly elevated in the contused rat spinal cords 6 and 12 hours postinjury (McTigue, D. M. et al. (1998) *J. Neurosci. Res.* 53:368-376) and in the injured mouse spinal cord 6 hours post injury (Gonzalez et al. (2003) supra). Accordingly, inhibition of IP-10 activity after spinal cord injury has been shown to be useful in reducing infiltration of inflammatory cells and thus reducing secondary tissue damage to inflammation. Inhibition may also reduce infiltration of inflammatory cells, decrease secondary degeneration and improve recovery following traumatic brain injury and stroke. Thus, the invention also provides a method of treating spinal cord injury and brain injury (e.g., stroke) in a subject in need of treatment comprising administering to the subject an anti-IP-10 antibody of the invention. The antibody can be used alone or in combination with other agents, such as other anti-inflammatory agents.

L. Neurodegenerative Diseases

IP-10 and CXCR3 expression within the central nervous system has been found to be upregulated in association with pathological changes associated with Alzheimer's Disease (AD) (Xia, M. Q. and Hyman, D. T. (1999) *J. Neurovirol.* 5:32-41). Within AD brains, CXCR3 was shown to be expressed constitutively on neurons and neuronal processes in various cortical and subcortical regions and IP-10 was shown to be expressed in astrocytes and its level was markedly elevated as compared to normal brains (Xia, M. Q. et al. (2000) *J. Neuroimmunol.* 108:227-235). Accordingly, the antibodies of the invention can be used in the treatment of neurodegenerative diseases, such as Alzheimer's disease and Parkinson's disease, by administering to a subject in need of treatment the anti-IP-10 antibody, alone or in combination with other therapeutic agents. Examples of agents with which the anti-IP-10 antibody can be combined for Alzheimer's disease treatment include cholinesterase inhibitors (donepezil, rivastigmine, galantamine, tacrine) and vitamin E. An example of an agent with which the anti-IP-10 antibody can be combined for Parkinson's disease treatment is levodopa.

M. Gingivitis

Marginal periodontitis is associated with inflamed gingival tissue. Cells producing IP-10 have been found in inflamed human gingival tissue, as well as cells expressing the CXCR3 receptor (Kabashima, H. et al. (2002) *Cytokine* 20:70-77). Accordingly, in another embodiment, the anti-IP-10 antibodies of the invention can be used in the treatment of gingivitis by administering the antibody to a subject in need of treatment. The antibody can be used alone or in combination with other agents or treatments, such as anti-gingival mouthwashes (e.g., antibiotic mouthwashes), periodontal scaling and root planing and periodontal surgery.

N. Gene Therapy-Associated Inflammation

Replication-deficient adenoviruses, used as adenoviral vectors used in gene therapy, can cause acute injury and inflammation in tissues infected by the viral vectors. Such adenoviral vectors have been shown to induce the expression of IP-10 through capsid-dependent activation of NFkB (Borgland, S. L. et al. (2000) J. Virol. 74:3941-3947). Accordingly, the anti-IP-10 antibodies of the invention can be used to inhibit IP-10-induced injury and/or inflammation during gene therapy treatment that utilizes a viral vector, such as an adenoviral vector, that stimulates unwanted production of IP-10.

O. Diseases of Angiogenesis

IP-10 has been shown to inhibit angiogenesis in vitro and in vivo (Strieter et al. (1995) *Biochem. Biophys. Res. Commun.* 210:51-57; Angiolillo et al. (1995) *J. Exp. Med.* 182:155-162; Luster et al. (1995) *J. Exp. Med.* 182:219-231). Angiogenesis plays a crucial role in many disease processes, such as the healing response to trauma. For example, vasculature within the injured spinal cord remains in a state of active remodeling until at least 28 days post injury (Popovich et al. (1997) *J. Comp. Neurol.* 377:443-464).

IP-10 is thought to exert its angiostatic effects through the inhibition of endothelial cell growth and chemotaxis. It does this through its heparin-binding motif as well as through a receptor-mediated mechanism. Through its heparin-binding motif it prevents the angiogenic factors FGF-2 and VEFG165 from binding to their receptors. It also exerts its effects through a receptor-mediated process. The receptor for IP-10, CXCR3, is alternatively spliced to produce the two known variations CXCR3A and CXCR3B. IP-10 binding to the CXCR3A receptor leads to proliferation and chemotaxis of the target cell, whereas IP-10 binding to the CXCR3B receptor has the opposite effect of inhibition of growth and chemotaxis. It is through the CXCR3B receptor that IP-10 acts as an angiostatic factor (Lasagni et al. (2003) *J. Exp. Med.* 197:1537-1549).

In view of the foregoing, the anti-IP-10 antibodies of the invention can be used in the treatment of diseases requiring angiogenesis, for example where the angiostatic behaviour of IP-10 delays or prevents healing and exacerbates the disease process. Such diseases include: 1) aberrant physiological neovascularization, which may impact wound healing, the female estrus cycle, pregnancy, exercise-induced hypertrophy and the like; 2) indications that may require stimulation of neovascularization, including induction of collateral vessel formation (including myocardial ischemia, peripheral ischemia, cerebral ischemia), coronary artery disease, peripheral vascular disease, stroke, wound healing, engraftment subsequent to organ transplantation such as islet cell transplantation, fracture and tendon repair, reconstructive surgery, tissue engineering, restenosis, hair loss, decubitus and stasis ulcers, gastrointestinal ulcers, placental insufficiency, aseptic necrosis, pulmonary and systemic hypertension, vascular dementia, Alzheimer's Disease, cerebral autosomal dominant arteriopathy with subcortical infarcts and leukoencephalopathy (CADASIL); thyroid psuedocyst and lymphoedema; and 3) indications that may require vascular remodeling, including vascular malformations, psoriasis, and pre-eclampsia. The antibodies of the invention can be used alone or in combination with other angiogenesis inducing agents.

P. Inflammatory Kidney Disease

The CXCR3 receptor has been reported to be expressed by mesangial cells of patients with IgA nephropathy, membranoproliferative glomerulonephritis or rapidly progressive glomerulonephritis (Romagnani, P. et al. (1999) *J. Am. Soc. Nephrol.* 10:2518-2526). Furthermore, in a mouse model of nephrotoxic nephritis, IP-10 mRNA levels were increased six-fold in the cortex of nephritic kidneys 7 days after induction of nephritis (Schadde, E. et al. (2000) *Nephrol. Dial. Transplant.* 15:1046-1053). Still further, high levels of IP-10 expression were observed in kidney biopsy specimens of human patients with glomerulonephritis as compared to normal kidneys (Romagnani, P. et al. (2002) *J. Am. Soc. Nephrol.* 13:53-64). Accordingly, the anti-IP-10 antibodies of the invention can be used in the treatment of inflammatory kidney disease, including IgA nephropathy, memranoproliferative glomerulonephritis and rapidly progressive glomerulonephritis. The antibodies of the invention can be used alone or in combination with other agents or treatments used in the treatment of glomerulonephritis, such as antibiotics, diuretics, high blood pressure medications and dialysis.

Q. Atherosclerosis

IP-10 has been shown to be a mitogenic and chemotactic factor for vascular smooth muscle, which are important features of smooth muscle cells for their contribution to the pathogenesis of atherosclerosis (Wang, X. et al. (1996) *J. Biol. Chem.* 271:24286-24293). IP-10 also has been shown to be induced in smooth muscle cells after treatment with LPS or interferon gamma, and was also induced in the rat carotid artery after balloon angioplasty (Wang, X. et al. (1996) supra). Moreover, IP-10 has been demonstrated to be expressed in atheroma-associated endothelial cells, smooth muscle cells and macrophages, suggesting a role for IP-10 in recruitment and retention of activated T cells that have been observed within vascular wall lesions during atherogenesis (Mach, F. et al. (1999) *J. Clin. Invest.* 104:1041-1050). Accordingly, the anti-IP-10 antibodies of the invention can be used in the treatment or prevention of atherosclerosis. The antibodies can be used alone or in combination with other agents or treatments used in the treatment of atherosclerosis, such high blood pressure medications and cholesterol-lowering drugs.

R. Viral Infections

IP-10 may be upregulated in various viral infections and may play a beneficial role in recruiting activated T cells to fight the viral infection. In certain instances, however, production of IP-10 during viral infection may lead to detrimental effects and thus, the IP-10 activity may be unwanted and it may be desirable to inhibit IP-10 activity in such viral infections using an anti-IP-10 antibody of the invention.

For example, IP-10 has been shown to stimulate replication of human immunodeficiency virus (HIV) in monocyte-derived macrophages and peripheral blood lymphocytes (Lane, B. R. et al. (2003) *Virology* 307:122-134). Furthermore, IP-10 levels are elevated in cerebrospinal fluid and brain of HIV-infected patients and in the central nervous system of HIV gp120-transgenic mice (Asensio, V. C. et al. (2001) *J Virol.* 75:7067-7077).

IP-10 levels also have been shown to be elevated in patients with chronic persistent hepatitis C virus (HCV) and in patients with chronic active hepatitis (Narumi, S. et al. (1997) *J. Immunol.* 158:5536-5544). In HCV-infected livers, IP-10 was shown to be expressed by hepatocytes but not by other cell types within the liver, and a significantly higher proportion of CXCR3 positive T cells was found in the liver as compared to blood (Harvey, C. E. et al. (2003) *J. Leukoc. Biol.* 74:360-369).

Increased secretion of IP-10 has been shown to be associated with the inflammatory response to acute ocular herpes simplex virus type I (HSV-1) infection in mice, and treatment of HSV-1 infected mice with anti-IP-10 antibodies was shown to reduce mononuclear cell infiltration into the corneal stroma, reduce corneal pathology, and inhibit progression of the virus from the corneal stroma to the retina during acute infection (Carr, D. J. et al. (2003) *J. Virol.* 77:10037-10046).

IP-10 expression also has been shown to be expressed in viral meningitis. IP-10 was demonstrated to be present in the CSF of patients with viral meningitis and to be responsible for chemotactic activity on neutrophils, peripheral blood mononuclear cells and activated T cells (Lahrtz, F. et al. (1997) *Eur. J. Immunol.* 27:2484-2489; Lahrtz, F. et al. (1998) *J. Neuroimmunol.* 85:33-43).

In view of the foregoing, the anti-IP-10 antibodies of the invention can be used in the treatment of viral infections involving unwanted IP-10 activity by administering the antibody to a subject in need of treatment. Non-limiting examples of viral infections that can be treated include HIV (e.g., HIV-induced encephalitis), HCV, HSV-1, viral meningitis and Severe Acute Respiratory Syndrome (SARS). The antibody can be used alone or in combination with other anti-viral agents, such as, for HIV infection, nucleoside/nucleotide reverse transcriptase inhibitors, non-nucleoside reverse transcriptase inhibitors and/or protease inhibitors (and combinations thereof), for HCV infection, interferon alpha 2a, pegylated interferon alpha 2a, and/or ribavirin, and for HSV-1 infection, acyclovir, valacyclovir and/or famciclovir.

S. Bacterial Infections.

Bacterial infections induce IP-10 production in affected cells (see Gasper, N. A. et al. (2002) *Infect Immun.* 70:4075-82.) Bacterial meningitis is also specifically known to invoke IP-10 expression (Lapinet, J. A. et al. (2000) *Infect Immun.* 68:6917-23). IP-10 is also produced by testicular somatic cells of seminiferous tubules, in a bacterial infection model, strongly indicating a likely role of these chemokines in the accumulation of neutrophils and T lymphocytes during testicular inflammation, which is classically observed in the pathogenesis of bacterial infections (Aubry, F. et al. (2000) *Eur Cytokine Netw.* 11:690-8).

In view of the foregoing, the anti-IP-10 antibodies of the invention can be used in the treatment of bacterial infections involving unwanted IP-10 activity by administering the antibody to a subject in need of treatment. Examples of bacterial infections include, but are not limited to, bacterial meningitis and bacterial pneumonia. The antibody can be used alone or in combination with other anti-bacterial agents, such as antibiotics.

The present invention is further illustrated by the following examples which should not be construed as further limiting. The contents of all figures and all references, patents and published patent applications cited throughout this application are expressly incorporated herein by reference.

Methods and Materials:

Example 1: Design of Variants of Antibody IP10.1

Eldelumab (also referred to as IP10.1) was previously evaluated in several clinical trials in patients having RA, Crohn's Disease and Ulcerative Colitis. A signal of clinical response was observed in these trials. However, further development of Eldelumab was challenged by some issues, such as (1) sub-optimal (single-digit) nM affinity/potency which requires high doses for both IV and SC delivery and high dosing frequency for SC delivery; (2) significant IV infusion reactions from administration of high amounts of protein; and (3) up to 30% isomerization observed with 2 years of shelf life.

Given the issues with Eldelumab described above, next-generation antibodies with improved affinity and without potential for isomerization were generated. Antibody IP10.1 was first constructed into a scFv molecule and confirmed for activity prior to optimization. A scFv optimization library was generated using a combination of randomized (NNS) and doped oligonucleotides (70% parental, 30% all others) in the HCDR regions of IP10.1. Using the PROfusion® mRNA display system, this DNA library was taken through rounds of transcription and translation using rabbit reticulolysate. The encoding mRNA was fused to its own scFv via a puromycin linkage. During selection, any scFv that bound biotin-labeled IP-10 were captured by magnetic streptavidin beads and amplified by PCR to proceed into the next round. Cycles of PROfusion mRNA display system continued until a significant target binding signal was observed by quantitative polymerase chain reaction (qPCR®). This was followed by selections of increased stringency that were performed by dropping the target concentration and by favoring clones with tighter affinity during off-rate selections. Binding populations were cloned and sequenced. Unique clones that do not have chemical liabilities in the HCDR regions were expressed via high throughput mammalian expression system (HMEP) and tested for improvement in affinity for IP-10 using SPR (Biacore). Overall, more than 50 variants were generated by targeted randomization of the CDR1, CDR2, and CDR3 residues in the heavy chain variable region and screened for binding to human IP-10. Variants that demonstrated a significant improvement in off-rate at 37° C. were reformatted as IgGs (IgG1) and subjected to a further selection process. A comparison of the CDR sequences of IP10.1 and its variants (reformatted as IgG1 full length antibodies) is shown in Table 1. Table 2 shows the binding affinities of these variants compared to IP10.1 at 37° C. These variants were further analyzed for their cross-reactivity with cyno IP10, mouse IP10, or MIG (data not shown) and cross-competion with IP10.1, physical stability, conformational stability, hydrophobic-interactions, and aggregation (data not shown).

Two clones (IP10.44 and IP10.52) showed substantially higher affinity as compared to IP10.1, compete against IP10.1 for binding to IP-10, and have improved biophysical profile compared to IP10.1. Therefore, IP10.44 and IP10.52 were selected for further studies.

Accordingly, clones IP10.44 and IP10.52 were subjected to forced stability studies (oxidation and deamidation) to further differentiate their characteristics. While both antibodies showed similar behavior under forced stability conditions, IP10.52 showed slightly increased $V_H$ region deamidation and faster off rate as compared to IP10.44. Therefore, IP10.44 was selected for further characterization.

TABLE 1

Selection of variants for IgG1f reformat

| 6A5 | LCDR1 RASQSVSSSYLA (SEQ ID NO: 7) | LCDR2 GASSRAT (SEQ ID NO: 8) | HCDR1 N*MH (SEQ ID NO: 1) | HCDR2 VIWFMNKFYVDSVKG (SEQ ID NO: 2) | HCDR3 EGSGIYYYYGMDV (SEQ ID NO: 3) | Recom. Ab |
|---|---|---|---|---|---|---|
| Germline | ............ | ....... | SY... | ...Y..S..Y.A..... | ........ | |
| 3611_D02 | ........H.. | ....... | SY... | ..D.V.DT.Y.T..... | ...A..N......... | IP10.43-g1f |
| 3611_H09 | ............ | ....... | EY... | ..G.A.LI.G.A..... | ...A..N......... | IP10.44-g1f |
| 3612_A03 | ............ | ....... | KH... | ..G.A.VI.S.A..... | ...E..N..F...... | IP10.45-g1f |
| 3612_E04 | ............ | ....... | QY... | ..SYG.DI.Y.A..... | ...E..N......... | IP10.46-g1f |
| 3613_D03 | ............ | ....... | TH... | ..G.G.LI.S.A..... | .....SL.F...... | IP10.47-g1f |
| 3613_G10 | ............ | ....... | .Y... | ..D.A.I..Y.A..... | ...E..N..FF..... | IP10.48-g1f |

TABLE 1-continued

Selection of variants for IgG1f reformat

| 6A5 | LCDR1 RASQSVSSSYLA (SEQ ID NO: 7) | LCDR2 GASSRAT (SEQ ID NO: 8) | HCDR1 N*G*MH (SEQ ID NO: 1) | HCDR2 VIWF*G*MNKFYVDSVKG (SEQ ID NO: 2) | HCDR3 EG*G*SGIYYYYGMDV (SEQ ID NO: 3) | Recom. Ab IP10.1-g1f |
|---|---|---|---|---|---|---|
| 3641_E05 | ............ | ....... | QS... | ..G.G.LI.S.A..... | ................ | IP10.49-g1f |
| 3641_F09 | ............ | ....... | RF... | ..GYA.D..Y.A..... | ..A...N......... | IP10.50-g1f |
| 3642_C11 | ............ | ....... | DY... | ..GYG.LI.G.A..... | ..A...S......... | IP10.51-g1f |
| 3642_D10 | ............ | ....... | DY... | ..GYG.LI.G.A..... | ..A...SV........ | IP10.52-g1f |
| 3580_C10 | ............ | ....... | DY... | ..SHN.AI.G.A..... | .....N.......... | IP10.53-g1f |
| 3612_E04 | ............ | ....... | QY... | ..SYG.DI.Y.A..... | ..E...N......... | IP10.54-g1f |

TABLE 2

Variants with improved binding affinity vs. IP10.1

| Mab | KD × $10^{-9}$(M) | Ka × $10^4$(1/Ms) | Kd × $10^{-4}$(1/s) | % Monomer |
|---|---|---|---|---|
| IP10.52 | 0.02 | 6.36 | 0.003 | 93 |
| IP10.53 | 0.10 | 1.01 | 0.01 | 66 |
| IP10.45 | 0.11 | 3.19 | 0.03 | 97 |
| IP10.46 | 0.12 | 1.35 | 0.02 | 69 |

TABLE 2-continued

Variants with improved binding affinity vs. IP10.1

| Mab | KD × $10^{-9}$(M) | Ka × $10^4$(1/Ms) | Kd × $10^{-4}$(1/s) | % Monomer |
|---|---|---|---|---|
| IP10.44 | 0.17 | 2.62 | 0.04 | 96 |
| IP10.54 | 0.25 | 1.54 | 0.04 | 67 |
| IP10.48 | 0.34 | 1.41 | 0.05 | 93 |
| IP10.49 | 0.41 | 1.47 | 0.06 | 69 |
| IP10.47 | 0.56 | 2.40 | 0.14 | 89 |
| IP10.51 | 0.96 | 3.16 | 0.06 | 93 |
| IP10.50 | 1.03 | 0.68 | 0.07 | 92 |
| IP10.43 | 1.64 | 0.93 | 0.17 | 95 |
| IP10.1g1f | 4.18 | 3.62 | 1.51 | 92 |
| IP10.1g1f | 6.27 | 2.2 | 1.38 | 93 |

Example 2: Characterization of IP10.44

A. Biophysical and Biochemical Characterization of IP10.44

1. Binding

In Biacore®-based binding studies, IP10.1 had a $K_D$ of approximately 5 nM and IP10.44 exhibited a $K_D$ of 10 pM (limit of detection with the Biacore is 90 pM), indicating at least 50-fold improvement. Like IP10.1, IP10.44 has similar $K_D$ in monkey and human, and does not crossreact with mouse.

TABLE 3

| Clone | Lot # | Affinity (w/huIP-10) KD × $10^{-9}$ (nM) | On rate × $10^4$ (1/Ms) | Off rate $10^{-4}$ (1/s) | Affinity (w/cynoIP-10) KD × $10^{-9}$ (nM) | Affinity (w/MIG) KD × $10^{-9}$ (nM) | Affinity (w/ITAC) KD × $10^{-9}$ (nM) |
|---|---|---|---|---|---|---|---|
| IP10.1 | 2374 | 8.53 | 0.80 | 0.68 | 14.9 | No binding | No binding |
| IP10.44 | 3007 | 0.01 | 1.16 | 0.001 | 0.20 | 168 | No binding |
| IP10.45 | 3010 | 0.44 | 1.19 | 0.06 | 4.74 | No binding | No binding |
| IP10.46 | 3016 | 0.11 | 0.96 | 0.01 | 0.19 | 77.5 | No binding |
| IP10.52 | 3002 | 0.04 | 1.30 | 0.005 | 1.43 | 73.5 | No binding |
| IP10.53 | 3017 | 0.51 | 0.59 | 0.03 | 0.22 | 54.3 | No binding |

2. Epitope Mapping a. Hydrogen/Deuterium Exchange Mass Spectrometry (HDX-MS)

HDX-MS method probes protein conformation and conformational dynamics in solution by monitoring the rate and extent of deuterium exchange of backbone amide hydrogen atoms. The level of HDX depends on the solvent accessibility of backbone amide hydrogen atoms and the protein hydrogen bonds. The mass increase of the protein upon HDX can be precisely measured by MS. When this technique is paired with enzymatic digestion, structure features at the peptide level can be resolved, enabling differentiation of surface exposed peptides from those folded inside. Typically, the deuterium labeling and subsequent quenching experiments are performed, followed by online pepsin digestion, peptide separation, and MS analysis.

Epitope mapping was performed on IP-10 with anti-IP10 mAbs IP10.44 and IP10.1. Prior to epitope mapping experiments, non-deuteriated experiments were carried out to generate a list of common peptic peptides for recombinant full length human IP-10 (20 μM) and protein complex of recombinant IP-10 and anti-IP-10 mAb (1:1 molar ratio), achieving 100% sequence coverage for IP10. In the HDX-MS experiment, 5 μL of each sample (IP-10 or IP-10 with mAb) was diluted into 55 μL of D$_2$O buffer (10 mM phosphate buffer, D$_2$O, pD 7.0) to start the labeling reactions. The reactions were carried out for different periods of time as follows: 20 seconds; 1 minute; 10 minutes; and 240 minutes. By the end of each labeling reaction period, the reaction was quenched by adding quenching buffer (100 mM phosphate buffer with 4M GdnCl and 0.4M TCEP, pH 2.5, 1:1, v/v) and 50 μL of quenched sample was injected into Waters® HDX-MS system for analysis. The deuterium uptake levels of common peptic peptides were monitored in the absence/presence of anti-IP10 mAbs.

HDX-MS measurements on IP10.44 in IP-10 show that it has epitopes comprised of the same peptide regions as IP10.1 as follows:

```
Peptide region 1 (13-18):
                            (SEQ ID NO: 163)
SISNQP Peptide region 2 (19-27):
                            (SEQ ID NO: 164)
VNPRSLEKL
```

-continued
```
Peptide region 3 (29-43):
                            (SEQ ID NO: 165)
IIPASQFCPRVEIIA
```

The changes in deuterium uptake for these peptide regions can be ranked as region 3>1≈2 with region 3 having the most significant changes in deuterium uptake, and region 1 and 2 having the least significant changes in deuterium uptake.

Competition experiments confirmed that the IP10.44 competes for binding to IP-10 with IP10.1 suggesting that it binds to the same epitope as that of IP10.1 and (like IP10.1) does not cross-react with human MIG or human ITAC (as defined herein).

b. Crystallography

Methods

Crystals were grown from a pre-formed complex of IP10 and IP10.44 Fab. The protein concentration was approximately 6 mg/ml in 50 mM Tris-HCl, pH 8, 150 mM NaCl. This was mixed with at a ratio of 1:2 with well solution that consisted of 100 mM Tris-Maleic acid, pH 5.0, 18% (w:v) PEG 3350 and crystals were grown by hanging drop vapor diffusion. Crystals were cryo-protected in a solution that was 75% well solution and 25% glycerol.

Data were collected at beamline 17-ID (IMCA-CAT) at the Advanced Photon Source outside of Chicago, Ill. using a Pilatus 6M detector. The crystal temperature was maintained at 100 K. The data were collected as 900 images in 0.2° wedges for a 180° sweep of data. The data were processed with autoPROC, which uses XDS (Kabsch, 2010a,b) for integration and AIMLESS (Evans & Murshudov, 2013) for scaling and yielded the following statistics:

TABLE 4

Space Group: P2$_1$; Unit Cell: a = 53.6 Å; b = 86.8 Å; c = 133.5 Å; β = 98.8°. Mosaicity 0.29-0.41.

| 2015-4541 | Resolution | Measured | Unique | Redun. | % Comp | R-val | I/σ$_I$ | CC½ |
|---|---|---|---|---|---|---|---|---|
| Overall | 52.01-2.23 | 108138 | 57281 | 1.9 | 96.7 | 0.028 | 16.3 | 0.999 |
| First Shell | 52.02-3.88 | 20621 | 10961 | 1.9 | 95.4 | 0.015 | 40.1 | 0.999 |
| Last Shell | 2.73-2.23 | 49325 | 26114 | 1.9 | 97.1 | 0.168 | 4.1 | 0.963 |

Molecular replacement used the program PHASER and models derived from the IP10/Fab structure, which consisted of three parts, the Fv (VL and VH domains) without the CDRs and with residues that changed mutated to either Gly or Ala, CL:CH1 domain dimer, and the IP10 dimer (as shown in Table 5), which at every step met PHASER's criteria for having successfully placed a component, which is at least at TFZ score of at least 6 in space group P2$_1$ for the first component and at least 8 for other components.

TABLE 5

| Model | RFZ | TFZ | PAK | LLG | ΔLLG | LLG + | ref-TFZ | ref-LLG | Δref-LLG |
|---|---|---|---|---|---|---|---|---|---|
| Fv | 8.9 | 7.3 | 0 | 115 |  |  | 8.9 |  |  |
| Fv | 3.6 | 8.6 | 0 | 103 | −12 |  | 11.1 |  |  |
| clch1 | 5.0 | 9.3 | 1 | 200 | 97 | 200 | 11.8 |  |  |
| clch1 |  | & | 2 | 6345 |  | 295 | 56.3 |  |  |
| ip10 dimer | 2.4 | 9.3 | 2 | 361 | −5984 |  | 47.5 | 7809 | 7448 |

The resulting electron density maps showed electron density for residues and side chains missing from the model. The structure was completed using the COOT molecular graphics program (Emsley et al., 2010) and BUSTER refinement (Blanc et al. 2004 and GlobalPhasing, Ltd.).

Results

The structure of the IP10/IP10.44 Fab complex was determined at 2.23 Å resolution. The most prominent feature on the surface of IP10 is a protrusion consisting of the side chains Ile 12, Ser 13, and Ile 14 (data not shown). This inserts into an orifice created by the long CDR-H3 and between it and CDRs-H1 and H2. A relative depression on the IP10 to the right of the residues 12-14 protrusion is where the extended CDR-H3 binds (data not shown).

Residues on IP10 that are involved in the epitopes for both IP10.1 and IP10.44 as defined by in contact (S. Sheriff et al. 1987; Sheriff, 1993) are: Val 7, Cys 9, Thr 10, Cys 11, Ile 12, Ser 13, Ile 14, Ser 15, Asn 16, Pro 37, Arg 38, Lys 47, Gly 49, Glu 50, Lys 51, Arg 52, Cys 53.

3. Stability

IP10.44 shows high thermal stability and thermal reversibility with first melting temperature at 70.2° C. (TM1 for IP10.1 at 64° C.) and thermal reversibility of 41.2% at 73° C.

Stable CHO pools expressing IP10.44 were used to produce 8 batches of IP10.44 at approximately 20 L scale. The expression level at this stage of cell culture was approximately 50 mg/L and the purification yields were 60-70% using a one step Protein-A purification method. The antibody was formulated in buffer (20 mM histidine and 10% sucrose pH6) and tested for identity, purity, heterogeneity and glycosylation by various methods. —The results confirmed the identity of the antibody and the purity was >97% monomeric fraction as seen by size exclusion chromatography. The heterogeneity and glycosylation are typical of what is expected for a human IgG1 antibody.

TABLE 6

Physical Stability

| Clone | Lot | Tm1 | Tm2 | Tm3 | % reversibility (73° C.) | C50 (Gdn unfolding) |
|---|---|---|---|---|---|---|
| IP10.1 | 2374 | 64.0 | 70.9 | 82.3 | 0.6 | 2.46 |
| IP10.44 | 3007 | 70.2 | 74.4 | 82.9 | 41.2 | 2.36 |
| IP10.45 | 3010 | 71.7 | 75.3 | 82.8 | 61.1 | 2.40 |
| IP10.46 | 3016 | 71.9 | 73.2 | 82.2 | 39.0 | 2.46 |
| IP10.52 | 3002 | 71.1 | 73.4 | 82.7 | 60.0 | 2.44 |
| IP10.53 | 3017 | 71.7 | 73.7 | 82.1 | 65.0 | 1.85 |

B. Cell-Based Activity of IP10.44

Biacore®-based kinetic analysis demonstrated superior $K_D$ of IP10.44 to IP10.1, which is primarily driven by improvement in dissociation constant (koff). The estimated t½ (half-life of IP-10 association) is approximately 3 hours for IP10.1, while that for IP10.44 is >100 hrs. Thus, the existing assays (calcium flux, chemotaxis) which have a duration of <two hours and require concentration (>10 nM) of exogenous IP-10 that are significantly higher than the $K_D$ of either antibody, would not be expected to differentiate these two antibodies. To allow for such differentiation, a new cellular assay was developed whose duration lasted≥24 hours with a robust signal/noise ratio that can be induced at IP-10 levels that are similar to or lower than $K_D$ of either antibody and more closely resemble the IP-10 concentration in IBD patients (approximately 2-digit pM). Such assays were developed by taking a two-pronged approach: 1) optimization of existing assays in which anti-IP-10 Ab and IP-10 are pre-incubated for ≥24 hours before addition to cells and addition of low levels (<100 pM) IP-10 (exogenous) provides robust signal/noise ratio; 2) identification of new assays in which a cell function is mediated by approximately 2-digit pM endogenous IP-10 induced by inflammatory stimuli for at least 24 hours. For the first approach, two assays were used: inhibition of I125-IP-10 (20 pM) binding to whole cell (CXCR3-expressing B cell line, and gut epithelial cell line). For the second approach, two additional assays were used: measurement of IL-6 secretion by hPBMCs treated with IFNγ/α or IFNγ/α/IL-10/LPS for 24 hours, and measurement of IL-12p40 secretion by hPBMCs stimulated sequentially first by IFNγ for 24 hours and then by LPS for another 24 hours.

In these newly established cell-based assays, IP10.44 demonstrated superior activity to IP10.1. For example, in whole cell binding assays, IP10.44 exhibits at least 5-fold better potency than IP10.1 in blocking exogenous IP-10 binding to its target cells, including CXCR3-expressing cells (CXCR3/300.19) and gut epithelial cells (KM12SM).

Additionally, IP10.44 showed approximately 6-fold better potency than IP10.1 in inhibiting endogenous IP-10-mediated IL-6 secretion by hPBMCs stimulated with IFNα/γ. Similarly, IP10.44 inhibited endogenous IP-10-mediated IL-12p40 secretion by hPBMCs stimulated with IFNγ/LPS, with 4-fold greater potency relative to IP10.1, and significantly better maximal inhibition (approximately 100% with IP10.44 vs. approximately 75% with IP10.1) as shown in Table 7.

TABLE 7

| Assay | | Potency nM (range) | |
|---|---|---|---|
| | | Eldelumab | BMS-986184 |
| Exogenous $I^{125}$-1P-10 binding to whole cell | CXCR3-expressing B cell line | 0.7 (0.5-1.2) | 0.1 (0.05-0.2) |
| | Gut epithelial cell line (KM12SM) | 1.2 | 0.2 |
| EndogenousIP-10-mediated cell function in hPBMC | IFNα/γ-induced IL-6 | 2.4 (1.3-4.1) | 0.4 (0.2-0.6) |
| | IENγ/LPS-induced IL-12p70 | 0.8 (0.4-1.3) (max inhibition: 75%) | 0.2 (0.1-0.4) (max inhibition: ~100%) |

Mechanistic studies using the hPBMC-based assays, demonstrate that monocytes are the primary cellular source of IP-10, IL-6 and IL-12p40. Importantly, in support of the observed superior cellular activities of IP10.44 in these in vitro assays, high-affinity anti-IP-10 mouse surrogate for IP10.44 showed superior inhibition of IL-6 and IL-12p40 in blood than low affinity murine surrogate for IP10.1 in an innate immune colitis induced by CD40 in SCID (TB cell-deficient) mice (see below).

C. In Vivo Activity

1. Target Engagement (TE)

IP10.44 was tested for the ability to provide long-term suppression of free IP-10 in cynos. Two sensitive LC-MS-based assays were established to specifically measure free IP-10 levels in serum of cynos, and further qualified using samples spiked with IP10.44 and IP10.1. Using these assays time-dependent changes in free IP-10 levels were measured in serum of cynos dosed with these two antibodies at 10 mg/kg, respectively, relative to those dosed with vehicle. IP10.1 reduced free IP-10 transiently for 6 hours after dosing and then increased it up to 6-fold for a duration of 10 days, whereas, in sharp contrast, IP10.44 completely suppressed free IP-10 up to 10 days (FIG. 14). These data demonstrate that IP10.44 is superior to IP10.1 in target engagement in circulation.

2. PK/PD (Pharmacokinetic and Pharmacodynamic Parameters)

Figure 15:
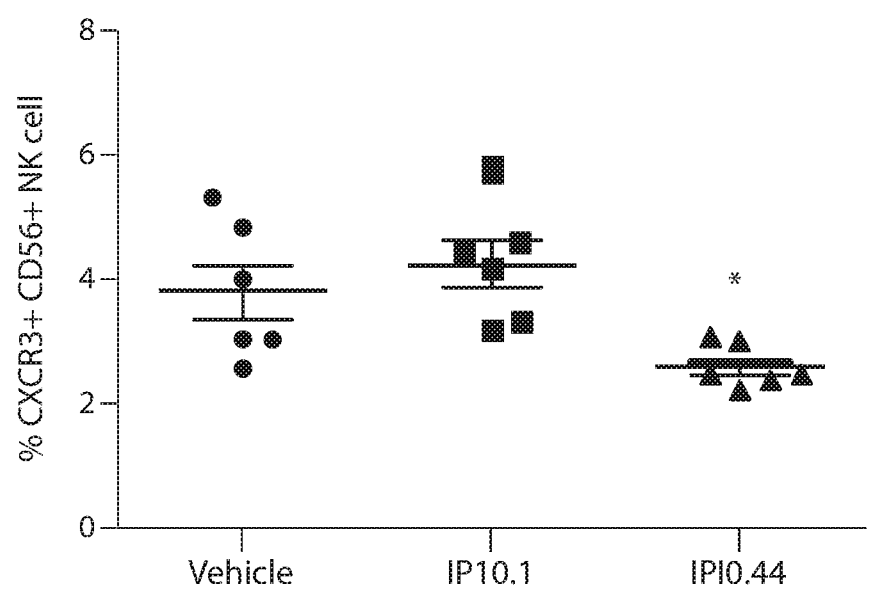
FIG. 15 is a graph showing the activity of antibodies IP10.1 and IP10.44 in reducing NK cell frequency.

Absence of CXCR3 signaling on NK cells in naive setting has been reported to reduce their frequency in the circulation and lymphoid organs based on studies with CXCR3 KO mice. Internal studies have shown that a high-affinity anti-IP-10 mouse surrogate, but not a low-affinity one, significantly reduces CXCR3+NK cell frequency in blood and spleen in naive mice, thus identifying the NK cell subset as a potential PD biomarker for inhibiting signaling at CXCR3 by IP-10. Leveraging this finding and considering that neither IP10.44 nor IP10.1 cross-reacts with mouse IP-10, the effect of these two antibodies on human CXCR3+NK frequency in blood and spleen of NSG/HSC mouse (a mouse strain which is naturally deficient in mouse T/B/NK cells and can be replenished with human T/B/NK cells by reconstitution with human hematopoietic stem cells (HSCs) to create a mouse with a 'humanized' immune system) was tested. IP10.44, but not IP10.1, significantly reduces human CXCR3+NK cell frequency in spleens of these mice dosed at 50 mg/kg (dose selected to maximize target coverage based on the sub-optimal PK of the two human antibodies in NSG mice) (FIG. 15). No significant effect of either antibody on CXCR3+NK cell in blood was observed in this study, presumably due to the low frequency of this cell population in circulation resulting from old age (>6 month post reconstitution).

3. IBD Models

Efficacy in IBD models was tested. Neither IP10.44 nor IP10.1 cross-reacts with mouse IP-10, rendering mouse unsuitable for directly testing these molecules in experimental colitis models. Therefore, two anti-mouse IP-10 surrogate antibodies were identified, i.e., antibodies 18G2 and 6A1, the affinities of which are comparable to IP10.44 and IP10.1, respectively. In cell-based assays 18G2 showed approximately 8-fold better potency than 6A1 in inhibiting mouse IP-10-induced calcium flux in CXCR3/300.19 cell line. In vivo PD studies showed that 18G2 is superior to 6A1 in reducing CXCR3+NK cell frequency and number in blood in naive mice.

Figure 16A:
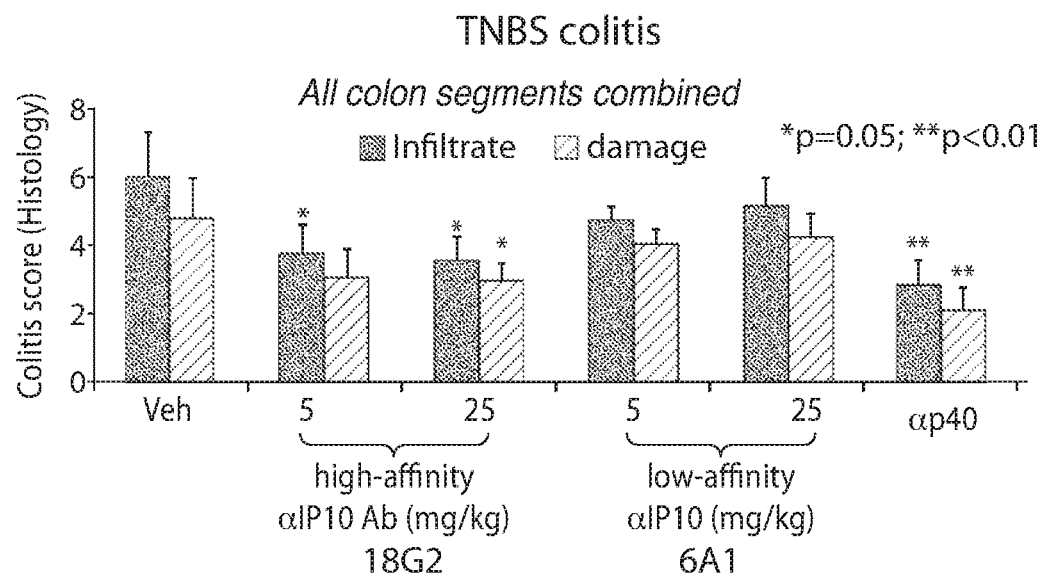
FIG. 16A and FIG. 16B (TNBS colitis), and FIG. 16C (CD40-induced colitis) are graphs showing the efficacy of antibody surrogates of IP10.1 (6A1) and IP10.44 (18G2) in two distinct colitis models.
Figure 16B:
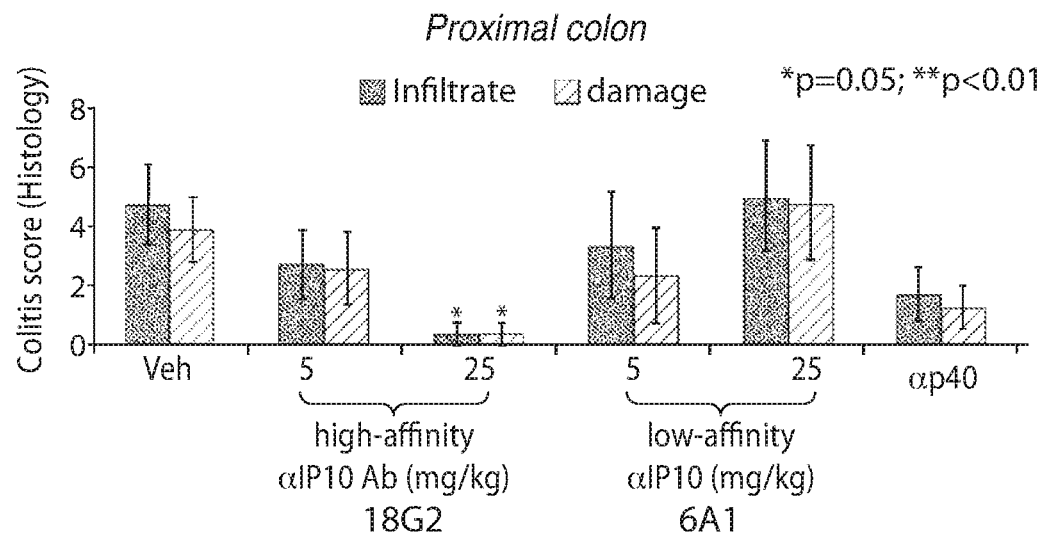
Figure 16C:
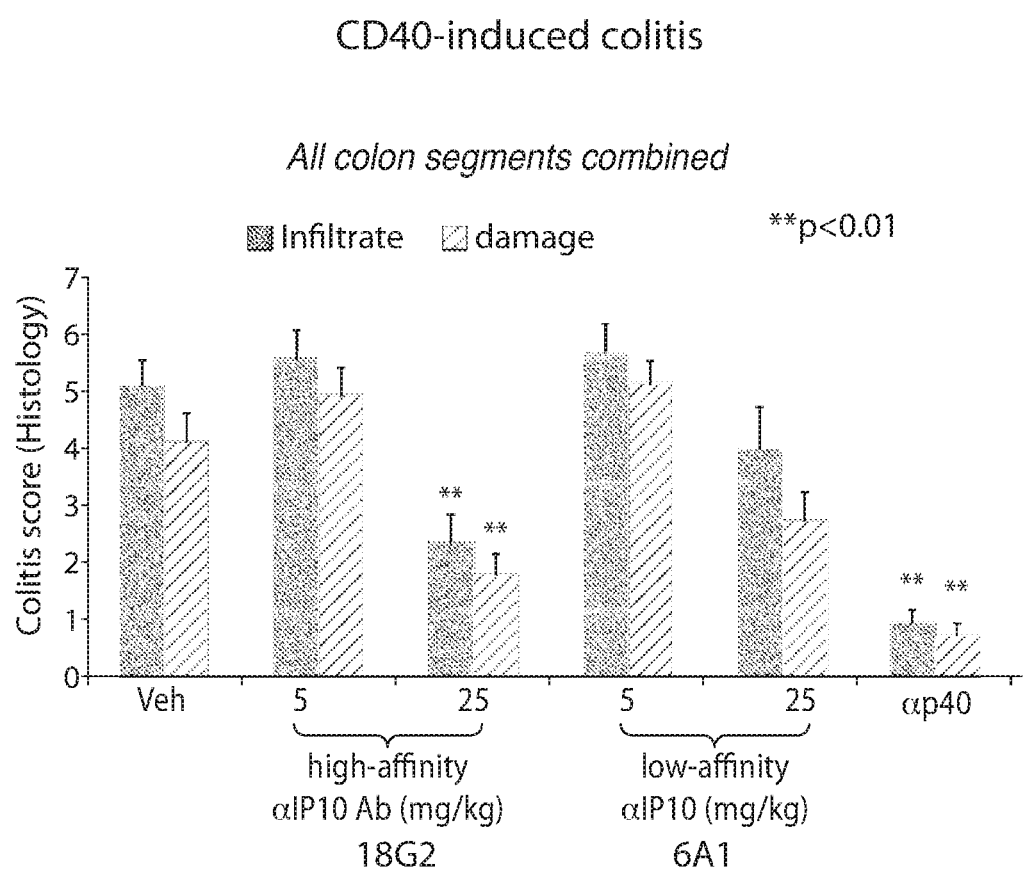
Figure 17A:
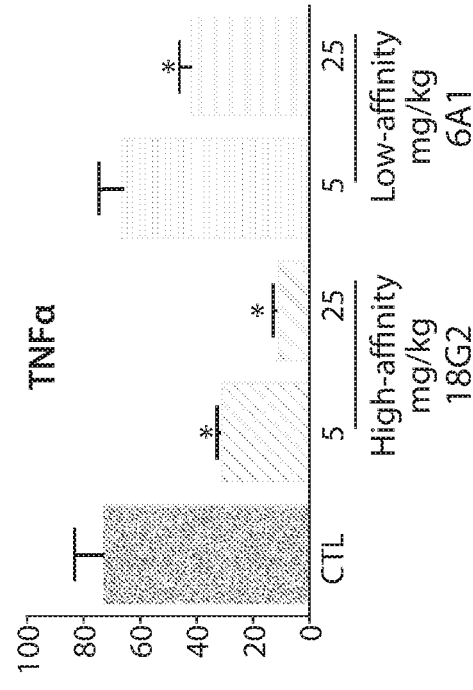
FIG. 17A (IFNγ), FIG. 17B (TNFα), FIG. 17C (IL-12p40), and FIG. 17D (IL-6) are graphs showing the activity of antibody surrogates of IP10.1 (6A1) and IP10.44 (18G2) to reduce circulating levels of cytokines in the CD40-induced colitis model.
Figure 17B:
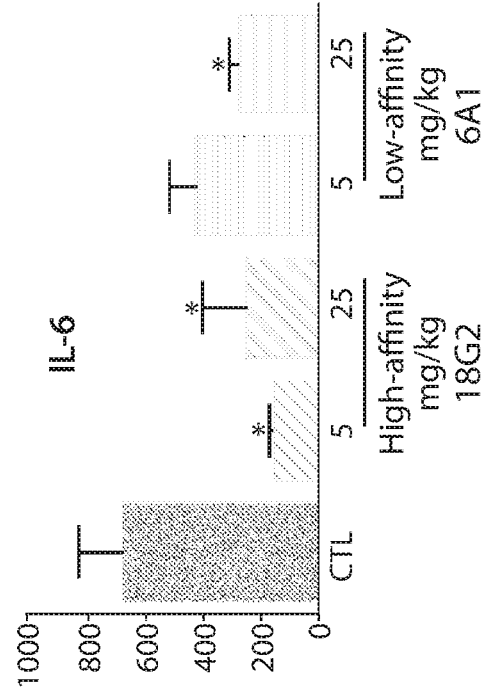
Figure 17C:
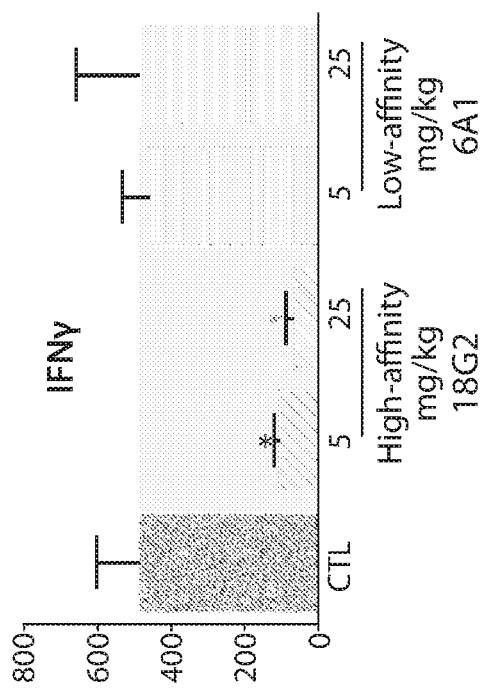
Figure 17D:
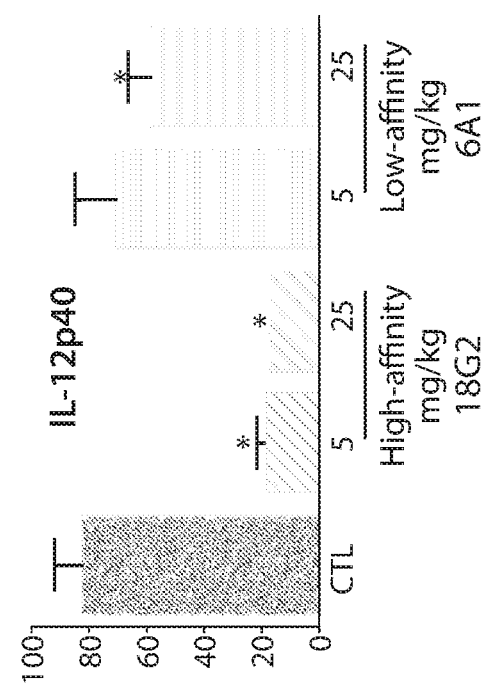

The two surrogates were tested in two distinct models of colitis, one induced by TNBS in wild-type mice, whose pathogenesis involves both innate and adaptive immunity, and the other induced by CD40 in SCID (TB-deficient) mice, whose pathogenesis involves only innate immunity. In both models, anti-p40 antibody has been shown to be efficacious in reducing the disease, thus serving as a positive control. Importantly, the high affinity surrogate 18G2 exhibits significantly better efficacy than IP10.1 surrogate 6A1 (FIG. 16A, FIG. 16B and FIG. 16C). This superiority is not due to differences in PK/exposures in that 6A1 has >2-fold higher exposure than 18G2 at terminal trough. Therefore this data suggests that the increased affinity observed with IP10.44 relative to IP10.1 can translate into greater efficacy in the context of gut inflammation driven by both innate and adaptive immunity.

Since CD40-induced mouse colitis is a more robust model involving significant systemic inflammation, the effect of height affinity 18G2 vs. low affinity 6A1 on levels of circulating pro-inflammatory cytokines was also evaluated. Consistent with its superiority in efficacy to 6A1, 18G2 reduces more robustly the circulating levels of several cytokines including IFNγ, IL-12p40, IL-6, TNFα, MCP-1, and RANTES (FIG. 17A, FIG. 17B, FIG. 17C and FIG. 17D). A separate study with high affinity surrogate, 18G2, in this model showed a correlation in the reduction of a subset of cytokines, including IFNγ, IL-12p40, IL-6 and TNFα, between blood and the inflamed gut.

Figure 22:
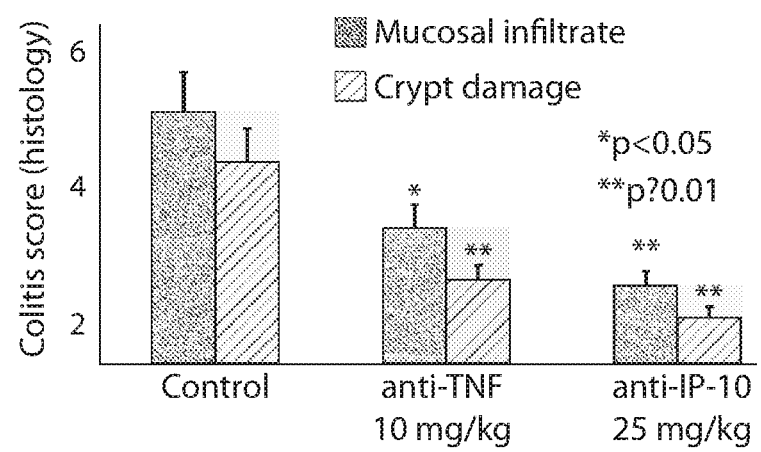
FIG. 22 is a graph comparing the high affinity anti-IP-10 mouse surrogate (18G2) with the anti-TNFα surrogate.

To determine if targeting IP-10 can be differentiated from targeting TNFα, representing the standard care for IBD, in their mechanisms of action, the SCID mouse model of CD40-induced colitis was used. This model was chosen because of abundant presence of IP-10 and TNFα in circulation and in the gut, and of the deomonstrated efficacy of both anti-IP-10 and anti-TNFα antibodies. In a comparative study on high affinity anti-IP-10 mouse surrogate (18G2) vs. anti-TNFα surrogate in this model, both antibodies showed significant efficacy (FIG. 22).

Importantly, multiplex cytokine analysis reveals clear differences between these two interventions in reducing pro-inflammatory cytokines in serum and in the inflamed gut, suggesting the mechanisms for achieving their efficacy can be differentiated. Relative to anti-TNFα surrogate, 18G2 significantly reduces serum levels of IFNγ, IL-12p40, IL-6, RANTES, and MIP1beta and colonic levels of INFγ, IL-12p40, IL-6, IL-17 and IL-22, as measured by luminex-based multiplex cytokine assays (FIG. 18A, FIG. 18B, FIG. 18C, FIG. 18D, FIG. 18E and FIG. 18F).

Taken together, these data indicate that targeting IP-10 can be differentiated mechanistically from targeting TNFα in systemic and local inflammatory setting in experimental colitis. Furthermore, 18G2 robustly reduces TNFα in circulation and in the inflamed gut, whereas anti-TNFα had little effect on IP-10 levels in either compartment, thus providing another piece of evidence on differentiating between the two interventions in experimental colitis.

D. Immunogenicity

Immunogenecity of IP10.44 was assessed using an in vitro T cell proliferation assay and was compared to the immunogenicity of IP10.1 in the same assay. IP10.44 showed 20-25% immunogenicity as compared to 7-10% immunogenicity for IP10.1.

E. Pharmacokinetics and Pharmacodynamics in Cynomolgus Monkeys

IP10.44 exhibited nonlinear PK in cynomolgus monkeys (data not shown). Free drug assay was used for both IP10.44 and IP10.1. With an increase in dose from 0.5 to 10 mg/kg, the total body serum clearance (CLTs) of IP10.44 decreased by about 4-fold, but the volume of distribution at steady state (Vss) remained similar. As a result, the T-1/2 increased by about 5-fold. This is consistent with the nonlinear PK of IP10.1 in both monkeys and humans. The CLTs of IP10.44 was 2-fold higher than that of IP10.1 at 0.5 mg/kg. It may be hypothesized that the nonlinear PK is caused by target-mediated drug disposition (TMDD) and higher binding affinity of IP10.44 renders higher clearance at lower doses when the target is not saturated. The PK comparison of IP10.44 and IP10.1 at higher doses, however, showed conflicting results: the CLTs values for the two antibodies were similar at 10 mg/kg, but the CLTs of IP10.44 was 2.7-fold higher than that of IP10.1 at 20 mg/kg.

Figure 19A:
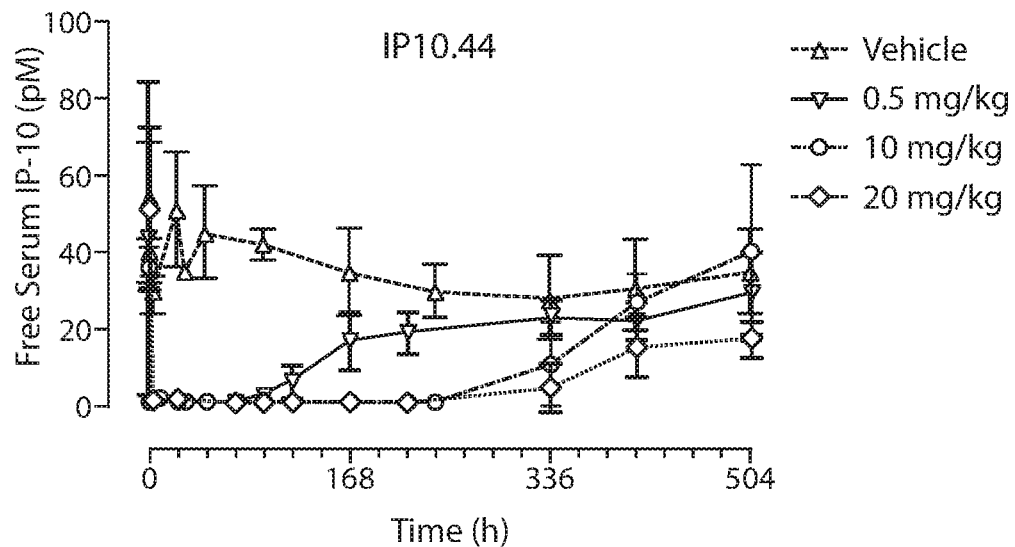
FIG. 19A (IP10.44) and FIG. 19B (IP10.1) are graphs showing temporal profiles of free serum IP-10 following an intravenous dose of IP10.44 and IP10.1.
Figure 19B:
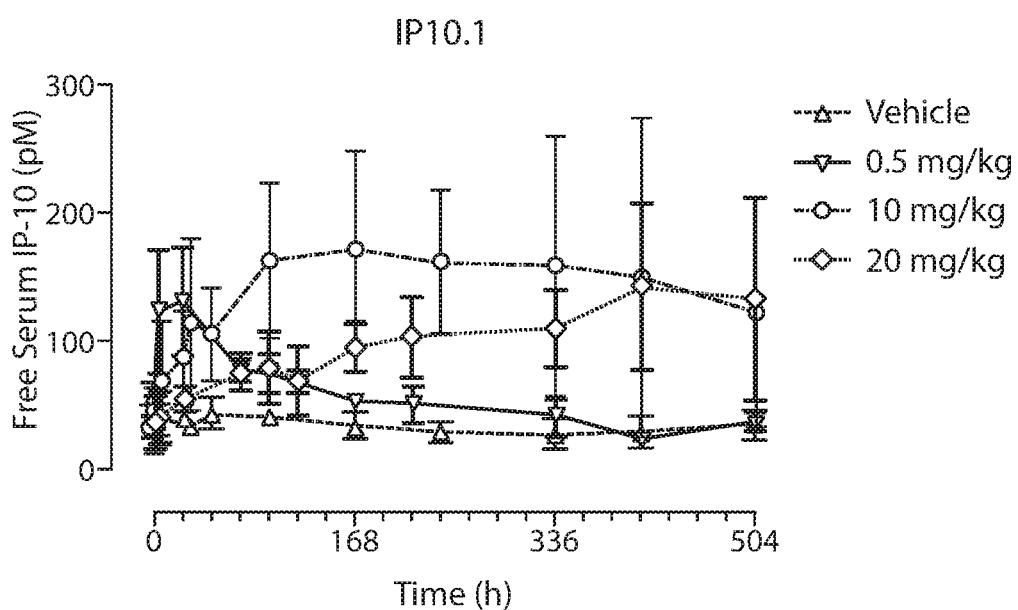
Figure 20:
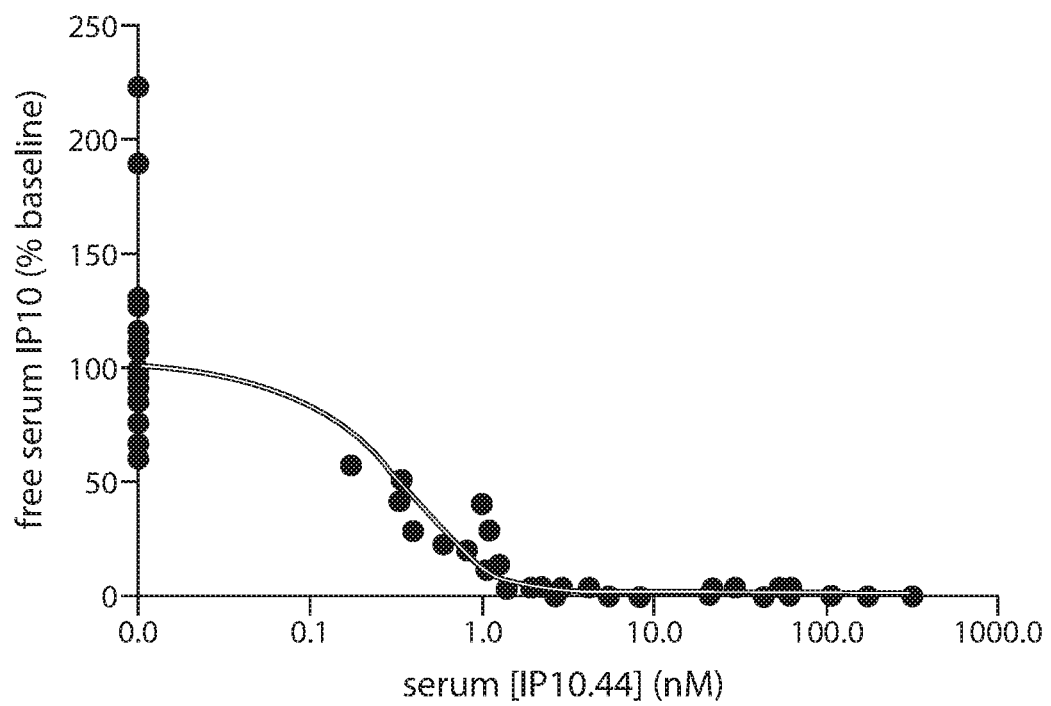
FIG. 20 is a graph showing free serum IP-10 Suppression (% Baseline) compared to serum IP10.44 in cynomolgus monkeys.
Figure 21A:
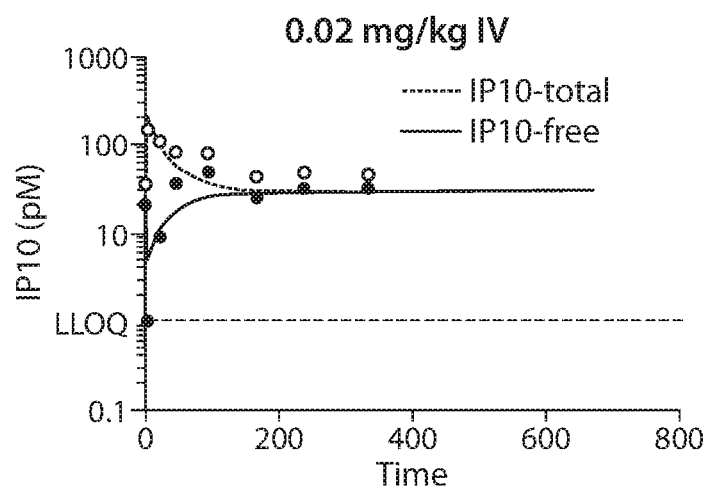
FIG. 21A, FIG. 21B, FIG. 21C, FIG. 21D, FIG. 21E and FIG. 21F are graphs showing the observed versus predicted free and total serum IP-10 by PK/PD modeling (LLOQ of 1 pM for free serum IP-10; if a value is below LLOQ, LLOQ was used for plotting).
Figure 21B:
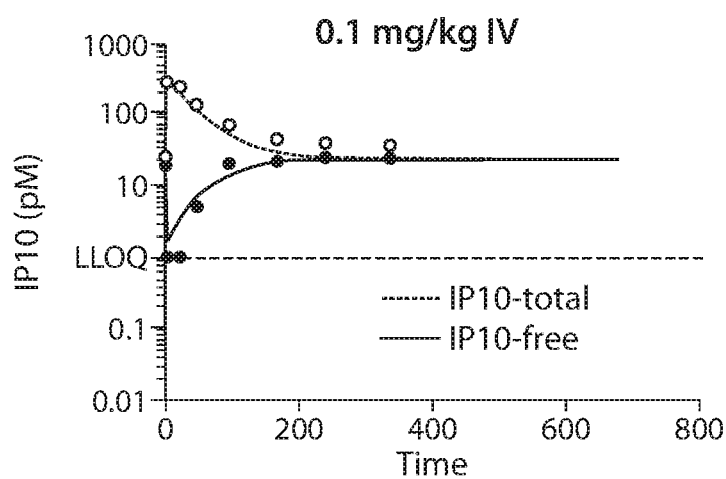
Figure 21C:
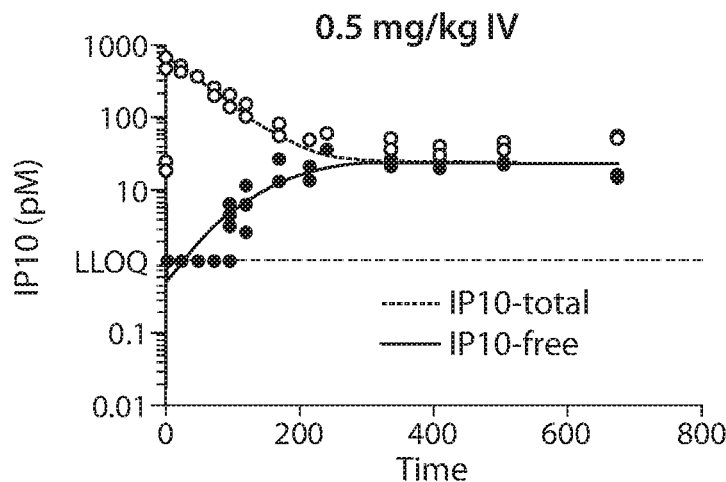
Figure 21D:
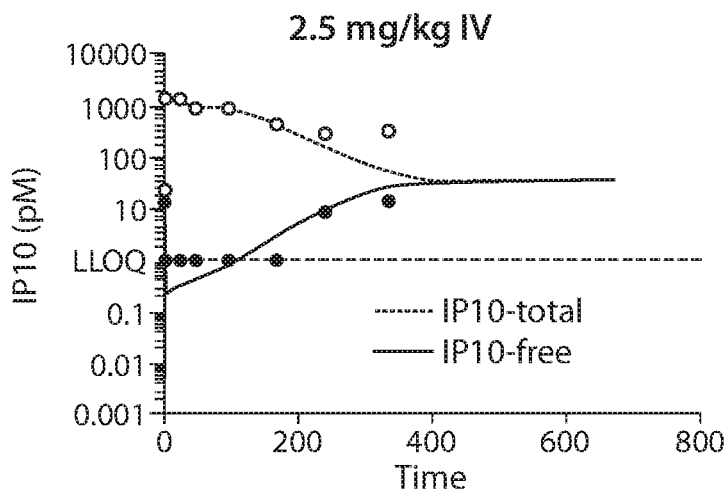
Figure 21E:
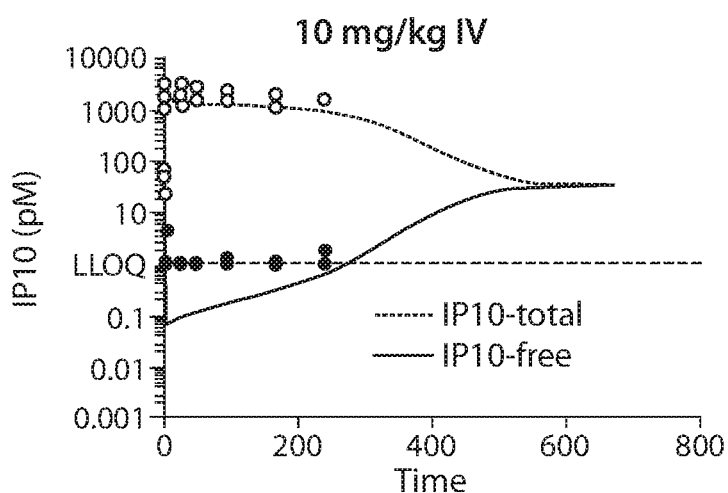
Figure 21F:
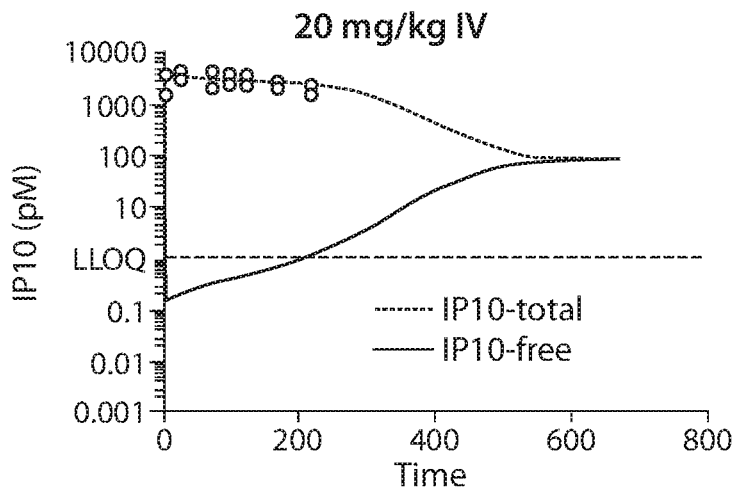

IP10.44 demonstrated superiority to IP10.1 in suppressing free serum IP-10 levels (FIG. 19A and FIG. 19B). Following an IV bolus dose, IP10.44 showed dose-dependent suppression of free serum IP-10 and the duration of complete suppression, defined by the suppression of free IP-10 from the baseline levels (approximately 40 pM) to below LLOQ (1 pM), was approximately 3 days for 0.5 mg/kg and approximately 10 days at 10 mg/kg. The rapid rebound of free serum IP-10 (back to baseline on day 17) was possibly caused by the accelerated drug decay due to ADA. IP10.1 at a dose as high as 20 mg/kg, on the other hand, did not to suppress free serum IP-10 but elevated free serum IP-10 above the baseline levels (maximum increase by 7-fold) and this is consistent to what was observed in the clinic. The simple regression of free serum IP-10 suppression vs. free drug concentration of IP10.44 revealed an IC50 of 223±88 pM (FIG. 20). Furthermore, PK/PD modeling on free drug PK, free and total serum IP-10 data in monkeys estimated in vivo Kd of 43±6 pM for IP10.44, approximately 150-fold more potent than that of IP10.1 (in vivo Kd of 6.5±1.1 nM) in monkeys (FIG. 21A, FIG. 21B, FIG. 21C, FIG. 21D, FIG. 21E and FIG. 21F).

In addition, following an IV dose of IP10.44 or IP10.1, a rapid increase of total serum IP-10 was observed with Tmax of 4 to 30 hours. The magnitude of total IP-10 increase was dose-dependent and the maximum increase was up to 5 nM for IP10.44 and up to 12 nM for IP10.1, representing >100 fold increase relative to the baseline level (approximately 40 pM).

In summary, IP10.44 demonstrated superior in vivo $K_D$ (approximately 150-fold) to IP10.1 in the suppression of free serum IP-10 (in vivo $K_D$ of 43±6 pM vs. 6.5±1.1 nM) in cynomolgus monkeys. IP10.1 increased the free serum IP-10 level (>5-fold) above the baseline in both monkeys and humans, while IP10.44 (following IV administration to monkeys) showed a sustained and complete (<LLOQ of 1 pM) suppression of free serum IP-10 for approximately 3 days at 0.5 mg/kg and approximately 10 days at 10 mg/kg. A free drug assay was used to characterize the PK of IP10.44 in monkeys. IP10.44 exhibited a nonlinear PK in monkeys, likely resulting from target-mediated drug disposition. This is similar to the nonlinear PK of IP10.1 observed in monkeys and humans. Compared to IP10.1, higher affinity of IP10.44 to IP-10 led to relatively shorter half-life (T-1/2) in monkeys. The human T-1/2 of IP10.44 at 1 and 10 mg/kg was predicted to be approximately 2 and approximately 6 days, respectively. At the same doses, the corresponding human T-1/2 of IP10.1 was approximately 4 and approximately 8 days, respectively. The subcutaneous bioavailability (70%) of IP10.44 in humans was assumed to be the same as that of IP10.1. Based on the preclinical PK/PD information, the human dose of IP10.44, administered subcutaneously every two weeks, was projected to be 120 mg/70 kg. At this dose, the free serum IP-10 level corresponding to the 90th percentile of the UC patient population was reduced by 80% to the 10th percentile of healthy subjects.

No adverse effects were observed in the cynomolgus PK/PD studies up to a single IV bolus dose of 20 mg/kg. Overall, IP10.44 demonstrated acceptable PK/PD properties and safety profile.

Example 3

(A) Single Ascending Dose Study (SAD) and Multiple Dose Study (MAD) Regarding Safety, Tolerability, Pharmacokinetics, and Target Engagement of BMS-986184 (IP10.44) in Healthy Subjects and
(B) Evaluation of Safety, Efficacy, Pharmacokinetics, Target Engagement, and Pharmacodynamics of BMS-986184 in Patients with Moderate to Severe Ulcerative Colitis (UC)

Introduction

Figure 23:
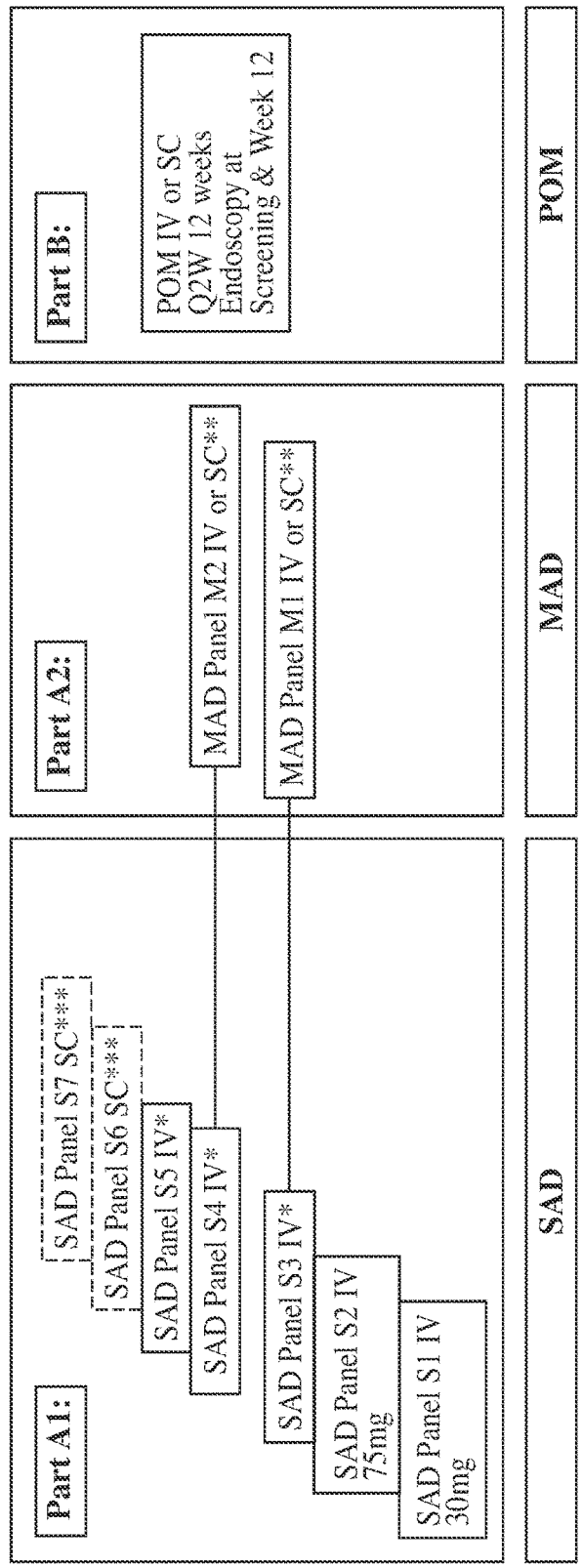
FIG. 23 is a study design schematic.

Part A is a randomized, placebo-controlled, double-blind, single ascending (SAD) and multiple dose (MAD) study to assess the safety, tolerability, pharmacokinetics (PK), and target engagement (TE) of BMS-986184 in healthy male and female participants. In Part A1 (SAD), there will be up to 5 sequential intravenous (IV) dose panels designated as Panels S 1, S2, S3, S4, and S5. Additionally, there may be up to 2 subcutaneous dose panels designated as panels S6 and S7. The projected doses selected for the SC dose panels (S6 and S7) will not exceed mean exposures observed during the IV dose panels S1-S4. Additional dose panels, to a lower or higher dose than the previous panels, may be added by adaptation. In Part A2 (MAD), there may be up to 2 panels intravenous (IV) or subcutaneous (SC) designated as Panels M1 and M2. Part B, is a randomized, placebo-controlled, double-blind, proof of mechanism (POM) study to evaluate the safety, efficacy, pharmacokinetics, targeted engagement, and pharmacodynamics of BMS-986184 in male and female patients with UC. Part B will begin after evaluation of safety, tolerability, PK, and TE of Part A. The study design schematic is presented in FIG. 23.

Part A

Study Design for SAD/MAD in Healthy Participants (Part A)

In Part A, healthy participants will undergo screening evaluations to determine eligibility. Participants must complete screening procedures within 21 days of Day 1. A ±2 day window visit may be used to accommodate unit and participant's schedules. Participants will be admitted to the clinical facility on the morning of Day −1.

Study Design for SAD in Healthy Participants (Part A1)

There will be 8 healthy male or female participants per sequential SAD dose panel (S1-S7). Each panel will be double-blinded and randomized. For the first dose panel (S1), a sentinel panel will be dosed. One healthy male or female participant will receive a single dose of BMS-986184 and 1 healthy male or female participant will receive a matched placebo. Available safety data (including any reported adverse events, findings from physical exams, any clinical laboratory results, vital signs, and ECGs) from these 2 participants will be evaluated within 24 hours by the Investigator and Sponsor prior to treatment of the remaining participants in the first dose panel (S1). On Day 1, the remaining 6 healthy male or female participants in the first dose panel (S1) will be randomized to receive a single dose of BMS-986184 or a matched placebo in a ratio of 5:1. For each sequential dose panel (S2-S7), on Day 1, 8 healthy male or female participants will be randomized to receive a single dose of BMS-986184 or a matched placebo in a ratio of 3:1 on Day 1. Dose selection criteria are described below.

Study Design for SAD/MAD in Healthy Participants (Part A)

In Part A, healthy participants will undergo screening evaluations to determine eligibility. Participants must complete screening procedures within 21 days of Day 1. A ±2 day window visit may be used to accommodate unit and participant's schedules. Participants will be admitted to the clinical facility on the morning of Day −1.

Study Design for SAD in Healthy Participants (Part A1)

Figure 24:
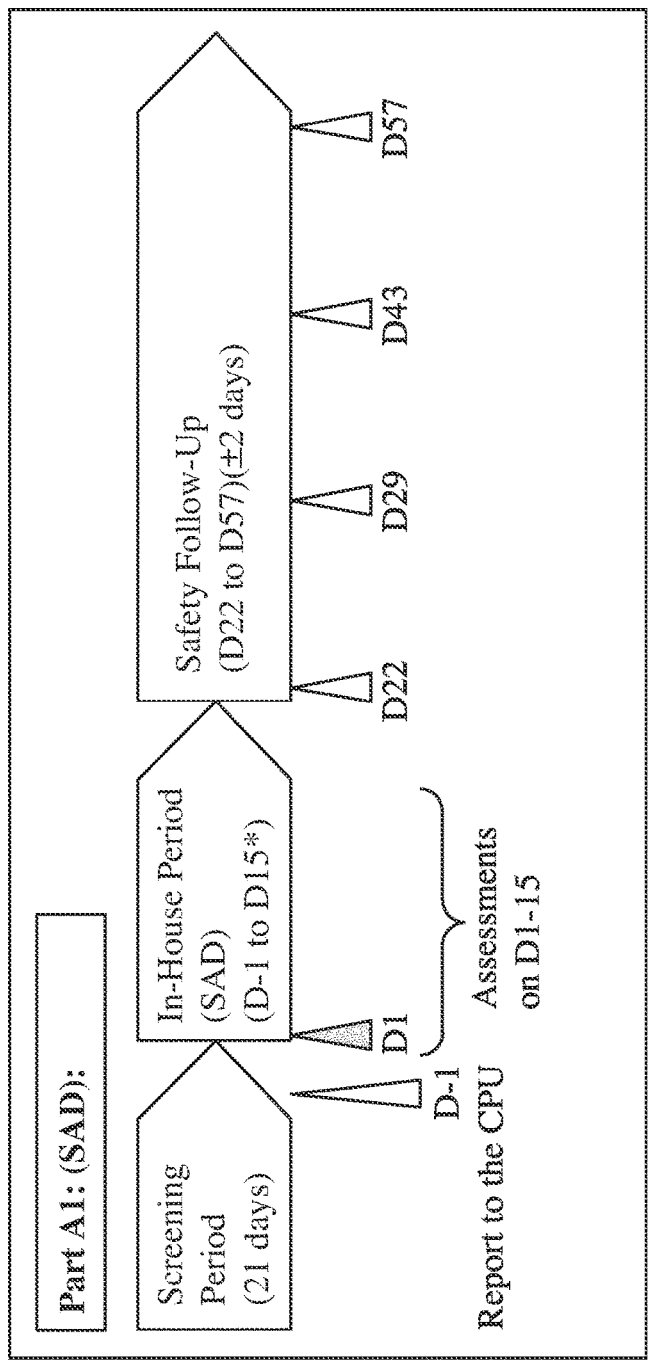
FIG. 24 is a study visit schematic of SAD study in healthy participants (Part A1).

There will be 8 healthy male or female participants per sequential SAD dose panel (S1-S7). Each panel will be double-blinded and randomized. For the first dose panel (S1), a sentinel panel will be dosed. One healthy male or female participant will receive a single dose of BMS-986184 and 1 healthy male or female participant will receive a matched placebo. Available safety data (including any reported adverse events, findings from physical exams, any clinical laboratory results, vital signs, and ECGs) from these 2 participants will be evaluated within 24 hours by the Investigator and Sponsor prior to treatment of the remaining participants in the first dose panel (S1). On Day 1, the remaining 6 healthy male or female participants in the first dose panel (S1) will be randomized to receive a single dose of BMS-986184 or a matched placebo in a ratio of 5:1. For each sequential dose panel (S2-S7), on Day 1, 8 healthy male or female participants will be randomized to receive a single dose of BMS-986184 or a matched placebo in a ratio of 3:1 on Day 1. Dose selection criteria are described in FIG. 24.

Study Design for MAD in Healthy Participants (Part A2)

Figure 25:
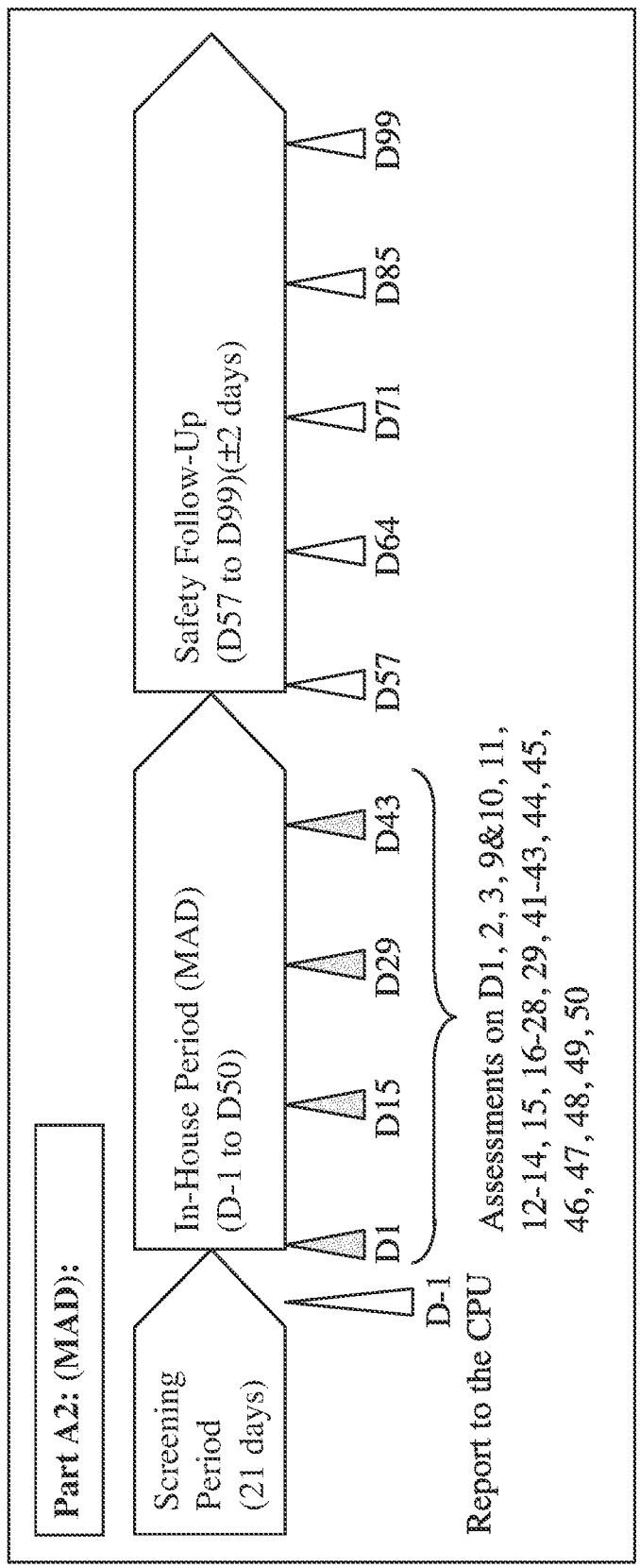
FIG. 25 is a study visit schematic of MAD study in healthy participants (Part A2).

There will be 8 healthy male or female participants per sequential MAD dose panel (M1-M2). On Day 1, these same 8 healthy male or female participants will be randomized to receive BMS-986184 or a matched placebo in a ratio of 3:1 on Day 1. Each panel will be double-blinded and randomized. Dose selection criteria are described below. Participants in the MAD panels (M1 and M2) will remain confined to the clinical facility until furloughed on Day 50. Participants with any ongoing AEs or SAEs at Day 50 should remain at the study site until the Investigator has determined that these events have resolved or have been deemed as not clinically significant. Participants are expected to return to the clinical unit for follow-up assessments on Days 57, 64, 71, 85, and 99. A ±2 day window visit may be used to accommodate unit and participant's schedules. The approximate study duration for Part A2 MAD participants will be up to 120 days. Participants who withdraw early from the study will be requested to complete the study discharge evaluations scheduled to commence on Day 99. Participants who discontinue for reasons other than AEs may be replaced. Up to 16 participants are planned complete Part A2 of the SAD study. Physical examinations, vital sign measurements, ophthalmologic evaluations, 12-lead ECG, and clinical laboratory evaluations will be performed at selected times throughout the dosing interval. Participants will be closely monitored for AEs throughout the study. Blood samples will be collected at selected time points for safety and PK analysis. Approximately 495 mL of blood will be drawn from each participant during Part A2 of the study. The study visit schematic for Part A2 is presented in FIG. 25.

Study Design for POM in Patients with UC (Part B)

There will be up to 36 participants with moderate-to-severe UC in Part B. Part B includes 3 periods: Screening Period, Treatment Period, and Safety Follow-up Period. An additional higher dose panel of 36 participants (24 active: 12 placebo) may be added if the interim analysis shows insufficient target engagement at the projected therapeutic dose, or if intolerable safety events happen, a lower dose panel of 36 participants (24 active: 12 placebo) may be added where the predicted PK exposure is sufficiently lower than the exposure range associated with safety findings. Final determination of the dose volume and administration during the PoM study (Part B) in subjects with UC will be determined once PK and PD data becomes available from the SAD/MAD studies in healthy subjects. The protocol will be amended at that time to include the final dose selection for the PoM study in UC participants. Participants will undergo screening evaluations to determine eligibility. Participants in Part B must complete screening procedures within 28 days of Day 1 (randomization). During the screening period, participants will undergo a physical exam and medical history, smoking history, screening testing procedures, screening endoscopy and laboratory evaluations to confirm active intestinal mucosal inflammation that is due to UC and not due to other causes.

Treatment Period:

On Day 1, up to 36 participants with UC will be randomized to receive a single dose of BMS-986184 or a matched placebo in ratio of 2:1 every other week for a period of 12 weeks (on Days 1, 15, 29, 43, 57, and 71). Part B will be double-blinded and randomized. On Day 85, participants will undergo an endoscopy. For participants experiencing a UC flare during the Treatment Period, every effort should be made to adhere to the study protocol. If in the Investigator's opinion, a participant warrants therapy that is not allowed per study protocol and/or requires hospitalization, then the participant(s) should be treated according to the Investigator's discretion and discontinued from the study. Investigators are strongly encouraged to contact the medical monitor to discuss any participants experiencing a UC flare during the study period.

Figure 26:
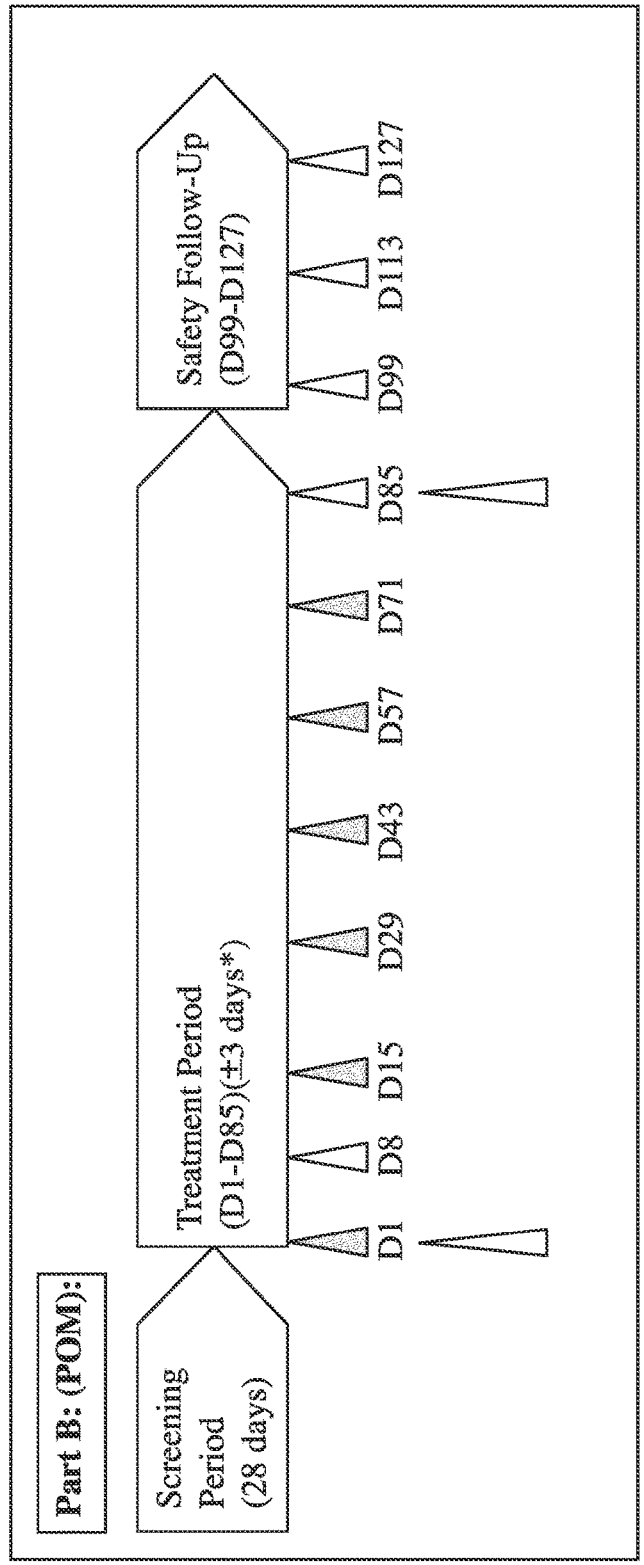
FIG. 26 is a Study visit schematic POM study in patients with UC (Part B).

Safety Follow-Up Period:

Follow up visits will occur every other week for 57 days (on Days 99, 113, and 127). The approximate study duration for Part B participants will be up to 177 days. Participants who discontinue for reasons other than AEs may be replaced. Up to 72 participants are planned. Physical examinations, vital sign measurements, 12-lead ECG, and clinical laboratory evaluations will be performed at selected times throughout the dosing interval. Participants will be closely monitored for AEs throughout the study. Blood samples will be collected at selected time points for safety and PK analysis. Approximately 300 mL of blood will be drawn from each participant during Part B of the study. The study visit schematic for Part B is presented in FIG. 26.

Number of Participants

Up to 72 participants will be randomized across 9 panels (7 SAD panels and 2 MAD panels) in Part A. In Part A1 (SAD), each panel will consist of 8 participants (6 active: 2 placebo). A total of 56 participants will be treated in Part A1 (SAD). An additional 16 participants (6 active: 2 placebo per panel) will be treated in Part A2 (MAD), if the MAD is initiated. Although the number of participants is not based on statistical power considerations, administration of BMS-986184 to 6 participants in each panel provides an 80% probability of observing at least one occurrence of any AE which would occur with 24% incidence in the population from which the sample is drawn. If the incidence of AE is 32%, the probability of observing at least one occurrence of any AE with a sample size of 6 BMS-986184-treated participants is 90% In Part B (POM) of the study, a total of 36 participants will be randomized (24 active: 12 placebo) to receive the targeted therapeutic dose carried from Part A2. An additional higher dose panel of 36 participants (24 active: 12 placebo) may be added if the interim analysis shows insufficient target engagement at the projected therapeutic dose, or if intolerable safety events happen, a lower dose panel of 36 participants (24 active: 12 placebo) may be added where the predicted PK exposure is sufficiently lower than the exposure range associated with safety findings. An additional higher dose panel of 36 participants (24 active: 12 placebo) may be added if the interim analysis shows insufficient target engagement at the projected therapeutic dose, or if intolerable safety events happen, a lower dose panel of 36 participants (24 active: 12 placebo) may be added where the predicted PK exposure is sufficiently lower than the exposure range associated with safety findings, End of Study Definition The date the first participant signs a study-specific informed consent form will be defined as the start of the study. A participant is considered enrolled when the study-specific Informed Consent Form (ICF) is signed. The date the last participant completes the discharge procedure or last follow up visit will be defined as the end of study.

Scientific Rationale for Study Design

There are several reasons to initiate development of BMS-986184 through a FIH study in NHV. It will allow for a safer development path with incremental and gradual dose escalation, before moving into participants with UC. It will precisely establish a therapeutic window, with assessment of a broad range of doses (30 mg up to approximately 450 mg IV and potentially SC) to better inform the therapeutic index. Immunosuppression and infection will be evaluated after a single dose in healthy participants in the absence of disease effects and without the influence of an activated immune system. After completing the SAD and MAD in healthy participants, repeated dosing will be performed in participants with UC.

Justification for Dose

Without previous clinical experience available, dose selection for the FIH study was based on the predicted PK exposure, PK/TE (i.e., free IP-10 in serum) relationship established from non-clinical studies, and safety margin established from animal toxicology studies. Briefly, human PK parameters were estimated using the PK model, addressing non-linear PK in monkeys and subsequent extrapolation to humans. Predicted human PK parameters were used to estimate Cmax and AUCs to calculate safety margin across the dose range being tested in the FIH study. Corresponding PD responses were estimated using the PK/PD model, exploring the relationship between the level of BMS-986184 and the free IP-10 in serum across the dose range being tested in FIH. Predicted PD responses were used to provide the anticipated target engagement at respective dose levels to determine the appropriate range of dose in order to fully explore the relationship between PK and target engagement.

To address translational uncertainty in extrapolation from non-clinical data to humans, dose levels and the number of panels may be adjusted based on the safety, tolerability, and the real-time PK/PD analysis on a continuous basis. The first 2 dose levels in SAD will be fixed (30 and 75 mg). The remaining dose levels in Part A and the entire dose range in Part B may be adjusted to reach the anticipated PK exposure and free IP-10 at respective dose panels based on PK/PD analysis. Additionally, projected PK exposure in the selected SAD dose panel will not exceed the pre-specified safety multiples estimated from Cmax and AUC at NOAEL to ensure the safety of study participants.

Dose Selection Justification for SAD in Healthy Participants (Part A1)

In Part A1, dose escalation decisions will be made using safety, PK, and TE data. Available safety data (including any reported adverse events, findings from physical exams, ophthalmologic exams, any clinical laboratory results, vital signs, and ECGs) from the current dose panel will be evaluated by the Investigator and Sponsor prior to determining dose escalation for the subsequent dose panel. Participants will not be randomized in the subsequent dose panel until the safety data up to Day 15 for all participants from the current dose level are reviewed by the Investigator and the Sponsor, and are determined to demonstrate safety and tolerability. The first and second dose panel (S1 and S2) in Part A1 will be fixed (30 mg and 75 mg), respectively. For the remaining dose panels beyond SAD Panel 2 (S3-S5), dose selection will be guided by PK/PD relationships established in prior dose panels based on the real-time PK/PD analysis using the cumulative data, in addition to safety assessments. The projected placeholder dose range in Part A1 SAD is from 30 mg up to approximately 450 mg.

In Part A1, the SAD portion of the study, the dose range was selected to cover a wide range of exposures to characterize the quantitative relationship between PK and target engagement (i.e., reduction of free IP-10 from baseline in serum) considering the potential non-linear PK due to a target-mediated drug disposition, and to establish a sufficient safety margin in humans to enable patient studies. Due to the observations of TMDD in the monkey models, the IV route of administration was chosen to be studied under single dose conditions of the FIE in an effort to gain a better characterization of the PK at the lower end of the dose range, where nonlinearity is most apparent. Since, the SC administration is desirable for best compliance and convenience in the target patient population, BMS-986184 will also be administered SC in the SAD portion of the study in order to determine the feasibility of SC administration and to develop an appropriate dosing regimen to be tested in subsequent portions of the study.

The magnitude of the starting dose to be administered by IV route was selected considering the toxicology findings from preclinical studies. The maximum recommended starting dose (MRSD) was calculated using the NOAEL dose in monkeys. The NOAEL in monkeys, which is considered the most sensitive species, was 30 mg/kg/week. The MRSD based on the body surface area method, taking into consideration a 10-fold safety margin of NOAEL dose, is approximately 58 mg. Since the predictions from the PK/PD model suggest greater than minimal pharmacological activity at this dose, the MRSD is not appropriate to test as the starting dose in humans. Therefore, the starting dose in the SAD was lowered to 30 mg, such that the predicted free IP-10 reduction from baseline in serum is expected to be 37% (Table 8). The projected safety margins of Cmax and AUC at 30 mg estimated from the exposure at NOAEL are 59 and 322 fold, respectively. The proposed dose escalation scheme is expected to bracket the exposures around the predicted efficacious dose. Assuming that the neutralization (as defined as a reduction of >90%) of free IP-10 at steady state trough is necessary to drive the intended efficacy in patients, the dosing regimens expected to achieve 90% and 95% reduction of free IP-10 at steady state trough are projected to be 180 mg and 300 mg, respectively, administered every 2 weeks (Q2W). Thus, the single-dose escalation of study drug up to 300 mg should be sufficient to characterize the steep portion of the PK/PD profile as well as capture the predicted efficacious dose range. At 300 mg, the projected safety margins of Cmax and AUC estimated from the exposure at NOAEL were 6.4 and 13 fold, respectively (Table 9).

Considering that UC patients may exhibit greater variability in PK as well as in PD, due to differences target load compared to healthy subjects, it may be necessary to test doses greater than 300 mg in SAD to provide sufficient safety information to enable progression of this compound into longer-term clinical studies in UC patients. To that end, the highest proposed dose for the SAD portion of the study will be approximately 450 mg. It is noted that the administration of 450 mg is optional and will depend on the safety, PK, and TE data obtained from the previous SAD panels. If the observed PK and TE data suggest the maximum suppression of free IP-10 at trough can be achieved at lower dose levels, the proposed highest dose will not be explored in SAD study. The projected safety margins of Cmax and AUC for this dose level estimated from the exposure at NOAEL were 4, and 8 fold, respectively (Table 8).

The proposed doses from 30 to 450 mg would ensure a full characterization of the PK/PD, while eliciting a wide exposure range to provide sufficient safety information in order to inform dose selection for subsequent patient studies. Table 9 summarizes the projected exposure in human and subsequent safety margin based on the exposure at NOAEL and LOAEL. Table 8 summarizes the projected target engagement in humans on Day 14 after a single-dose administration.

TABLE 8

Mean Reduction of Free IP-10 in SAD on Day 14 (IV Administration) (Part A1)

| Dose (mg)* | 30 | 75 | 150 or TBD | 300 or TBD | 450 or TBD |
|---|---|---|---|---|---|
| Decrease of free IP-10 from baseline (%) | 37 | 65 | 89 | 97 | 98 |

*After the first dose panel, all remaining dose levels are placeholder doses and may be revised based on the real-time PK/PD analysis.

TABLE 9

Dose Ranges in SAD and Safety Margin (IV Administration) (Part A1)

| | Predicted Human Exposure | | Safety Margin from Exposure at NOAEL in the 3-month repeat-dose toxicology studies in monkeys | | Safety Margin from Exposure at LOAEL in the 3-month repeat-dose toxicology studies in monkeys | |
|---|---|---|---|---|---|---|
| Dose (mg) | Cmax (ug/mL) | AUC (ug*hr/mL) | Cmax | AUC | Cmax | AUC |
| 30 | 8 | 363 | 59 | 322 | 595 | 2331 |
| 75 | 18 | 1298 | 26 | 90 | 264 | 652 |
| 150 or TBD* | 36 | 3477 | 13 | 34 | 132 | 243 |
| 300 or TBD* | 73 | 9051 | 6.4 | 13 | 65 | 93 |
| 450 or TBD* | 110 | 15451 | 4 | 8 | 43 | 55 |

*After the first 2 dose panels, all remaining dose levels are placeholder doses and may be revised based on the real-time PK/PD analysis utilizing available observed PK and PD data. Projected mean AUC in the selected dose panel will not exceed pre-specified AUC value.

After the first 2 panels are dosed with 30 mg and 75 mg, the selection of the remaining dose panels will depend on the observed PK/PD profile in healthy subjects, In order to ensure that the dose escalation provides the expected range of exposure in order to maintain appropriate safety margins, the following factors will be considered in making the decision for subsequent dose escalations. The predicted mean Cmax and AUC of the predicted dose level will not exceed the pre-specified one in Table 9. Increases in predicted dose levels between successive SAD panels will not exceed approximately 3-fold increments. The predicted mean PK exposure (AUC(INF)) in the subsequent dose panel will not exceed approximately 4-fold increase from the mean AUC(INF) in the previous dose panel. The minimum safety exposure margins for Cmax and AUC(INF) from the NOAEL exposure will be maintained at 4 and 8-fold, respectively.

Dose Selection Justification in SC

Following IV administration of at least 2 dose panels in the SAD, a feasibility assessment will be performed to decide whether to administer BMS-986184 subcutaneously. The formulation for SC administration is available in a strength of 40 mg/mL. Further testing of BMS-986184 following SC administration will be explored if the intended TE is achieved (Table 9) following an IV administration and is considered achievable without the need to administer too many SC injections.

Matching dose levels are necessary to appropriately evaluate the absolute bioavailability because of the anticipated non-linear PK of BMS-986184 and the subsequent dose-dependent bioavailability. If conducted, the dose levels via a SC route will be matched to the corresponding IV dose. The SC dose level of Panel S6 may be similar to IV dose Panels S2 or S3, and the SC dose level of Panel S7 may be similar to IV dose Panels S3 or S4. The dose will be selected based on the available PK, TE, safety data in SAD and the consideration of potential dose levels being tested in Part B. The predicted mean Cmax and AUC for SC panels will not exceed mean Cmax and AUC at corresponding dose levels following an IV administration.

Dose Selection Justification for MAD in Healthy Participants (Part A2)

In Part A2, the MAD portion of the study, two dose levels may be studied to characterize the safety, tolerability, and sustained TE after the multiple dosing of BMS-986184. In Part A2, the dose levels being tested in the MAD panels (M1 and M2) as well as the route of administration (IV and/or SC) will be decided based on the PK/PD modeling utilizing the available safety, PK, and TE data obtained from Part A1 SAD of the study and potential therapeutic dose levels being tested in Part B. The goals of the MAD portion of the study are to select dose levels that achieve and sustain approximately 50% or greater reduction in free IP-10 over the dosing interval, while ensuring that the safety exposure margins for Cmax and AUC(INF) from the NOAEL exposure are at least 5-fold and 10-fold, respectively. The selection of the dosing interval will depend on the observed PK (i.e., T-HALF) and the PD (maintenance of IP-10 suppression over time). Currently, a 2-week dosing interval is considered desirable, however, 1 week may be considered based on the observed PK/PD and safety profile.

For the first dose panel (M1), the dose will be selected after PK, TE, and safety data from the first 3 SAD panels (S1-S3) are reviewed and the data are deemed safe to proceed. The dose level may be similar to Panels S2 or S3 considering observed PK, TE, safety, and projected steady state PK and TE after multiple dosing. For the second dose panel (M2), the dose level will be selected after PK, TE, and safety data after the first 4 SAD panels (S1-S4) are reviewed and the data are deemed safe to proceed. Table 10 illustrates the potential dose levels that may be tested in MAD and corresponding PK exposure with the safety margin.

TABLE 10

Potential Dose Levels in MAD and Safety Margin (Part A2)

| Dosing regimen | Predicted Human Exposure at steady state | | Safety Margin from Exposure at NOAEL in the 3- month repeat-dose toxicology studies in monkeys | |
|---|---|---|---|---|
| (mg/Q2W, route)* | Cmax (ug/mL) | AUC (ug*hr/mL) | Cmax | AUC |
| 50, IV | 12 | 739 | 39 | 158 |
| 50, SC | 2.8 | 352 | 167 | 332 |
| 150, IV | 37 | 3660 | 13 | 32 |
| 150, SC | 11 | 1825 | 43 | 64 |
| 300, IV | 81 | 10584 | 6 | 11 |
| 300, SC | 28 | 5860 | 17 | 20 |

*The dosing regimen and route of administration is intended for illustration purposes to provide the exposure range and corresponding safety margin. Actual dosing regimen and route of administration will be determined based on PK/PD modeling from cumulative data in SAD.

Dose Selection Justification for POM in Patients with UC (Part B)

Final determination of the dose volume and administration during the POM study (Part B) in patients with UC will be determined once PK and PD data becomes available from the SAD/MAD studies in healthy participants. The protocol will be amended at that time to include the final dose selection for the POM study in patients with UC. A single dosing regimen will be selected to test in Part B. However another dose panel may be added to include a higher dose if the observed PD is insufficient, or a lower dose for unexpected safety findings. The same considerations for route of administration (IV or SC), ability to achieve and sustain 90% or greater reduction in free IP-10, dosing interval duration, and maintenance of safety exposure margins will be applied in making the decision.

Treatment

Study treatment is defined as any investigational treatment(s), marketed product(s), placebo or medical device intended to be administered to a study participant according to the study randomization or treatment allocation.

Study treatment includes both Investigational Product (IP) and Non-investigational Product (Non-IP). An investigational product, also known as investigational medicinal product in some regions, is defined a pharmaceutical form of an active substance or placebo being tested or used as a reference in a clinical study, including products already with a marketing authorization but used or assembled (formulated or packaged) differently than the authorized form, or used for an unauthorized indication, or when used to gain further information about the authorized form. Other medications used as support or escape medication for preventative, diagnostic, or therapeutic reasons, as components of the standard of care for a given diagnosis, may be considered as non-investigational products.

For this protocol, the study drug includes investigational product BMS-986184-01 Injection, 150 mg/Vial (40 mg/mL) 3.75 mL vial and look-a-like placebo.

BMS-986184-01 or look-a-like placebo will be administered as a solution subcutaneously or intravenously, dependent on dose panel.

TABLE 11

Study treatment for IMI012004

| Product Description/Class and Dosage Form | BMS-986184-01 injection, 150 mg/vial. 3.75 ml vial |
|---|---|

TABLE 11-continued

Study treatment for IMI012004

| Potency | 40 mg/ml |
|---|---|
| IP/Non-IMP | IP |
| Blinded or Open Label | Blinded |
| Packaging/Appearance | colorless to pale yellow, clear to opalescent liquid; may contain particles |
| Storage Conditions (per label) | Store 2 to 8° C.; Do not freeze; Protected from light |

TABLE 12

Selection and Timing of Dose

| Study Treatment | Unit dose strength(s)/ Dosage level(s) | Dosage formulation Frequency of Administration | Route of Administration |
|---|---|---|---|
| Panel S1 BMS-986184-01 | 40 mg/mL/30 mg | Single Dose | IV |
| Panel S2 BMS-986184-01 | 40 mg/mL/75 mg | | |
| Panel S3 BMS-986184-01 | 40 mg/mL/150 mg or TBD | | |
| Panel S4 BMS-986184-01 | 40 mg/mL/300 mg or TBD | | |
| Panel S5 BMS-986184-01 | 40 mg/mL/450 mg or TBD | | |
| Panel M1 BMS-986184-01 | 40 mg/mL/Panel 3 or below | 40 mg/mL Q 2 weeks × 4 doses | IV or SC |
| Panel M2 BMS-986184-01 | 40 mg/mL/Panel 4 or below | 40 mg/mL Q 2 weeks × 4 doses | IV or SC |
| Panel S6 BMS-986184-01 | 40 mg/mL/150 mg or TBD | Single Dose | SC |
| Panel S7 BMS-986184-01 | 40 mg/mL/300 mg or TBD | Single Dose | SC |

Study Assessments and Procedures

Efficacy Assessments

Efficacy assessments will only be performed for Part B as measured by improvement in endoscopy and histopathology scores in participants with moderate to severe UC.

Primary Efficacy Assessments

Modified Baron Score

The modified Baron will be used to evaluate mucosal disease severity assessed via endoscopy. The modified Baron scoring system is an endoscopic index scored on a scale of 0 to 4, with higher scores indicating greater severity. The modified Baron's is scored as follows: A score of 0 indicates normal, smooth, glistening mucosa with vascular pattern visible; not friable, a score of 1 indicates granular mucosa; vascular pattern not visible; not friable; hyperemia, a score of 2 indicates same as 1; with friable mucosa but not.

Endoscopy and Endoscopic Assessments

To ensure quality data and standardization, endoscopy will be performed locally at clinical sites per Investigator's discretion using the same endoscopist throughout the trial wherever possible. Flexible sigmoidoscopy or a colonoscopy should be performed prior to dosing with study drug at the baseline (Day 1), and week 12 (Day 85) study visits. Baseline endoscopy (colonoscopy or sigmodoscopy) must be performed within 28 days of randomization, must be on file, and it should be performed as close as possible to randomization. Day 85 endoscopy (colonoscopy or sigmoidoscopy) should be performed no more than 3 days prior to or after the Day 85 visit. Either a colonoscopy or sigmoidoscopy can be performed at baseline (Day 1) and Day 85.

The procedure performed (colonoscopy or sigmoidoscopy) need not be identical for all timepoints. Screening for colon cancer should be performed as dictated by local guidelines and should be performed per Investigator's discretion. Any biopsies performed for evaluation of colon cancer will be evaluated by a local reader at the Investigator's discretion.

Additionally, any biopsies performed to obtain histologic confirmation of a diagnosis of UC will be evaluated by a local reader at the Investigator's discretion. Colonoscopy procedures performed at screening can be used to determine the endoscopy subscore component of the Mayo Score and replaces the sigmoidoscopy if performed within 28 days of randomization.

Biopsies should be taken from the most severely affected areas of the colorectum (except when specifically targeting unaffected areas on baseline endoscopy evaluation). If all parts of the colon and rectum and equally affected, rectal biopsies should be taken. For histopathology analysis, the two biopsies should preferably be taken using jumbo forceps. If ulcers are present, biopsies should be directed at the edge of the ulcer.

Endoscopy images will be obtained during each endoscopy (Days 1 and 85) and will be sent for independent endoscopic mucosal scoring by a central endoscopy reader and determination of the Mayo endoscopy score and modified Baron Score. A detailed image review charter from the central reading laboratory will outline the endoscopic procedures, video recordings, and equipment to be utilized for video capture and transmission of endoscopic recordings. For each participant, video recording of the entire endoscopic procedure will be performed using an acceptable storage medium. The endoscopic recordings will be read centrally in a blinded manner by a qualified gastroenterologist according to the image review charter. For purposes of determining participant eligibility for enrollment, the baseline Mayo Score endoscopic subscore will be determined both locally by the Investigator and by the central endoscopy reader (3rd party vendor) as described in Section 9.1.2. All other endoscopic scoring (modified Baron score at baseline, and Mayo endoscopic subscore, modified Baron score at Day 85) will be performed solely by the central endoscopic reader (3rd party vendor). The Mayo score, used for clinical endpoints in the trial, will utilize the Mayo endoscopy subscore derived from the central endoscopy reader. The modified Baron score used for clinical endpoints in the trial will also be derived from the central endoscopy reader.

Collection of colonic tissue will be performed during the endoscopy procedure on Day 1 and Day 85 prior to dosing. To ensure quality data and standardization, colonic tissue histopathologic scoring (Geboes, Modified Riley, and Robarts Histopathology Index, see Section 9.1.2) on Day 1 and Day 85 will be centrally read by a single blinded pathologist contracted by the central reading laboratory. A detailed image review charter from the central reading laboratory will outline the histopathologic procedures to be utilized for secure specimen transfer, processing, slide preparation and digitization of slides for histopathologic scoring. The endoscopic recordings will be read centrally in a blinded manner by a qualified pathologist according to the image review charter.

Secondary Efficacy Assessments
Endoscopic Assessment—Modified Baron Score
Histopathologic Assessment
Modified Riley Index The modified Riley Index is a histopathologic scoring system which takes into account six features [acute inflammatory cell infiltrate (neutrophils in the lamina propria), crypt abscesses, mucin depletion, surface epithelial integrity, chronic inflammatory cell infiltrate (round cells in the lamina propria), and crypt architectural irregularities], each graded on a scale of 0-3, with higher scores indicating more severe histopathology.

Geboes Score

The Geboes Score is a histopathologic scoring system which utilizes a 6-point grading system (0-5) to measure disease activity based on architectural changes, chronic inflammatory infiltrate, lamina propria neutrophils and eosinophils, neutrophils in epithelium, crypt destruction, and erosion or ulceration. Higher grades indicate more severe disease activity.

Robarts Histopathology Index

Robarts Histopathology Index (RHI) total score ranges from 0 (no disease activity) to 33 (severe disease activity). RHI can be calculated as:

$$RHI = 1 \times \text{chronic inflammatory infiltrate level (4 levels)} +$$
$$2 \times \text{lamina propria neutrophils (4 levels)} +$$
$$3 \times \text{neutrophils in epithelium (4 levels)} + 5 \times \text{erosion or}$$
$$\text{ulceration (4 levels after combining Geboes 5.1 and 5.2)};$$

where Chronic inflammatory infiltrate
    0=No increase
    1=Mild but unequivocal increase
    2=Moderate increase
    3=Marked increase
Lamina propria neutrophils
    0=None
    1=Mild but unequivocal increase
    2=Moderate increase
    3=Marked increase
Neutrophils in epithelium
    0=None
    1=<5% crypts involved
    2=<50% crypts involved
    3=>50% crypts involved
Erosion or ulceration
    0=No erosion, ulceration or granulation tissue
    1=Recovering epithelium+ adjacent inflammation
    1=Probable erosion—focally stripped
    2=Unequivocal erosion
    3=Ulcer or granulation tissue
Clinical Assessments
The Mayo Score The Mayo Score will be used to evaluate disease activity. The Mayo scoring system is a composite index consisting of 4 disease variables (each scored on a scale of 0 to 3, with higher scores indicating greater frequency or severity): Stool Frequency, Rectal Bleeding, findings on Endoscopy, and the Physician's Global Assessment (PGA). These three items will be used to calculate the partial Mayo Score. Inclusion of the endoscopic Mayo subcomponent will be used to calculate the complete Mayo Score. Partial and total Mayo scores will be calculated automatically by IVRS and will be made available to the Investigator and Sponsor.

Mayo scores range from 0 to 12 points and utilize all 4 disease variables, with higher scores indicating more severe disease. The endoscopic subscore comprise only the endoscopic scale from 0-3. The partial Mayo score includes all components (rectal bleeding, stool frequency, physician's global assessment), except for the endoscopic subscore.

The Mayo Scoring System will be reviewed and discussed with the investigational staff at the Investigators' Meeting or other forum as a method of standardizing the grading between the investigational staff.

For the stool frequency component, a score of 0=normal number of stools for a participant, 1=one or two stools more than normal, 2=three or four stools more than normal, 3=five or more stools than normal.

For the rectal bleeding component 0=no blood seen in stool, 1=streaks of blood with stool for less than half of daily bowel movements, 2=obvious blood with stool for most of daily bowel movements, 3=blood alone passing with bowel movements.

The PGA is scored as 0=normal, 1=mild disease, 2=moderate disease, 3=severe disease Two Item Patient Related Outcome (PRO)

The Two Item PRO is a composite score using the components of Rectal Bleeding and Stool Frequency from the diary entries as an additional efficacy assessment.

Timing of Diary Entries for the Mayo Score

The timing of the diary entries depends on when the endoscopy is performed. For visits where an endoscopy is not performed (Treatment Period Days 8, 15, −29, 43, 57, and 71), participants will complete the diary entries for at least 5 days immediately preceding each study visit.

For visits when an endoscopy is performed baseline (Treatment Period Days 1 and 85), participants will complete the diary entries for at least 5 consecutive days immediately prior to the preparation day for the endoscopy. The endoscopy must be performed within 3 days (bowel preparation and endoscopic procedure days excluded) prior to the clinical assessment and prior to dosing.

Exploratory Efficacy Assessments

Endoscopic and Clinical Assessments

Modified Baron Score, clinical and histologic assessments will be used to assess endoscopic, clinical and histological remission.

Colon Mucosal Biopsy Collection

For all participants in Part B, biopsies will be performed during the endoscopies required as part of the study, or upon early termination prior to Day 85. Biopsies of 5 to 6 samples, at the most severely affected colonic site distal to 30 cm during retraction of the endoscope, will be performed at the time of each endoscopy. If the most affected area is ulcerated, the sample should be obtained from the edge of the ulcer. In the absence of any visible lesions characteristic of UC, 2 samples should be collected from the region of 10 cm on retraction of the endoscope. In addition, at the Baseline visit, 2 biopsy samples from an unaffected area (if present within 30 cm during retraction of the endoscope) should be obtained for each participant as described below. One to 2 biopsy specimens should be placed into each of the containers provided for the study. The formalin-fixed bottles are pre-filled with 10% neutral buffered formalin and the RNA later bottles are pre-filled with RNA later solutions.

Pharmacokinetics

Pharmacokinetics of BMS-986184 will be derived from serum concentration versus time data. The following pharmacokinetic parameters will be assessed in healthy participants for both SAD and MAD:

| | |
|---|---|
| Cmax | Maximum observed serum concentration |
| Tmax | Time of maximum observed serum concentration |
| T-HALF | Terminal phase half-life |
| CLT | Total body clearance (IV only) |
| CLT/F | Apparent body clearance (SC only) |

The following pharmacokinetic parameters will be assessed in healthy participants for Part A1 SAD.

| | |
|---|---|
| AUC(0-T) | Area under the serum concentration-time curve from time zero to time of last quantifiable concentration |
| AUC(INF) | Area under the serum concentration-time curve from time zero extrapolated to infinite time |
| $C_{14\,d}$ | Observed serum concentration 336 hour (14 days) post-dose |
| Vz | Volume of distribution of terminal phase (IV only) |
| Vz/F | Volume of distribution of terminal phase (SC only) |
| Vss | Volume of distribution at steady state (IV only) |
| MRT | Mean residence time (IV only) |

The following pharmacokinetic parameters will be assessed in healthy participants for Part A2 MAD.

| | |
|---|---|
| AUC(TAU) | Area under the serum concentration-time curve over a dosing interval |
| Ctau | Observed serum concentration at the end of dosing interval |
| T-HALF | Terminal phase half-life (only after the last dosing) |
| CLT | Total body clearance (IV only) |
| CLT/F | Apparent body clearance (SC only) |
| AI_AUC | AUC accumulation index |
| Css-avg | Average concentration over a dosing interval |
| T-HALFeff_AUC | Effective half-life |
| Ctrough | Observed trough concentration |

The following pharmacokinetic parameters will be assessed in patients with UC for Part B POM.

| | |
|---|---|
| Ctrough | Observed trough concentration |

Individual participant pharmacokinetic parameter values will be derived by non-compartmental methods by a validated pharmacokinetic analysis program. Actual times will be used for the analyses.

TABLE 13

Pharmacokinetic Sampling Schedule for BMS-986184 - SAD (Part A1)

| Study Day of Sample Collection | Event | Time (Relative To BMS-986184 Dose) Hour:Min | BMS-986184 Blood Sample for Serum | BMS-986184 Blood Sample for Immunogenieity |
|---|---|---|---|---|
| 1 | Predose | 00:00 | X | X |
| 1 | | 00:30 | X | |
| 1 | EOI[a] | 01:00 | X | |
| 1 | | 02:00 | X | |
| 1 | | 06:00 | X | |
| 1 | | 12:00 | X | |
| 2 | | 24:00 | X | |
| 3 | | 48:00 | X | |
| 4 | | 72:00 | X | |
| 6 | | 120:00 | X | |
| 8 | | 168:00 | X | |
| 11 | | 240:00 | X | |
| 15 | | 336:00 | X | X |
| 22 | | 504:00 | X | |
| 29 | | 672:00 | X | X |

TABLE 13-continued

Pharmacokinetic Sampling Schedule for BMS-986184 - SAD (Part A1)

| Study Day of Sample Collection | Event | Time (Relative To BMS-986184 Dose) Hour:Min | BMS-986184 Blood Sample for Serum | BMS-986184 Blood Sample for Immunogenieity |
|---|---|---|---|---|
| 43 | | 1008:00 | X | X |
| 57 | | 1344:00 | X | X |

<sup>a</sup>EOI = End of Infusion, This sample should be taken immediately prior to stopping the infusion (preferably within 2 minutes prior to the end of infusion). If the end of infusion is delayed to beyond the nominal infusion duration, the collection of this sample should also be delayed accordingly.

TABLE 14

Pharmacokinetic Sampling Schedule for BMS-986184 - MAD (Part A2)

| Study Day of Sample Collection | Event | Time (Relative To BMS-986184 Dose) Hour:Min | BMS-986184 Blood Sample for Serum | BMS-986184 Blood Sample for Immunogenicity |
|---|---|---|---|---|
| 1 | Predose | 00:00 | X | X |
| 1 | | 00:30 | X | |
| 1 | EOI<sup>a</sup> | 01:00 | X | |
| 1 | | 02:00 | X | |
| 1 | | 06:00 | X | |
| 1 | | 12:00 | X | |
| 2 | | 24:00 | X | |
| 3 | | 48:00 | X | |
| 4 | | 72:00 | X | |
| 6 | | 120:00 | X | |
| 8 | | 168:00 | X | |
| 11 | | 240:00 | X | |
| 15 | predose | 00:00 | X | X |
| 29 | predose | 00:00 | X | X |
| 43 | predose | 00:00 | X | X |
| 43 | | 00:30 | X | |
| 43 | EOI<sup>a</sup> | 1:00 | X | |
| 43 | | 2:00 | X | |
| 43 | | 6:00 | X | |
| 43 | | 12:00 | X | |
| 44 | | 24:00 | X | |
| 45 | | 48:00 | X | |
| 46 | | 72:00 | X | |
| 48 | | 120:00 | X | |
| 50 | | 168:00 | X | |
| 57 | | 336:00 | X | |
| 64 | | 504:00 | X | |
| 71 | | 672:00 | X | X |
| 85 | | 1008:00 | X | |
| 99 | | 1344:00 | X | X |

<sup>a</sup>EOI = End of Infusion, This sample should be taken immediately prior to stopping the infusion (preferably within 2 minutes prior to the end of infusion) for participants following an IV administration. If the end of infusion is delayed to beyond the nominal infusion duration, the collection of this sample should also be delayed accordingly.

TABLE 15

Pharmacokinetic Sampling Schedule for BMS-986184 - POM (Part B)

| Study Day of Sample Collection | Event | Time (Relative To BMS-986184 Dose) Hour: Min | BMS-986184 Blood Sample for Serum | BMS-986184 Blood Sample for Immunogenicity |
|---|---|---|---|---|
| 1 | predose | 00:00 | X | X |
| 1 | EOI<sup>a</sup> | 01:00 | X | |
| 1 | | 06:00 | X | |
| 8 | | 168:00 | X | |
| 15 | predose | 00:00 | X | X |
| 29 | predose | 00:00 | X | X |
| 43 | predose | 00:00 | X | X |
| 57 | predose | 00:00 | X | |
| 71 | predose | 00:00 | X | X |
| 71 | EOI<sup>a</sup> | 01:00 | X | |
| 71 | | 06:00 | X | |
| 85 | | 336:00 | X | |
| 99<sup>b</sup> | | 672:00 | X | X |
| 113<sup>b</sup> | | 1008:00 | X | |
| 127<sup>b</sup> | | 1344:00 | X | X |
| AE<sup>c</sup> | | | X | X |

<sup>a</sup>EOI = End of Infusion, This sample should be taken immediately prior to stopping the infusion (preferably within 2 minutes prior to the end of infusion) for participants following an IV administration. If the end of infusion is delayed to beyond the nominal infusion duration, the collection of this sample should also be delayed accordingly.
<sup>b</sup>These samples are collected during follow-up period.
<sup>c</sup>Samples should be collected for participants who have discontinued due to adverse events.

The serum samples will be analyzed for BMS-986184 by a validated ligand-binding immunoassay. Pharmacokinetic samples collected from a participant who received placebo will not be analyzed unless a request is made to confirm placebo status.

Immunogenicity Assessments

Occurrence of specific ADAs to BMS-986184 will be determined from measurements obtained at planned time points. Analysis of samples will be performed using a validated immunoassay. Endpoints for the study are incidence rates of persistent positive ADA from initiation of drug treatment up to and including the follow up period of the last dose.

The following definitions will be applied:

ADA Status of a Participant:

Baseline ADA Positive Participant: A participant with baseline ADA positive sample ADA Positive Participant: A participant with at least one ADA positive sample relative to baseline at any time after initiation of treatment during the defined observation time period.

ADA Negative Participant: A participant with no ADA positive sample after the initiation of treatment Pharmacodynamics Fecal Calprotectin Fecal calprotectin is a surrogate marker of intestinal inflammation in IBD, as it correlates with the excretion of intestinal granulocytes. Fecal Calprotectin can be followed longitudinally as a marker of response to therapy.

High Sensitivity CRP (hsCRP)

hsCRP is a non-specific acute phase reactant marker of inflammation. hsCRP will serve as both a safety lab and can be followed longitudinally as a marker of response to therapy.

Biomarkers

Target Engagement Biomarkers

Serum IP-10 Levels for Target Engagement (Total and Free)(Part A & B)

In Part A, blood will be drawn for the measurement of serum free and total IP-10 levels to assess TE.

TABLE 16

Serum TE Biomarker Sampling Schedule BMS-986184 - SAD (Part A1)

| Study Day | Event | Time (Relative To Dosing) Hour:Min | TE Blood Sample |
|---|---|---|---|
| 1 | predose | 00:00 | X |
| 1 | | 06:00 | X |
| 2 | | 24:00 | X |
| 4 | | 72:00 | X |
| 8 | | 168:00 | X |
| 15 | | 336:00 | X |
| 22 | | 504:00 | X |
| 29 | | 672:00 | X |
| 57 | | 1344:00 | X |

TABLE 17

TE Biomarker Sampling Schedule BMS-986184 -MAD (Part A2)

| Study Day | Event | Time (Relative To Dosing) Hour:Min | TE Blood Sample |
|---|---|---|---|
| 1 | predose | 00:00 | X |
| 1 | | 06:00 | X |
| 2 | | 24:00 | X |
| 4 | | 72:00 | X |
| 8 | | 168:00 | X |
| 15 | predose | 00:00 | X |
| 29 | predose | 00:00 | X |
| 43 | predose | 00:00 | X |
| 44 | | 24:00 | X |
| 45 | | 48:00 | X |
| 46 | | 72:00 | X |
| 50 | | 168:00 | X |
| 57 | | 336:00 | X |
| 64 | | 504:00 | X |
| 71 | | 672:00 | X |
| 85 | | 1008:00 | X |
| 99 | | 1344:00 | X |

In Part B, blood will be drawn at the times indicated in Table 18 for the measurement of serum free and total IP-10 levels to assess TE. Further details of blood collection and processing will be provided to the site in the laboratory procedures manual.

TABLE 18

TE Biomarker Sampling Schedule BMS-986184 - Part B (POM)

| Study Day$^a$ | Event | Time (Relative To Dosing) Hour:Min | TE Blood Sample |
|---|---|---|---|
| 1 | predose | 00:00 | X |
| 1 | | 06:00 | X |
| 8 | | 168:00 | X |
| 15 | predose | 00:00 | X |
| 29 | predose | 00:00 | X |
| 43 | predose | 00:00 | X |

TABLE 18-continued

TE Biomarker Sampling Schedule BMS-986184 - Part B (POM)

| Study Day$^a$ | Event | Time (Relative To Dosing) Hour:Min | TE Blood Sample |
|---|---|---|---|
| 57 | | 336:00 | X |
| 85 | | 1008:00 | X |

Tissue Target Engagement Biomarkers (Part B)

Colon biopsies will be used for the measurement of free and total IP-10 levels to assess tissue TE.

Pharmacodynamic Biomarkers (Part B)

In Part B only, blood will be drawn predosing at the times for the assessment of hsCRP. Fecal calprotectin will also be measured.

Exploratory Serum/Plasma Biomarkers (Part B)

In Part B only, blood will be drawn predosing for the assessment of exploratory serum biomarkers that may correlate with neutralization of IP-10 or associated pathways. Exploratory serum biomarkers may include but are not limited to other CXCR3-related chemokines (CXCL9/MIG, CXCL11/ITAC), IL-1($\alpha$, $\beta$), IL-6, IL-10, IL-12, G-CSF, MIP-3$\beta$, IFN-$\gamma$ and novel markers that may correlate with UC disease activity and/or mucosal healing. Proteomic profiling may also be done to support understanding of the activity of BMS-986184 in ulcerative colitis.

Immune Cell Phenotyping (Part B)

In Part B only, blood will be drawn predosing for immune cell phenotyping which may include but is not limited to the following markers: CXCR3, CD3, CD4, CD56, CD16, CD45RA, CCR7. These results will be used to assess pharmacodynamic changes that may occur as a result of anti-IP-10 therapy, and/or to potentially identify baseline predictors of response.

Immunohistochemistry (Part B)

Immunohistochemistry of the formalin-fixed samples may include the following antigens per standard procedure: CD3, CD68, IP-10, Foxp3, cytokeratin 18, EpCAM, IL17, and CXCR3.

Gene Expression Profiling

Whole Blood RNA Expression (Part B)

In Part B only, blood will be drawn predosing. These samples will provide broad RNA profiling (microarray or RNA sequencing) to identify novel pharmacodynamic and efficacy biomarkers related to inflammatory and/or UC disease pathways, mechanism of action and response to treatment with BMS-986184. Furthermore, these samples will be used to search for gene expression at baseline that may be predictive of efficacy for BMS-986184-treated participants.

Tissue RNA Expression (Part B)

Colon biopsies stored in RNA later will be processed to isolate RNA. These samples will provide broad RNA profiling (microarray or RNA sequencing) to identify novel pharmacodynamic and efficacy biomarkers related to inflammatory and/or UC disease pathways, mechanism of action and response to treatment with BMS-986184. Furthermore, these samples will be used to search for gene expression at baseline that may be predictive of efficacy for BMS-986184-treated participants.

| SUMMARY OF SEQUENCE LISTING | | |
|---|---|---|
| SEQ ID NO | Description | Sequence |
| 1 | VH CDR1 a.a. IP10.1 | NNGMH |
| 2 | VH CDR2 a.a. IP10.1 | VIWEDGMNKFYVDSVKG |
| 3 | VH CDR3 a.a. IP10.1 | EGDGSGIYYYYGMDV |
| 4 | VH a.a. IP10.1 | QMQLVESGGGVVQPGRSLRLSCTASGFTFSNN GMHWVRQAPGKGLEWVAVIWFDGMNKFYVD SVKGRFTISRDNSKNTLYLEMNSLRAEDTAIYY CAREGDGSGIYYYYGMDVWGQGTTVTVSS |
| 5 | VH n.t. IP10.1 | caaatgcagc tggtggagtc tgggggaggc gtggtccagc ctgggaggtc cctgagactc tcctgtacag cgtctggatt caccttcagt aacaatggca tgcactgggt ccgccaggct ccaggcaagg ggctggagtg ggtggcagtt atatggtttg atggaatgaa taaattctat gtagactccg tgaagggccg attcaccatc tccagacaca attccaagaa cacgctgtat ctggaaatga acagcctgag agccgaggac acggctatat attactgtgc gagagaaggg gatggttcgg ggatttatta ctactacggt atggacgtct ggggccaagg gaccacggtc accgtctcct ca |
| 6 | Full-length heavy chain a.a. IP10.1 | QMQLVESGGGVVQPGRSLRLSCTASGFTFSNN GMHWVRQAPGKGLEWVAVIWFDGMNKFYVD SVKGRFTISRDNSKNTLYLEMNSLRAEDTAIYY CAREGDGSGIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 7 | VL CDR1 a.a. IP10.1 | RASQSVSSSYLA |
| 8 | VL CDR2 a.a. IP10.1 | GASSRAT |
| 9 | VL CDR3 a.a. IP10.1 | QQYGSSPIFT |
| 10 | VL a.a. IP10.1 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 11 | VL n.t. IP10.1 | gaaattgtgt tgacgcagtc tccaggcacc ctgtctttgt ctccagggga aagagccacc ctctcctgca gggccagtca gagtgttagc agcagctatt tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcacctat attcactttc ggccctggga ccaaagtgga tatcaaa |
| 12 | Full-length light chain a.a. IP10.1 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 13 | VH CDR1 a.a. IP10.44 | EYGMH |
| 14 | VH CDR2 a.a. IP10.44 | VIGFAGLIKGYADSVKG |
| 15 | VH CDR3 a.a. IP10.44 | EGAGSNIYYYYGMDV |
| 16 | VH a.a. IP10.44 | QVQLVESGGGVVQPGRSLRLSCAASGFTFSEYG MHWVRQAPGKGLEWVAVIGFAGLIKGYADSV KGRFTISRDNSKNTLYLQMNSLRAEDTAVYYC AREGAGSNIYYYYGMDVWGQGTTVTVSS |

SUMMARY OF SEQUENCE LISTING

| SEQ ID NO | Description | Sequence |
|---|---|---|
| 17 | VH n.t. IP10.44 | Caagtgcagctggtggagtctgggggaggcgtggtccagcctggggagg tccctgagactctcctgtgcagcgtctggattcaccttcagtgagtatggcat gcactgggtccgccaggctccaggcaaggggctggagtgggtggcagt tatagggtttgctggactgattaaagggtatgcagactccgtgaagggccg tttcaccatctccagagacaattccaagaacacgctgtatctgcaaatgaac agcctgagagccgaggacacggctgtatattactgtgcgagagaaggcg ctggttccaatatttactactacggtatggacgtctgggggccaagggac cacggtcaccgtctcctca |
| 18 | Full-length heavy chain a.a. IP10.44 | QVQLVESGGGVVQPGRSLRLSCAASGFTFSEY GMHWVRQAPGKGLEWVAVIGFAGLIKGYADS VKGRFTISRDNSKNTLYLQMNSLRAEDTAVYY CAREGAGSNIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 19 | VL CDR1 a.a. IP10.44 | RASQSVSSSYL |
| 20 | VL CDR2 a.a. IP10.44 | GASSRAT |
| 21 | VL CDR3 a.a. IP10.44 | QQYGSSPIFT |
| 22 | VL a.a. IP10.44 | EIVLTQSPGTLSLSPGERATLSCRASQSVSSSYLA WYQQKPGQAPRLLIYGASSRATGIPDRFSGSGS GTDFTLTISRLEPEDFAVYYCQQYGSSPIFTEGPG TKVDIK |
| 23 | VL n.t. IP10.44 | gaaattgtgt tgacgcagtc tccaggcacc ctgtctttgt ctccagggga aagagccacc ctctcctgca gggccagtca gagtgttagc agcagctatt tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcacctat attcactttc ggccctggga ccaaagtgga tatcaaa |
| 24 | Full-length light chain a.a. IP10.44 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 25 | VH CDR1 a.a. IP10.45 | KHGMH |
| 26 | VH CDR2 a.a. IP10.45 | VIGFAGVIKSYADSVKG |
| 27 | VH CDR3 a.a. IP10.45 | EGEGSNIYFYYGMDV |
| 28 | VH a.a. IP10.45 | QVQLVESGGGVVQPGRSLRLSCTASGFTFSKH GMHWVRQAPGKGLEWVAVIGFAGVIKSYADS VKGRFTISRDNSKNTLYLQMNSLRAEDTAVYY CAREGEGSNIYFYYGMDVWGQGTTVTVSS |
| 29 | VH n.t. IP10.45 | Caagtgcagctggtggagtctgggggaggcgtggtccagcctggggagg tccctgagactctcctgtacagcgtctggattcaccttcagtaagcatggca tgcactgggtccgccaggctccaggcaaggggctggagtgggtggcag ttatagggttcgctggagtcattaaatcgtatgcagactccgtgaagggcc gattcaccatctccagagacaattccaagaacacgctgtatctgcaaatga acagcctgagagccgaggacacggctgtatattactgtgcgagagaagg ggaaggctcgaatatttatttctactatggtatggacgtctgggggccaaggg accacggtcaccgtctcctca |

| SUMMARY OF SEQUENCE LISTING | | |
|---|---|---|
| SEQ ID NO | Description | Sequence |
| 30 | Full-length heavy chain a.a. IP10.45 | QVQLVESGGGVVQPGRSLRLSCTASGFTFSKH GMHWVRQAPGKGLEWVAVIGFAGVIKSYADS VKGRFTISRDNSKNTLYLQMNSLRAEDTAVYY CAREGEGSNIYFYYGMDVWGQGTTVTVSSAST KGPSVFPLAPSSKSTSGGTAALGCLVKDYFPEP VTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 31 | VL CDR1 a.a. IP10.45 | RASQSVSSSYLA |
| 32 | VL CDR2 a.a. IP10.45 | GASSRAT |
| 33 | VL CDR3 a.a. IP10.45 | QQYGSSPIFT |
| 34 | VL a.a. IP10.45 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 35 | VL n.t. IP10.45 | gaaattgtgt tgacgcagtc tccaggcacc ctgtctttgt ctccagggga aagagccacc ctctcctgca gggccagtca gagtgttagc agcagctatt tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcacctat attcactttc ggccctggga ccaaagtgga tatcaaa |
| 36 | Full-length light chain a.a. IP10.45 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 37 | VH CDR1 a.a. IP10.46 | QYGMH |
| 38 | VH CDR2 a.a. IP10.46 | VISYGGDIKYYADSVKG |
| 39 | VH CDR3 a.a. IP10.46 | EGEGSNIYYYYGMDV |
| 40 | VH a.a. IP10.46 | QVQLVESGGGVVQPGRSLRLSCTASGFTFSQY GMHWVRQAPGKGLEWVAVISYGGDIKYYADS VKGRFTISRDNSKNTLYLQMNSLRAEDTAVYY CAREGEGSNIYYYYGMDVWGQGTTVTVSS |
| 41 | VH n.t. IP10.46 | Caagtgcagctggtggagtctgggggaggcgtggtccagcctggggagg tccctgagactctcctgtacagcgtctggattcaccttcagtcagtatggcat gcactgggtccgccaggctccaggcaaggggctggagtgggtggcagt tatatcgtatggtggagacataaatactatgcagactccgtaaagggccg attcaccatctccagagacaattccaaaaacacgctgtatctgcaaatgaac agcctgagagccgaggacacggctgtatattactgtgcgagagaagggg agggttctaatatattactactacggtatggacgtctggggccaagggac cacggtcaccgtctcctca |
| 42 | Full-length heavy chain a.a. IP10.46 | QVQLVESGGGVVQPGRSLRLSCTASGFTFSQY GMHWVRQAPGKGLEWVAVISYGGDIKYYADS VKGRFTISRDNSKNTLYLQMNSLRAEDTAVYY CAREGEGSNIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL |

SUMMARY OF SEQUENCE LISTING

| SEQ ID NO | Description | Sequence |
|---|---|---|
| | | MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 43 | VL CDR1 a.a. IP10.46 | RASQSVSSSYLA |
| 44 | VL CDR2 a.a. IP10.46 | GASSRAT |
| 45 | VL CDR3 a.a. IP10.46 | QQYGSSPIFT |
| 46 | VL a.a. IP10.46 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 47 | VL n.t. IP10.46 | gaaattgtgt tgacgcagtc tccaggcacc ctgtctttgt ctccagggga aagagccacc ctctcctgca gggccagtca gagtgttagc agcagctatt tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcacctat attcactttc ggccctggga ccaaagtgga tatcaaa |
| 48 | Full-length light chain a.a. IP10.46 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 49 | VH CDR1 a.a. IP10.52 | DYGMH |
| 50 | VH CDR2 a.a. IP10.52 | VIGYGGLIKGYADSVKG |
| 51 | VH CDR3 a.a. IP10.52 | EGAGSSVYYYYGMDV |
| 52 | VH a.a. IP10.52 | QVQLVESGGGVVQPGRSLRLSCTASGFTFSDY GMHWVRQAPGKGLEWVAVIGYGGLIKGYADS VKGRFTISRDNSKNTLYLQMNSLRAEDTAVYY CAREGAGSSVYYYYGMDVWGQGTTVTVSS |
| 53 | VH n.t. IP10.52 | Caagtgcagct ggtggagtct ggggggaggcgtggtccagcctggggagg tccctgagactctcctgtacagcgtctgggattccaccttcagtgactacggca tgcactgggtccgccaggctccaggcaaggggctggagtgggtggcag ttatagggtacggcggactgattaaaggatatgcagactccgtgaagggc cgattcaccatctccagagacaattccaagaacacgctgtatctgcaaatg aacagcctgagagccgaggacacggctgtatattactgtgcgagagaag gggcaggttcgagtgtgtattactactacggtatggacgtctggggccaag ggaccacggtcaccgtctcctca |
| 54 | Full-length heavy chain a.a. IP10.52 | QVQLVESGGGVVQPGRSLRLSCTASGFTFSDY GMHWVRQAPGKGLEWVAVIGYGGLIKGYADS VKGRFTISRDNSKNTLYLQMNSLRAEDTAVYY CAREGAGSSVYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 55 | VL CDR1 a.a. IP10.52 | RASQSVSSSYLA |

SUMMARY OF SEQUENCE LISTING

| SEQ ID NO | Description | Sequence |
|---|---|---|
| 56 | VL CDR2 a.a. IP10.52 | GASSRAT |
| 57 | VL CDR3 a.a. IP10.52 | QQYGSSPIFT |
| 58 | VL a.a. IP10.52 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 59 | VL n.t. IP10.52 | gaaattgtgt tgacgcagtc tccaggcacc ctgtctttgt ctccagggga aagagccacc ctctcctgca gggccagtca gagtgttagc agcagctatt tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcacctat attcactttc ggccctggga ccaaagtgga tatcaaa |
| 60 | Full-length light chain a.a. IP10.52 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 61 | VH CDR1 a.a. IP10.53 | DYGMH |
| 62 | VH CDR2 a.a. IP10.53 | VISHNGAIKGYADSVKG |
| 63 | VH CDR3 a.a. IP10.53 | EGDGSNIYYYYGMDV |
| 64 | VH a.a. IP10.53 | QVQLVESGGGVVQPGRSLRLSCAASGFTFSDY GMHWVRQAPGKGLEWVAVISHNGAIKGYADS VKGRFTISRDNSKNTLYLQMNSLRAEDTAVYY CAREGDGSNIYYYYGMDVWGQGTTVTVSS |
| 65 | VH n.t. IP10.53 | Caagtgcagctggtggagtctggggggaggcgtggtccagcctggggagg tccctgagactctcctgtgcagcgtctggattcacctcagtgactatggcat gcactgggtccgccaggctccaggcaaggggctggagtgggtggcagt tataagccataatggagccattaaaggttatgctgactccgtgaagggccg attcaccatctccagagacaattccaagaacacgctgtatctgcaaatgaa cagcctgagagccgaggacacggctgtatattactgtgcgagagaaggc gacggttcaaacatttattactactacggtatggacgtctggggccaaggg accacggtcaccgtctcctca |
| 66 | Full-length heavy chain a.a. IP10.53 | QVQLVESGGGVVQPGRSLRLSCAASGFTFSDY GMHWVRQAPGKGLEWVAVISHNGAIKGYADS VKGRFTISRDNSKNTLYLQMNSLRAEDTAVYY CAREGDGSNIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 67 | VL CDR1 a.a. IP10.53 | RASQSVSSSYLA |
| 68 | VL CDR2 a.a. IP10.53 | GASSRAT |
| 69 | VL CDR3 a.a. IP10.53 | QQYGSSPIFT |
| 70 | VL a.a. IP10.53 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |

SUMMARY OF SEQUENCE LISTING

| SEQ ID NO | Description | Sequence |
|---|---|---|
| 71 | VL n.t. IP10.53 | gaaattgtgt tgacgcagtc tccaggcacc ctgtctttgt ctccagggga aagagccacc ctctcctgca gggccagtca gagtgttagc agcagctatt tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcacctat attcactttc ggccctggga ccaaagtgga tatcaaa |
| 72 | Full-length light chain a.a. IP10.53 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 73 | VH CDR1 a.a. IP10.43 | SYGMH |
| 74 | VH CDR2 a.a. IP10.43 | VIDFVGDTKYYTDSVKG |
| 75 | VH CDR3 a.a. IP10.43 | EGAGSNIYYYYGMDV |
| 76 | VH a.a. IP10.43 | QVQLVESGGGVVQPGRSLRLSCTASGFTFSSYG MHWVRQAPGKGLEWVAVIDFVGDTKYYTDS VKGRFTISRDNSKNTLYLQMNSLRAEDTAVYY CAREGAGSNIYYYYGMDVWGQGTTVTVSS |
| 77 | VH n.t. IP10.43 | Caagtgcagct ggtggagtct gggggaggcgtggtccagcctggggagg tccctgagactctcctgtacagcgtctggattcaccttcagttcgtatggcat gcactgggtccgccaggctccaggcaaggggctggagtgggtggcagt tatagattttgtgggagacactaaatactatacagactccgtgaagggccg attcaccatctccagagacaattccaagaacacgctgtatctgcaaatgaa cagcctgagagccgaggacacggctgtatattactgtgcgagagaaggg gctggttcgaacatttattattactacggtatggacgtctggggccaaggga ccacggtcaccgtctcctca |
| 78 | Full-length heavy chain a.a. IP10.43 | QVQLVESGGGVVQPGRSLRLSCTASGFTFSSYG MHWVRQAPGKGLEWVAVIDFVGDTKYYTDS VKGRFTISRDNSKNTLYLQMNSLRAEDTAVYY CAREGAGSNIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 79 | VL CDR1 a.a. IP10.43 | RASQSVSSSHLA |
| 80 | VL CDR2 a.a. IP10.43 | GASSRAT |
| 81 | VL CDR3 a.a. IP10.43 | QQYGSSPIFT |
| 82 | VL a.a. IP10.43 | EIVLTQSPGTLSLSPGERATLSCRASQSVSSSHL AWYQQKPGQAPRLLIYGASSRATGIPDRFSGSGS GTDFTLTISRLEPEDFAVYYCQQYGSSPIFTEGP GTKVDIK |
| 83 | VL nt. IP10.43 | Gaaattgtgttgacgcagtctccaggcaccctgtctttgtctccaggggaa agagccaccctctcctgcagggccagtcagagtgttagcagcagccattt agcctggtaccagcagaaacctggccaggctcccaggctcctcatctatg gtgcatccagcagggccactggcatcccagacaggttcagtggcagtgg gtctgggacagacttcactctcaccatcagcagactggagcctgaagatttt gcagtgtattactgtcagcagtatggtagctcacctatattcactttcggccct gggaccaaagtggatatcaaa |

| SEQ ID NO | Description | Sequence |
|---|---|---|
| 84 | Full-length light chain a.a. IP10.43 | EIVLTQSPGTLSLSPGERATLSCRASQSVSSSHL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 85 | VH CDR1 a.a. IP10.47 | THGMH |
| 86 | VH CDR2 a.a. IP10.47 | VIGFGGLIKSYADSVKG |
| 87 | VH CDR3 a.a. IP10.47 | EGDGSSLYFYYGMDV |
| 88 | VH a.a. IP10.47 | QVQLVESGGGVVQPGRSLRLSCAASGFTFSTH GMHWVRQAPGKGLEWYAVIGEGGLIKSYADS VKGRFTI SRDNSKNTLYLQMNSLRAEDTAVYYCAREGD GSSLYFYYGMDVWGQGTTVTVSS |
| 89 | VH n.t. IP10.47 | Caagtgcagctggtggagtctgggggaggcgtggtccagcctgggagg tccctgagactctcctgtgcagcgtctggattcaccttcagtacccatggca tgcactgggtccgccaggctccaggcaaggggctggagtgggtggcag ttataggctttggaggactgattaaatcctatgcagactccgtgaagggccg attcaccatctccagagacaattccaagaacacgctgtatctgcaaatgaa cagcctgagagccgaggacacggctgtatattactgtgcgagagaaggt gacggttccagcctttattttactacggtatggacgtctggggccaaggga ccacggtcaccgtctcctca |
| 90 | Full-length heavy chain a.a. IP10.47 | QVQLVESGGGVVQPGRSLRLSCAASGFTFSTH GMHWVRQAPGKGLEWVAVIGFGGLIKSYADS VKGRFTISRDNSKNTLYLQMNSLRAEDTAVYY CAREGDGSSLYFYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 91 | VL CDR1 a.a. IP10.47 | RASQSVSSSYLA |
| 92 | VL CDR2 a.a. IP10.47 | GASSRAT |
| 93 | VL CDR3 a.a. IP10.47 | QQYGSSPIFT |
| 94 | VL a.a. IP10.47 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 95 | VL nt. IP10.47 | Gaaattgtgttgacgcagtctccaggcaccctgtattgtctccaggggaa agagccaccctctcctgcagggccagtcagagtgttagcagcagctattta gcctggtaccagcagaaacctggccaggctcccaggctcctcatctatgg tgcatccagcagggccactggcatcccagacaggttcagtggcagtggg tctgggacagacttcactctcaccatcagcagactggagcctgaagattttg cagtgtattactgtcagcagtatggtagctcacctatattcactttcggccctg ggaccaaagtggatatcaaa |
| 96 | Full-length light chain a.a. IP10.47 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 97 | VH CDR1 a.a. IP10.48 | NYGMH |

SUMMARY OF SEQUENCE LISTING

| SEQ ID NO | Description | Sequence |
|---|---|---|
| 98 | VH CDR2 a.a. IP10.48 | VIDFAGINKYYADSVKG |
| 99 | VH CDR3 a.a. IP10.48 | EGEGSNIYFFYGMDV |
| 100 | VH a.a. IP10.48 | QVQLVESGGGVVQPGRSLRLSCAASGFTFSNY GMHWVRQAPGKGLEWVAVIDFAGINKYYADS VKGRFTISRDNSKNTLYLQMNSLRAEDTAVYY CAREGEGSNIYFFYGMDVWGQGTTVTVSS |
| 101 | VH n.t. IP10.48 | Caagtgcagctggtggagtctggggaggcgtggtccagcctggggagg tccctgagactctCctgtgcagcgtctggattcaccttcagtaactatggcat gcactgggtccgccaggctccaggcaaggggctggagtgggtggcagt tatagattttgCgggaatcaataaatactatgcagactccgtgaagggccg attcaccatctccagagacaattccaagaacacgctgtatctgcaaatgaa cagcctgagagccgaggacacggctgtatattactgtgcgagagaagga gaaggttcaaatatttatttatttacggtatggacgtctgggccaagggac cacggtcaccgtctcctca |
| 102 | Full-length heavy chain a.a. IP10.48 | QVQLVESGGGVVQPGRSLRLSCAASGFTFSNY GMHWVRQAPGKGLEWVAVIDFAGINKYYADS VKGRFTISRDNSKNTLYLQMNSLRAEDTAVYY CAREGEGSNIYFFYGMDVWGQGTTVTVSSAST KGPSVFPLAPSSKSTSGGTAALGCLVKDYFPEP VTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 103 | VL CDR1 a.a. IP10.48 | RASQSVSSSYLA |
| 104 | VL CDR2 a.a. IP10.48 | GASSRAT |
| 105 | VL CDR3 a.a. IP10.48 | QQYGSSPIFT |
| 106 | VL a.a. IP10.48 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 107 | VL n.t. IP10.48 | Gaaattgtgttgacgcagtctccaggcaccctgtctttgtctccaggggaa agagccaccctctcctgcagggccagtcagagtgttagcagcagctattta gcctggtaccagcagaaacctggccaggctcccaggctcctcatctatgg tgcatccagcagggccactggcatcccagacaggttcagtggcagtggg tctgggacagacttcactctcaccatcagcagactggagcctgaagattttg cagtgtattactgtcagcagtatggtagctcacctatattcactttcggccctg ggaccaaagtggatatcaaa |
| 108 | Full-length light chain a.a. IP10.48 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 109 | VH CDR1 a.a. IP10.49 | QSGMH |
| 110 | VH CDR2 a.a. IP10.49 | VIGFGGLIKSYADSVKG |
| 111 | VH CDR3 a.a. IP10.49 | EGDGSGIYYYYGMDV |
| 112 | VH a.a. IP10.49 | QVQLVESGGGVVQPGRSLRLSCTASGFTFSQSG MHWVRQAPGKGLEWVAVIGFGGLIKSYADSVKG RFTISRDNSKNTLYLQMNSLRAEDTAVYYCARE GDGSGIYYYYGMDVWGQGTTVTVSS |

SUMMARY OF SEQUENCE LISTING

| SEQ ID NO | Description | Sequence |
|---|---|---|
| 113 | VH n.t. IP10.49 | Caagtgcagctggtggagtctgggggaggcgtggtccagcctggggagg<br>tccctgagactctcctgtacagcgtctggattcaccttcagtcagagtggca<br>tgcactgggtccgccaggctccaggcaaggggctggagtgggtggcag<br>ttataggggtttggcggactgattaaaagctatgcagactccgtgaagggcc<br>gattcaccatctccagagacaattccaagaacacgctgtatctgcaaatga<br>acagcctgagagccgaggacacggctgtatattactgtgcgagagaagg<br>ggatggttcggggatttattactactacggtatggacgtctgggggccaagg<br>gaccacggtcaccgtctcctca |
| 114 | Full-length heavy chain a.a. IP10.49 | QVQLVESGGGVVQPGRSLRLSCTASGFTFSQSG<br>MHWVRQAPGKGLEWVAVIGFGGLIKSYADSV<br>KGRFTISRDNSKNTLYLQMNSLRAEDTAVYYC<br>AREGDGSGIYYYYGMDVWGQGTTVTVSSAST<br>KGPSVFPLAPSSKSTSGGTAALGCLVKDYFPEP<br>VTVSWNSGALTSGVHTFPAVLQSSGLYSLSSV<br>VTVPSSSLGTQTYICNVNHKPSNTKVDKRVEPK<br>SCDKTHTCPPCPAPELLGGPSVFLFPPKPKDTL<br>MISRTPEVTCVVVDVSHEDPEVKFNWYVDGVE<br>VHNAKTKPREEQYNSTYRVVSVLTVLHQDWL<br>NGKEYKCKVSNKALPAPIEKTISKAKGQPREPQ<br>VYTLPPSREEMTKNQVSLTCLVKGFYPSDIAVE<br>WESNGQPENNYKTTPPVLDSDGSFFLYSKLTV<br>DKSRWQQGNVFSCSVMHEALHNHYTQKSLSL<br>SPGK |
| 115 | VL CDR1 a.a. IP10.49 | RASQSVSSSYLA |
| 116 | VL CDR2 a.a. IP10.49 | GASSRAT |
| 117 | VL CDR3 a.a. IP10.49 | QQYGSSPIFT |
| 118 | VL a.a. IP10.49 | EIVLTQSPGTLSLSPGERATLSCRASQSVSSSYL<br>AWYQQKPGQAPRLLIYGASSRATGIPDRFSGSG<br>SGTDFTLTISRLEPEDFAVYYCQQYGSSPIFTFG<br>PGTKVDIK |
| 119 | VL n.t. IP10.49 | Gaaattgtgttgacgcagtctccaggcaccctgtattgtctccaggggaa<br>agagccaccctctcctgcagggccagtcagagtgttagcagcagctattta<br>gcctggtaccagcagaaacctggccaggctcccaggctcctcatctatgg<br>tgcatccagcagggccactggcatcccagacaggttcagtggcagtggg<br>tctgggacagacttcactctcaccatcagcagactggagcctgaagattttg<br>cagtgtattactgtcagcagtatggtagctcacctatattcactttcggccctg<br>ggaccaaagtggatatcaaa |
| 120 | Full-length light chain a.a. IP10.49 | EIVLTQSPGTLSLSPGERATLSCRASQSVSSSYL<br>AWYQQKPGQAPRLLIYGASSRATGIPDRFSGSG<br>SGTDFTLTISRLEPEDFAVYYCQQYGSSPIFTFG<br>PGTKVDIKRTVAAPSVFIFPPSDEQLKSGTASVV<br>CLLNNFYPREAKVQWKVDNALQSGNSQESVT<br>EQDSKDSTYSLSSTLTLSKADYEKHKVYACEV<br>THQGLSSPVTKSFNRGEC |
| 121 | VH CDR1 a.a. IP10.50 | RFGMH |
| 122 | VH CDR2 a.a. IP10.50 | VIGYAGDNKYYADSVKG |
| 123 | VH CDR3 a.a. IP10.50 | EGAGSNIYYYYGMDV |
| 124 | VH a.a. IP10.50 | QVQLVESGGGVVQPGRSLRLSCAASGFTFSRFG<br>MHWVRQAPGKGLEWVAVIGYAGDNKYYADS<br>VKGRFTISRDNSKNTLYLQMNSLRAEDTAVYY<br>CAREGAGSNIYYYYGMDVWGQGTTVTVSS |
| 125 | VH n.t. IP10.50 | Caagtgcagctggtggagtctgggggaggcgtggtccagcctggggagg<br>tccctgagactctcctgtgcagcgtctggattcaccttcagtcgattcggcat<br>gcactgggtccgccaggctccaggcaaggggctggagtgggtggcagt<br>tataggtacgcggagacaataaatattatgcagactccgtgaagggcc<br>gattcaccatctccagagacaattccaagaacacgctgtatctgcaaatga<br>acagcctgagagccgaggacacggctgtatattactgtgcgagagaagg<br>ggcaggttcgaatatttattactactacggtatggacgtctgggggccaagg<br>gaccacggtcaccgtctcctca |

| SUMMARY OF SEQUENCE LISTING | | |
|---|---|---|
| SEQ ID NO | Description | Sequence |
| 126 | Full-length heavy chain a.a. IP10.50 | QVQLVESGGGVVQPGRSLRLSCAASGFTFSRFG MHWVRQAPGKGLEWVAVIGYAGDNKYYADS VKGRFTISRDNSKNTLYLQMNSLRAEDTAVYY CAREGAGSNIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 127 | VL CDR1 a.a. IP10.50 | RASQSVSSSYLA |
| 128 | VL CDR2 a.a. IP10.50 | GASSRAT |
| 129 | VL CDR3 a.a. IP10.50 | QQYGSSPIFT |
| 130 | VL a.a. IP10.50 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 131 | VL n.t. IP10.50 | Gaaattgtgttgacgcagtctccaggcaccctgtattgtctccaggggaa agagccaccctctcctgcagggccagtcagagtgttagcagcagctattta gcctggtaccagcagaaacctggccaggctcccaggctcctcatctatgg tgcatccagcagggccactggcatcccagacaggttcagtggcagtggg tctgggacagacttcactctcaccatcagcagactggagcctgaagattttg cagtgtattactgtcagcagtatggtagctcacctatattcactttcggccctg ggaccaaagtggatatcaaa |
| 132 | Full-length light chain a.a. IP10.50 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 133 | VH CDR1 a.a. IP10.51 | DYGMH |
| 134 | VH CDR2 a.a. IP10.51 | VIGYGGLIKGYADSVKG |
| 135 | VH CDR3 a.a. IP10.51 | EGAGSSIYYYYGMDV |
| 136 | VH a.a. IP10.51 | QVQLVESGGGVVQPGRSLRLSCTASGFTFSDY GMHWVRQAPGKGLEWVAVIGYGGLIKGYADS VKGRFTI SRDNSKNTLYLQMNSLRAEDTAVYYCAREGA GSSIYYYYGMDVWGQGTTVTVSS |
| 137 | VH n.t. IP10.51 | Caagtgcagctggtggagtctgggggaggcgtggtccagcctgggagg tccctgagactctcctgtacagcatctggattcaccttcagtgactacggcat gcactgggtccgccaggctccaggcaaggggctggagtgggtggcagt tatagggtacggcggactgattaaaggatatgcagactccgtgaagggcc gattcaccatctccagagacaattccaagaacacgctgtatctgcaaatga acagcctgagagccgaggacacggctgtatattactgtgcgagagaagg ggcaggttcgagtatatattactacggtatggacgtctggggccaagg gaccacggtcaccgtctcctca |
| 138 | Full-length heavy chain a.a. IP10.51 | QVQLVESGGGVVQPGRSLRLSCTASGFTFSDY GMHWVRQAPGKGLEWVAVIGYGGLIKGYADS VKGRFTISRDNSKNTLYLQMNSLRAEDTAVYY CAREGAGSSIYYYYGMDVWGQGTTVTVSSAS TKGPSVFPLAPSSKSTSGGTAALGCLVKDYFPE PVTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL |

SUMMARY OF SEQUENCE LISTING

| SEQ ID NO | Description | Sequence |
|---|---|---|
| | | MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |
| 139 | VL CDR1 a.a. IP10.51 | RASQSVSSSYLA |
| 140 | VL CDR2 a.a. IP10.51 | GASSRAT |
| 141 | VL CDR3 a.a. IP10.51 | QQYGSSPIFT |
| 142 | VL a.a. IP10.51 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 143 | VL n.t. IP10.51 | Gaaattgtgttgacgcagtctccaggcaccctgtattgtctccaggggaa agagccaccctctcctgcagggccagtcagagtgttagcagcagctattta gcctggtaccagcagaaacctggccaggctcccaggctcctcatctatgg tgcatccagcagggccactggcatcccagacaggttcagtggcagtggg tctgggacagacttcactctcaccatcagcagactggagcctgaagattttg cagtgtattactgtcagcagtatggtagctcacctatattcactttcggccctg ggaccaaagtggatatcaaa |
| 144 | Full-length light chain a.a. IP10.51 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 145 | VH CDR1 a.a. IP10.54 | QYGMH |
| 146 | VH CDR2 a.a. IP10.54 | VISYGGDIKYYADSVKG |
| 147 | VH CDR3 a.a. IP10.54 | EGEGSNIYYYYGMDV |
| 148 | VH a.a. IP10.54 | QVQLVESGGGVVQPGRSLRLSCTASGFTFSQY GMHWVRQAPGKGLEWVAVISYGGDIKYYADS VKGRFTISRDNSKNTLYLEMNSLRAEDTAIYYC AREGEGSNIYYYYGMDVWGQGTTVTVSS |
| 149 | VH n.t. IP10.54 | Caagtgcagctggtggagtctggggggaggcgtggtccagcctggggagg tccctgagactctcctgtacagcgtctggattcaccttcagtcagtatggcat gcactgggtccgccaggctccaggcaaggggctgagtgggtggcagt tatatcgtatggtggagacatcaaatactatgcagactccgtaaagggccg attcaccatctccagagacaattccaaaaacacgctgtatctggaaatgaa cagcctgagagccgaggacacggctatatattactgtgcgagagaaggg gagggttctaatatatattactactacggtatggacgtctggggccaaggg accacggtcaccgtctcctca |
| 150 | Full-length heavy chain a.a. IP10.54 | QVQLVESGGGVVQPGRSLRLSCTASGFTFSQY GMHWVRQAPGKGLEWVAVISYGGDIKYYADS VKGRFTISRDNSKNTLYLEMNSLRAEDTAIYYC AREGEGSNIYYYYGMDVWGQGTTVTVSSAST KGPSVFPLAPSSKSTSGGTAALGCLVKDYFPEP VTVSWNSGALTSGVHTFPAVLQSSGLYSLSSV VTVPSSSLGTQTYICNVNHKPSNTKVDKRVEPK SCDKTHTCPPCPAPELLGGPSVFLFPPKPKDTL MISRTPEVTCVVVDVSHEDPEVKFNWYVDGVE VHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTV DKSRWQQGNVFSCSVMHEALHNHYTQKSLSL SPGK |

| SUMMARY OF SEQUENCE LISTING | | |
|---|---|---|
| SEQ ID NO | Description | Sequence |
| 151 | VL CDR1 a.a. IP10.54 | RASQSVSSSYLA |
| 152 | VL CDR2 a.a. IP10.54 | GASSRAT |
| 153 | VL CDR3 a.a. IP10.54 | QQYGSSPIFT |
| 154 | VL a.a. IP10.54 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIK |
| 155 | VL n.t. IP10.54 | Gaaattgtgttgacgcagtctccaggcaccctgtattgtctccaggggaa agagccaccctcctgcagggccagtcagagtgttagcagcagctattta gcctggtaccagcagaaacctggccaggctcccaggctcctcatctatgg tgcatccagcagggccactggcatcccagacaggttcagtggcagtggg tctgggacagacttcactctcaccatcagcagactggagcctgaagattttg cagtgtattactgtcagcagtatggtagctcacctatattcactttcggccctg ggaccaaagtggatatcaaa |
| 156 | Full-length light chain a.a. IP10.54 | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPIFTFG PGTKVDIKRTVAAPSVFIFPPSDEQLKSGTASVV CLLNNFYPREAKVQWKVDNALQSGNSQESVT EQDSKDSTYSLSSTLTLSKADYEKHKVYACEV THQGLSSPVTKSFNRGEC |
| 157 | Human IP-10 a.a. | Genbank Acc. No. NP_001556 |
| 158 | Human CXCR3 a.a. | Genbank Acc. No. NP_001495 |
| 159 | Rhesus monkey IP-10 a.a. | Genbank Acc. No. AAK95955 |
| 160 | Mouse IP-10 | Genbank Acc. No. NP_067249 |
| 161 | Human MIG a.a. | Genbank Acc. No. NP_002407 |
| 162 | Human ITAC a.a.a | Genbank Acc. No. NP_005400 |
| 163 | Epitope Peptide 1 | SISNQP |
| 164 | Epitope Peptide 2 | VNPRSLEKL |
| 165 | Epitope Peptide 3 | IIPASQFCPRVEIIA |
| 166 | VH a.a. consensus all Abs (with non-IP10.1 residues underlines) | QVQLVESGGGVVQPGRSLRLSC(T, A)ASGFTFS (S, E, K, Q, T, N, R, D)(Y, H, S, F)GMHWVRQAPGKGL EWVAVI(D, G, S)(F, Y, H)(V, A, G, N)G(D, L, V, I, A) (T, I, N)K(Y, G, S)Y(T, A)DSVKGRFTISRDNSKNTLYL (Q, E)MNSLRAEDTA(V, I)YYCAREG(A, E, D)GS(N, S, G)(I, L, V)Y(Y, F)(Y, F)YGMDVWGQGTTVTVSS |
| 167 | VH a.a. consensus Abs IP10.44, IP10.45, IP10.46, IP10.52, and IP10.53 (with non-IP10.1 residues underlines) | QVQLVESGGGVVQPGRSLRLSC(T, A)ASGFTFS (E, K, Q, D)(Y, H)GMHWVRQAPGKGLEWVAVI (G, S)(F, Y, H)(A, G, N)G(D, L, V, A)IK(Y, G, S)YADSV KGRFTISRDNSKNTLYLQMNSLRAEDTAVYYC AREG(A, E)GS(N, S)(I, V)Y(Y, F)YYGMDVWGQGT TVTVSS |
| 168 | VH a.a. consensus Abs IP10.44 and IP10.52 (with non-IP10.1 residues underlines) | QVQLVESGGGVVQPGRSLRLSC(T, A)ASGFTFS (E, D)YGMHWVRQAPGKGLEWVAVI G(F, Y)(A, G)GLIKGYADSVKGRFTISRDNSKNTL YLQMNSLRAEDTAVYYCAREG AGS(N, S)(I, V)YYYYGMDVWGQGTTVTVSS |

EQUIVALENTS

Those skilled in the art will recognize or be able to ascertain, using no more than routine experimentation, many equivalents of the specific embodiments of the invention described herein. Such equivalents are intended to be encompassed by the following claims.

---

We claim:

1. A method of treating an inflammatory or autoimmune disease in a subject in need of treatment comprising administering to the subject the antibody, or antigen-binding portion thereof, that binds human IP-10, such that the inflammatory or autoimmune disease in the subject is treated, wherein the antibody comprises the CDR1, CDR2, and CDR3 regions from the heavy and light chain variable regions respectively comprising the amino acid sequences of SEQ ID NOs: 16 and 22.

2. The method of claim 1, wherein the heavy chain CDR1, CDR2, and CDR3 regions respectively comprise the amino acid sequences of SEQ ID NOs: 13, 14, and 15.

3. The method of claim 1, wherein the light chain CDR1, CDR2, and CDR3 regions respectively comprise the amino acid sequences of SEQ ID NOs: 19, 20, and 21.

4. The method of claim 1, wherein the antibody comprises a heavy chain comprising the amino acid sequence of SEQ ID NO: 18.

5. The method of claim 1, wherein the antibody comprises a light chain comprising the amino acid sequence of SEQ ID NO: 24.

6. The method of claim 1, wherein the antibody comprises heavy and light chain CDR1, CDR2, and CDR3 regions, comprising the amino acid sequences of SEQ ID NOs: 13, 14, and 15, and SEQ ID NOs: 19, 20, and 21, respectively.

7. The method of claim 1, wherein the antibody comprises heavy and light chain variable regions, respectively comprising the amino acid sequences of SEQ ID NOs: 16 and 22.

8. The method of claim 1, wherein the antibody comprises full-length heavy and light chain regions, respectively comprising the amino acid sequences of SEQ ID NOs: 18 and 24.

9. The method of claim 1, wherein the antibody exhibits one or a combination of the following properties:
  (a) inhibits binding of IP-10 to CXCR3;
  (b) inhibits IP-10 induced calcium flux;
  (c) inhibits IP-10 induced cell migration;
  (d) cross-reacts with rhesus monkey IP-10;
  (e) does not cross-react with mouse IP-10;
  (f) does not cross-react with human MIG; and/or
  (g) does not cross-react with human ITAC.

10. The method of claim 1, wherein the antibody binds to human IP-10 with a $K_D$ of $1\times10^{-9}$ M or less.

11. The method of claim 1, wherein the antibody binds to amino acid residues within SISNQP (SEQ ID NO: 163), VNPRSLEKL (SEQ ID NO: 164), and/or IIPASQFCPRVEIIA (SEQ ID NO: 165).

12. The method of claim 1, wherein the antibody is a human, humanized, or chimeric antibody.

13. The method of claim 1, wherein the antibody is an IgG1, IgG2 or IgG4 isotype.

14. The method of claim 1, wherein the antibody is an antibody fragment or a single chain antibody.

15. The method of claim 1, wherein the disease is inflammatory bowel disease (IBD).

16. The method of claim 15, wherein the IBD is ulcerative colitis or Crohn's disease.

17. The method of claim 1, wherein the disease is selected from the group consisting of rheumatoid arthritis, systemic lupus erythematosus, Type I diabetes, inflammatory skin disorders, autoimmune thyroid disease, Sjogren's syndrome, pulmonary inflammation, transplant rejection, spinal cord injury, brain injury, neurodegenerative diseases, gingivitis, gene therapy-induced inflammation, inflammatory kidney disease, multiple sclerosis, and atherosclerosis.

18. The method of claim 1, wherein the method comprises administration of a single dose of the antibody, or antigen-binding portion thereof, at a dose between 30-450 mg and/or is administered every week or every two weeks.

19. The method of claim 18, wherein the antibody, or antigen-binding portion thereof, is formulated for intravenous administration or is formulated for subcutaneous administration.

20. The method of claim 18, wherein the disorder is ulcerative colitis and wherein the method comprises intravenous administration of a single dose of about 40 mg of the antibody, or antigen-binding portion thereof, every two weeks for a period of about twelve weeks.

21. A method of treating a viral or bacterial infection involving unwanted IP-10 activity in a subject in need of treatment comprising administering to the subject the antibody, or antigen-binding portion thereof, that binds human IP-10, such that the viral or bacterial infection in the subject is treated, wherein the antibody comprises the CDR1, CDR2, and CDR3 regions from the heavy and light chain variable regions respectively comprising the amino acid sequences of SEQ ID NOs: 16 and 22.

\* \* \* \* \*